United States Patent
Page et al.

(10) Patent No.: US 12,233,263 B2
(45) Date of Patent: Feb. 25, 2025

(54) DEVICE AND METHOD TO MODULATE A NERVOUS SYSTEM STRUCTURE TO NON-INVASIVELY AND NON-DESTRUCTIVELY INHIBIT NERVOUS SIGNALING

(71) Applicant: Avent, Inc., Alpharetta, GA (US)

(72) Inventors: David M. Page, Alpharetta, GA (US); Eric A. Schepis, Alpharetta, GA (US); Jalpa Shah, Alpharetta, GA (US); Natalia Alexeeva, Alpharetta, GA (US)

(73) Assignee: Avent, Inc., Alpharetta, GA (US)

( * ) Notice: Subject to any disclaimer, the term of this patent is extended or adjusted under 35 U.S.C. 154(b) by 186 days.

(21) Appl. No.: 17/892,708

(22) Filed: Aug. 22, 2022

(65) Prior Publication Data
US 2023/0079507 A1    Mar. 16, 2023

Related U.S. Application Data

(63) Continuation of application No. 16/795,822, filed on Feb. 20, 2020, now Pat. No. 11,420,054.

(60) Provisional application No. 62/809,335, filed on Feb. 22, 2019.

(51) Int. Cl.
*A61N 1/36* (2006.01)
*A61N 1/04* (2006.01)
*A61N 1/16* (2006.01)

(52) U.S. Cl.
CPC ....... *A61N 1/36034* (2017.08); *A61N 1/0456* (2013.01); *A61N 1/0472* (2013.01); *A61N 1/16* (2013.01); *A61N 1/36014* (2013.01); *A61N 1/36021* (2013.01); *A61N 1/36031* (2017.08)

(58) Field of Classification Search
CPC . A61N 1/0456; A61N 1/36021; A61N 1/0472
See application file for complete search history.

(56) References Cited

U.S. PATENT DOCUMENTS

2013/0085551 A1* 4/2013 Bachinski .......... A61N 1/36034
607/59

* cited by examiner

*Primary Examiner* — Alyssa M Alter
(74) *Attorney, Agent, or Firm* — Meunier Carlin & Curfman LLC

(57) ABSTRACT

The present disclosure is directed to a system and method modulating targeted neural and non-neural tissue of a nervous system for the treatment of head-and-face pain. Electrical stimulation is delivered transcutaneously to the treatment site that modulates the targeted neural- and non-neural tissue of the nervous structure, inhibiting nervous signaling and the perception of pain.

20 Claims, 17 Drawing Sheets

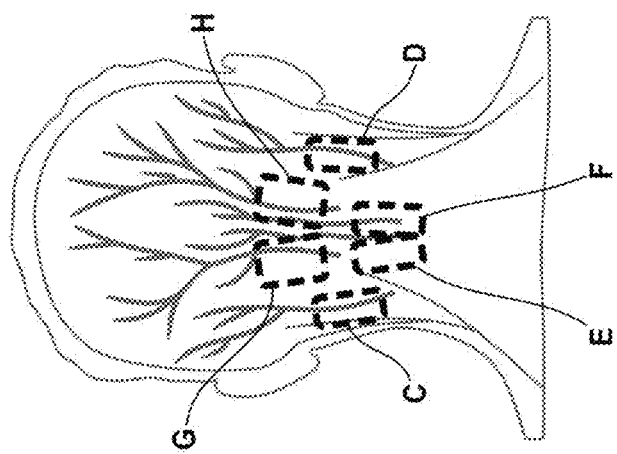
FIG. 6
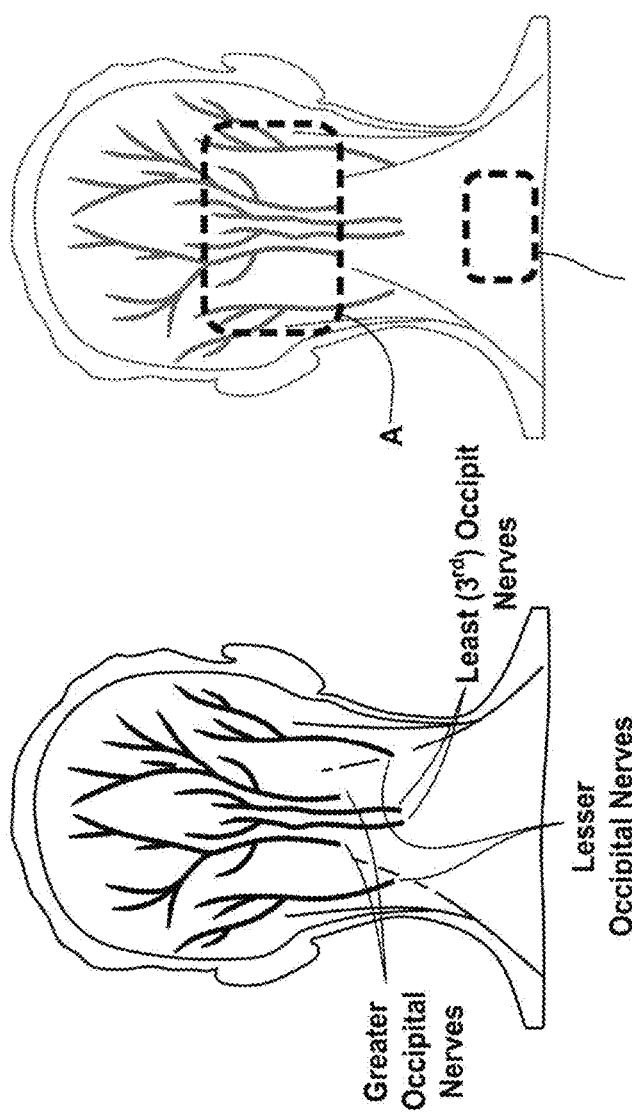
FIG. 5
FIG. 4

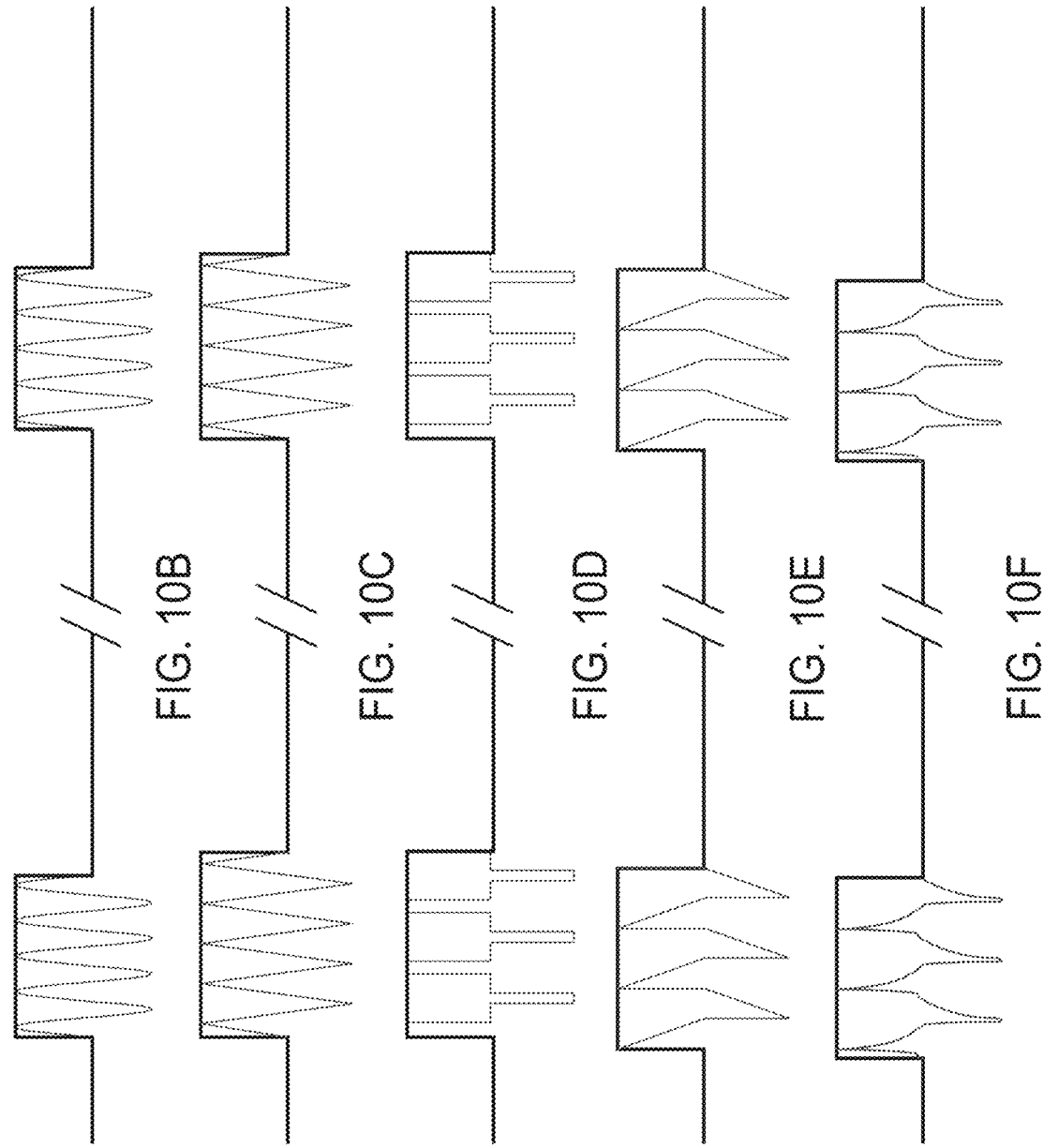

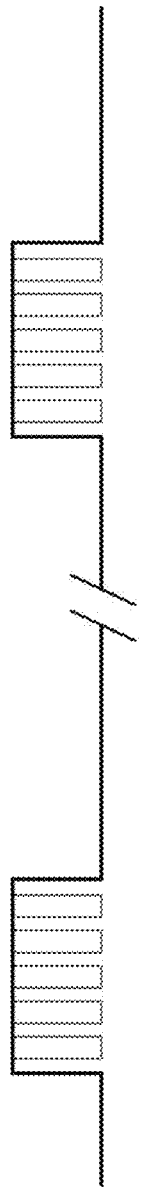

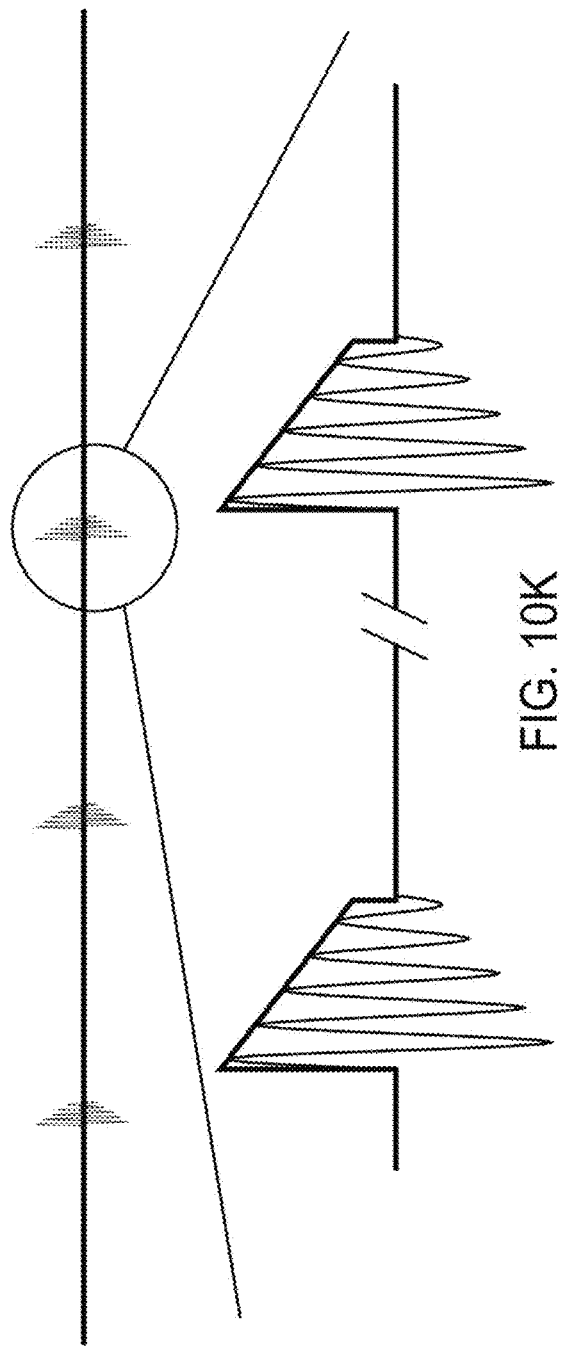
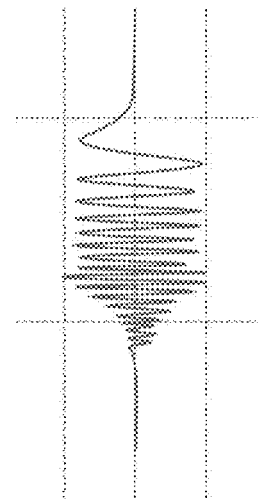
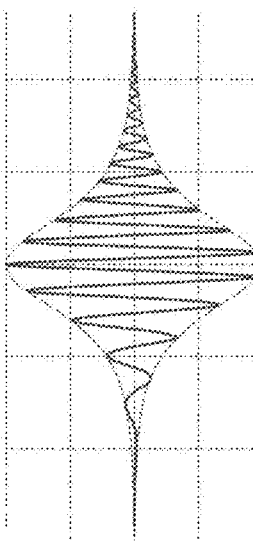
FIG. 10K
FIG. 10M
FIG. 10L

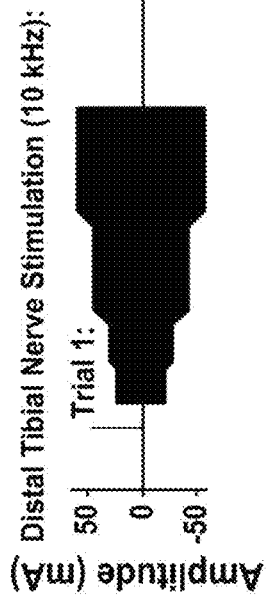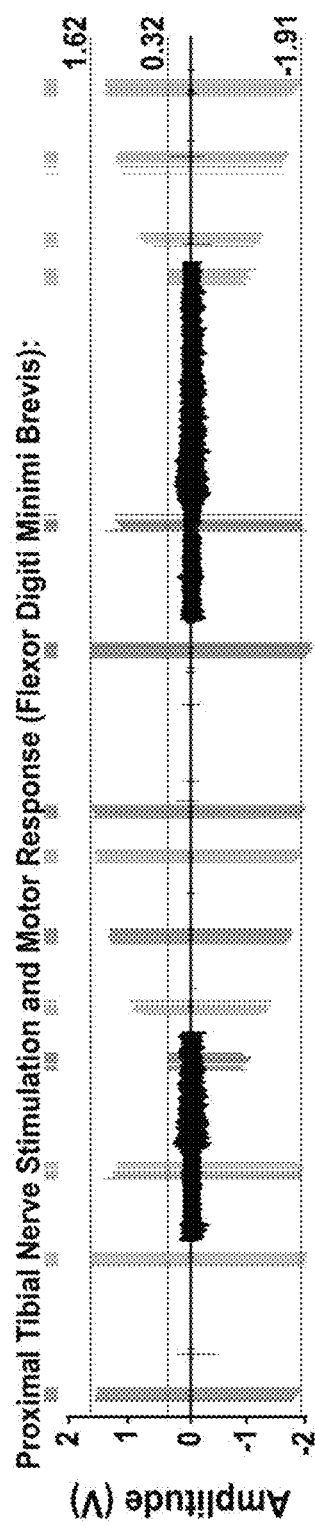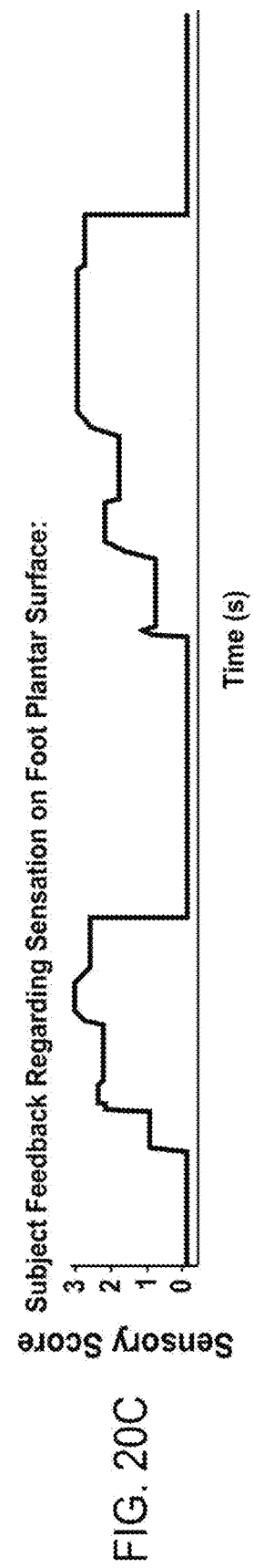
FIG. 20A
FIG. 20B
FIG. 20C

DEVICE AND METHOD TO MODULATE A NERVOUS SYSTEM STRUCTURE TO NON-INVASIVELY AND NON-DESTRUCTIVELY INHIBIT NERVOUS SIGNALING

TECHNICAL FIELD

The present invention relates generally to a device and method to modulate neural and non-neural tissue activity to treat a condition, such as pain. In particular, a device and method for transcutaneously delivering an electrical stimulation to modulate neural- and non-neural tissue of a nervous structure to inhibit nervous signaling.

BACKGROUND OF THE INVENTION

Electrical stimulation has historically been used to activate nervous signaling. For example, Transcutaneous Electrical Nerve Stimulation (TENS) has been used for decades to provide non-invasive relief from pain. TENS works by activating nervous signaling which works to reduce perceived pain by some degree via gate control theory. However, transcutaneous stimulation has not been used previously to inhibit nervous signaling.

Inhibition of nervous signaling has been performed to successfully treat pain, for example by destructive means, such as ablation of nerves, or by non-destructive means, such as the administration of local anesthetic agents (e.g. chemical inhibition). However, inhibition of nervous signaling has not been performed previously by means of non-invasive, non-destructive electrical stimulation. The inhibition of nervous signaling via a non-invasive means is important as it would allow for patients to self-administer inhibition of nervous signaling outside the medical office on an as-needed basis and/or for the acute treatment of a condition (e.g. for abortion of a migraine episode).

Historically, pain has been treated by both destructive and non-destructive methods by disrupting the transmission of pain signals that originate in the body from reaching the brain. Destructive methods are all administered by healthcare providers in a medical office setting, and are routinely used to treat chronic head and face pain indications. These include thermal ablation, cryoablation, and chemical ablations (e.g., via phenols, lidocaine, Botox™, ultrasonography ablation and mechanical transection). Destruction of the nervous structure causes an immediate loss of functionality in the nerve and may lead to long-term atrophy, neuropathy and ultimately more pain. Additionally, mixed nerves and ganglia are typically not targeted using destructive interventions for chronic pain because of the desire to maintain non-painful sensory function. Further, destruction of a nervous structure is not conducive to post-operative and peri-operative pain management, where motor and non-painful sensory function is desired to be preserved. Consequently, destructive methods for disrupting pain signals are undesirable for many conditions, and cannot be applied to all types of nervous tissue. Additionally, destructive methods cannot be self-administered by patients in a setting outside the medical office (e.g. at home or at work).

Non-destructive methods to treat head and face pain include some options that can be self-administered by patients and some options that must be administered by a healthcare provider in a medical office setting. Non-destructive methods include the use of prescription pain medications (e.g., triptans), local anesthetic injections (e.g., Botox™), topical or injected cocktails consisting of steroids and other anti-inflammatory agents, continuous infusion of local anesthetics, electrical stimulation (e.g., hypothalamic deep brain stimulation, occipital nerve stimulation, stimulation of sphenopalatine ganglion, cervical spinal cord stimulation, vagus nerve stimulation), and the application of pulsed radiofrequency energy. Each of these methods have a unique set of challenges that compromise treatment efficacy and usability. For instance, prescription pain medications can be self-administered by patients, but come with unwanted side effects and can lead to addiction or dependence. Meanwhile, local anesthetic and cocktail injections must be administered by healthcare providers, but have a short effective duration that only lasts for a few hours/days. Continuous infusion of anesthetics can be arranged to be self-administered outside the medical office, however this requires an external device be tethered to the patient, and treatments can only be delivered for days to weeks due to the need for a percutaneous entry point for tubing and the need to re-fill local anesthetic reservoirs. Additionally, the use of local anesthetics presents a risk of nerve toxicity, vascular toxicity and allergic reactions.

Electrical neuromodulation techniques can be delivered either by medical practitioners or self-administered by patients, depending on the configuration (e.g. implanted, percutaneous, transcutaneous). Electrical neuromodulation techniques pose a lower risk of side-effects than chemical interventions and provide adjustable, regional management of pain. Implanted techniques enable the patient to take home an implanted device which can often be controlled on-demand by the patient using an external control unit. However, the need for surgical implantation considerably burdens the use of these devices in both small and large nerves, and presents risks and costs that many patients are unwilling to undertake. Percutaneous electrical stimulation approaches, such as radiofrequency energy treatment, are delivered in a 'single-shot' fashion by healthcare practitioners, and do not provide patients the ability to self-administer on an as-needed basis outside the medical office. Transcutaneous electrical stimulation devices can be used non-invasively and are self-administered by patients outside the medical clinic (such as TENS units). However, non-invasive electrical stimulation approaches to-date have all relied on the activation of neural tissue in order to produce the therapeutic effects. Non-invasive electrical neuromodulation techniques that are currently used rely on activation of nerves, not inhibition of nerves, to produce the desired therapeutic effects.

As described above, existing methods for inhibiting nervous signaling are either implanted or percutaneous. Implanted devices are costly and introduce risks that many patients are unwilling to take. Percutaneous approaches must be placed by a healthcare practitioner, and cannot be used by patients over the long-term in settings outside the medical office. Thus, there is a need for a non-invasive means of inhibiting neural activity (e.g. to produce an effect similar to nerve ablation or local anesthetics). Such a non-invasive means would allow patients to self-administer an inhibition of neural activity as needed for prevention or acute treatment of a condition (e.g. abortion of migraine episodes).

As such, there is a need for an electrical device and method that can inhibit nervous activity non-invasively by modulating neural and non-neural tissue.

SUMMARY OF THE INVENTION

The present disclosure is directed to a system and method for non-invasively modulating neural and non-neural tissue of a targeted nervous system structure(s) to inhibit nervous signaling. An electrical stimulation is transcutaneously delivered to one or more treatment sites proximate the targeted nervous structure(s) that modulates the function of the neural- and non-neural tissue of the targeted nervous structure, inhibiting nervous signaling. This inhibition of nervous signaling treats a medical condition, for example, resulting in inhibition in the perception of pain. In an aspect, a system is disclosed for non-invasively modulating neural- and non-neural tissue of one or more a targeted nervous structure(s) to treat a medical condition of a patient. The system includes an electrical stimulation device comprising one or more electrodes sized and configured to be placed adjacent the skin of the patient (e.g., having a size-, shape-, and contact-surface-configuration suitable to deliver an electrical stimulation to the nervous system structure) (e.g., monopolar or bipolar) (e.g., a single electrode or an array of electrodes). The one or more electrodes delivering an electrical stimulation transcutaneously to one or more treatment sites proximate targeted nervous structure(s) and that modulate the function of a neural tissue of the targeted nervous structure(s) and/or adjacent non-neural tissue, while not damaging the tissue interposed between the stimulation device and the targeted nervous structure(s). The system also includes a controller configured to connect to the one or more electrodes of the electrical stimulation device and to a power source supplying electrical energy to the one or more electrodes, where the controller is configured to direct operation of the electrical stimulation device (e.g., via current controlled, voltage controlled, power controlled, and/or temperature controlled) to apply the electrical stimulation to one or more treatment sites through the one or more electrodes. Wherein the application of the electrical stimulation to the one or more treatment sites modulates the targeted neural- and non-neural tissue of the nervous system structure(s), inhibiting nervous signaling.

In some embodiments, the inhibition of nervous signaling (e.g., in the targeted nervous structure(s), in a downstream nervous structure) results in inhibition of perception of pain.

In some embodiments, the inhibition of nervous signaling (e.g., in the targeted nervous structure(s), in a downstream nervous structure) results from the inhibition of action potential conduction in the targeted nervous structure(s).

In some embodiments, the electrical stimulation has one or more of a frequency and amplitude sufficient to produce an inhibition of action potential conduction in the nerve fibers of the targeted nervous structure.

In some embodiments, the inhibition of nervous signaling results from inhibition of action potential conduction or inhibition of action potential activation in a nervous structure that is downstream from the targeted nervous structure (s).

In some embodiments, the pain comprises head-and-face pain. The head-and-face pain includes at least one of migraine headaches, occipital neuralgia, tension headaches, cervicogenic headaches, cluster headaches, chronic daily headaches, sinus headaches, post-traumatic headaches, exercise headaches, hemicrania continua, hormone headaches, new daily persistent headaches, chronic daily headache (transformed migraine), postherpetic neuralgia, rebound headaches, medication overuse headaches, ice pick headaches, spinal headaches, thunderclap headaches, low pressure headaches, and high pressure headaches.

In some embodiments, the application of the electrical stimulation to the targeted nervous structure reduces an intensity of an episode of head-and-face pain, reduces a duration of an episode of head-and-face pain, reduces a frequency of episodes of head-and-face pain and/or prevents episodes of head-and-face pain, the reduction in intensity, duration, frequency and prevention lasting for a period of 1 day to about 30 days after cessation of the stimulation.

In some embodiments, the application of the electrical stimulation to the targeted nervous structure aborts or reduces an intensity or duration of an episode of head-and-face pain during a period of time in which stimulation is delivered and/or for up to about of about 8 hours to about 24 hours after cessation of the stimulation.

In some embodiments, the targeted nervous structure(s) comprises at least one of the nerve trunk, branches, receptors, or nerve fibers (e.g. within the receptive field) of at least one of: a cranial nerve, a peripheral nerve, a ganglia, a plexus, an autonomic nerve, an enteric nerve, a greater occipital nerve, a lesser occipital nerve, a least occipital nerve (i.e. $3^{rd}$ occipital nerve), a trigeminal nerve, a vagus nerve, a facial nerve, a trochlear nerve, an oculomotor nerve, a glossopharyngeal nerve, an accessory nerve, a hypoglossal nerve, a cervical plexus, a supraorbital nerve, an infraorbital nerve, a sphenopalatine ganglion, a trigeminal ganglion, a posterior auricular nerve, a greater auricular nerve, a cervical nerve, a cervical cutaneous nerve, a supraclavicular nerve, a supratrochlear nerve, and a zygomaticotemporal nerve.

In some embodiments, the electrical stimulation selectively inhibits nervous signaling through at least one of a select type of neural tissue (e.g. pain-transmitting nerve fibers, non-pain transmitting nerve fibers, sensory fibers, motor fibers, proprioceptive fibers, cell bodies, axons, myelinated nerve fibers, unmyelinated nerve fibers, large-diameter nerve fibers, small-diameter nerve fibers) of a nervous structure(s) (e.g., in the targeted nervous structure, in a downstream nervous structure). The function of at least one of a non-selected type of neural tissue (e.g. pain-transmitting nerve fibers, non-pain transmitting nerve fibers, sensory fibers, motor fibers, proprioceptive fibers, cell bodies, axons, myelinated nerve fibers, unmyelinated nerve fibers, large-diameter nerve fibers, small-diameter nerve fibers) of a nervous structure(s) (e.g., in the targeted nervous structure, in a downstream nervous structure) is selectively not inhibited.

In some embodiments, the select type of neural tissue comprises pain-transmitting nerve fibers such that nervous signaling through pain-transmitting nerve fibers is inhibited and the non-selected type of neural tissue comprises non-painful sensory nerve fibers, motor fibers, and/or proprioceptive fibers such that that nervous signaling through non-painful sensory nerve fibers, motor fibers, and proprioceptive fibers is not inhibited.

In some embodiments, the select type of neural tissue comprises one of a cell body of a nervous structure(s) (e.g., of the targeted nervous structure(s), of a downstream nervous structure) and axons of the nervous structure(s), such that nervous signaling through one of the cell body and the axons is inhibited. When nervous signaling through the cell body is inhibited, nervous signally through the axons is not inhibited. When nervous signaling through the axons is inhibited, nervous signally through the cell body is not inhibited.

In some embodiments, the select type of neural tissue comprises one of myelinated fibers of a nervous structure(s) (e.g., of the targeted nervous structure(s), of a downstream nervous structure) and unmyelinated fibers of the nervous structure(s), such that nervous signaling through one of the myelinated fibers and the unmyelinated fibers is inhibited. When the nervous signaling through the myelinated fibers is inhibited, nervous signaling through the unmyelinated fibers is not inhibited. When the nervous signaling through the unmyelinated fibers is inhibited, nervous signaling through the myelinated fibers is not inhibited.

In some embodiments, the select type of neural tissue comprises at least one of large-diameter nerve fibers of a nervous structure (e.g., the targeted nervous structure(s), a downstream nervous structure) and small-diameter nerve fibers of the nervous structure(s), such that nervous signaling through one of the large-diameter nerve fiber and the small-diameter nerve fiber is inhibited. When the nervous signaling through the large-diameter nerve fiber is inhibited, nervous signaling through the small-diameter nerve fiber is not inhibited. When the nervous signaling through the small-diameter nerve fiber is inhibited, nervous signaling through the large-diameter nerve fiber is not inhibited.

In some embodiments, the electrical stimulation preferentially inhibits nervous signaling through the select type of neural tissue, where the select type of neural tissue has a larger percentage inhibition of function than the non-selected type of neural tissue.

In some embodiments, the inhibition of nervous signaling is performed without producing activation of other nerve activity including nociceptive activity, motor activity, sensory activity, autonomic activity, or enteric activity.

In some embodiments, the application of the electrical stimulation is performed at a single site on a body of the patient.

In some embodiments, the application of the electrical stimulation is performed at multiple sites simultaneously on a body of the patient.

In some embodiments, the application of the electrical stimulation to the treatment site inhibits nervous signaling in a type of neural tissue (e.g. pain-transmitting nerve fibers, non-pain transmitting nerve fibers, sensory fibers, motor fibers, proprioceptive fibers, cell bodies, axons, myelinated nerve fibers, unmyelinated nerve fibers, large-diameter nerve fibers, small-diameter nerve fibers) of a nervous structure(s) (e.g., in the targeted nervous structure, in a downstream nervous structure), while activating nervous signaling in a non-selected fiber type of neural tissue (e.g. pain-transmitting nerve fibers, non-pain transmitting nerve fibers, sensory fibers, motor fibers, proprioceptive fibers, cell bodies, axons, myelinated nerve fibers, unmyelinated nerve fibers, large-diameter nerve fibers, small-diameter nerve fibers) of a nervous structure(s) (e.g., in the targeted nervous structure, in a downstream nervous structure).

In some embodiments, the system further comprises a second electrical stimulation device that delivers an electrical stimulation transcutaneously to one or more second treatment sites proximate a second targeted nervous structure(s) that activates nervous signaling in the second targeted nervous structure(s).

In some embodiments, at least a portion of the application of the electrical stimulation at the treatment site and at least a portion of the application of electrical stimulation at the second treatment site(s) both occur simultaneously.

In some embodiments, the controller is adjustable to control output of the controller to vary at least one parameter of the electrical stimulation to inhibit nervous signaling while avoiding producing damage in the tissue interposed between the one or more electrodes and the target nervous structure(s), where the at least one parameter is selected from the group consisting of a waveform shape, a waveform frequency, a waveform amplitude, an electrical field strength generated at the electrode (e.g., as measured at the electrode or at the treatment site), a waveform DC offset, a waveform duty cycle, a tissue temperature, a cooling mechanism parameter (e.g. rate of cooling, flow rate of cooling medium, cooling medium pressure, measured temperature (e.g., at treatment site, at the one or more electrodes or a portion thereof, at the electrical stimulation device, at the patient's skin, at portion of cooling mechanism)), and a treatment duration.

In some embodiments, the electrical stimulation has a frequency from about 2 kHz to about 500 kHz.

In some embodiments, the electrical signal frequency is preferentially about 5 kHz to about 200 kHz.

In some embodiments, the electrical stimulation has a current amplitude between about 1 mA (e.g. peak-to-center, corresponding to 2 mA peak-to-peak) and about 200 mA (peak-to-center, corresponding to 400 mA peak-to-peak), a voltage amplitude between about 1 V (e.g. peak-to-center, corresponding to 2 V peak-to-peak) and about 2000 V (e.g. peak-to-center, corresponding to 4000 V peak-to-peak), or a power amplitude between about 10 mW (e.g. peak-to-center, corresponding to 20 mW peak-to-peak) and about 400 W (e.g. peak-to-center, corresponding to 800 W peak-to-peak).

In some embodiments, the electrical stimulation delivered to the one or more treatment site(s) has a waveform shape component (e.g., a continuously outputted waveform or an intermittently outputted waveform at a duty cycle (e.g., pulsed for a predefined duration)) (e.g., as a charge-balanced waveform or as a non-charge-balanced waveform) including at least one of a sinusoidal waveform, a square waveform, a triangular waveform, a stochastic noise waveform, an impulse waveform, a shape modulated waveform, a frequency modulated wave form (e.g., a chirp), an amplitude modulated waveform that provides a continuous delivery of electrical stimulation at the treatment site and a combination (e.g., additive combination) thereof, wherein each of the waveform shape components can be delivered either a single time at a given duty cycle or in a burst fashion (e.g. multiple repeats of a waveform shape delivered in a burst with bursts delivered at a given duty cycle).

In some embodiments, the waveform shape component is biphasic or charge balanced.

In some embodiments, the electrical stimulation has a duty cycle (e.g., a continuously outputted waveform or an intermittently outputted waveform at a duty cycle) from about 0.1% to about 99%.

In some embodiments, the electrical stimulation comprises bursts of waveform shapes having a burst duration of about 0.01 ms to about 1000 ms, a burst frequency from about 0.01 Hz to about 50 kHz, or an inter-burst width of about 0.01 ms to about 60 s.

In some embodiments, the electrical stimulation comprises a single pulse having a duration of 1 us to 10 μs.

In some embodiments, the electrical stimulation is delivered to the one or more treatment site(s) for a duration of up to 8 hours.

In some embodiments, the electrical stimulation is delivered to the one or more treatment site(s) for a duration of up to about 30 minutes.

In some embodiments, the electrical stimulation is current controlled, voltage controlled, or power controlled.

In some embodiments, the amplitude of the waveform is increased from an initial amplitude level to a final amplitude level over the duration of about 1 sec to about 5 mins at the onset of stimulation or at the onset of a burst of stimulation to reduce undesired activation of excitable tissues at the onset of stimulation or at the onset of a burst of stimulation.

In some embodiments, the at least one parameter of the electrical stimulation is varied to reduce at least one of an intensity, duration, and frequency of a head-and-face pain episode.

In some embodiments, the at least one parameter of the electrical stimulation is varied to selectively inhibit transmission of nervous signaling in a subset of neural tissue (e.g., pain-transmitting nerve fibers, non-pain transmitting nerve fibers, sensory fibers, motor fibers, proprioceptive fibers, cell bodies, axons, myelinated nerve fibers, unmyelinated nerve fibers, large-diameter nerve fibers, small-diameter nerve fibers) of a nervous structure(s) (e.g., in the targeted nervous structure, in a downstream nervous structure).

In some embodiments, the at least one parameter of the electrical stimulation is varied to reduce onset response of a nervous structure(s) (e.g., in the targeted nervous structure, in a downstream nervous structure) or activation of the nervous structure(s) at the onset of nervous signaling inhibition.

In some embodiments, the controller comprises a stimulator/signal generator (e.g., a function or waveform generator) (e.g., an external function or waveform generator), the stimulator/signal generator being coupled to both the electrode and an interface of the controller, where operation of the stimulator is directed by the controller to provide the electrical stimulation to the electrode.

In some embodiments, the electrode comprises an electrode assembly in the form of a paddle, cuff, cylindrical catheter or needle, wire form, or thin probe.

In some embodiments, at least one of the one or more electrodes comprises at least two electrical contacts (e.g., wherein at least one of the at least two electrical contacts is configured to be positioned near the nervous system structure during treatment), wherein the controller is configured to independently (e.g., in a multipolar manner) to direct current of the resultant electric field via each of the at least two electrical contacts.

In some embodiments, at least one of the one or more electrodes is a monopolar electrode configured to be positioned at a contact surface on the patient's skin near the target nervous structure(s), and a return electrode is at an outer surface on the patient's skin at a site distant from the targeted nervous structure(s).

In some embodiments, at least one of the one or more electrodes is a bipolar configuration, such that both an active electrode and a return electrode of the bipolar configuration are located on the patient's skin at locations near the targeted nervous structure(s).

In some embodiments, at least one of the one or more electrodes is sized (e.g., an electrical contact of the electrode has a surface area ranging from about 1 mm$^2$ to about 20,000 mm$^2$, from about 100 mm$^2$ to about 10,000 mm$^2$, or from about 200 mm$^2$ to about 5,000 mm$^2$), shaped (e.g., long and narrow), and/or oriented (e.g. a length (e.g., majority of the length) of the electrode is generally parallel to a long axis of the targeted nervous structure) to provide an electrical field of sufficient magnitude and spatial extent (e.g., maximize and direct the electrical field) along the nerve to inhibit signaling in a nervous structure(s) (e.g., in the targeted nervous structure(s), in a downstream nervous structure).

In some embodiments, at least one of the one or more electrodes includes a feature for providing non-invasive inhibition of neural signaling while avoiding damage to the tissue interposed between the electrode and the targeted nervous structure(s), wherein the feature includes at least one of controlling an amount of electrode-skin impedance, an electrode surface area, an electrode size, an electrode shape, an electrode penetration depth through an outer layer of the skin, an electrode material, an electrode coating, an electrode fastening mechanism, a cooling mechanism parameter (e.g. rate of cooling, flow rate of cooling medium, cooling medium pressure, measured temperature (e.g., at treatment site, at the one or more electrodes or a portion thereof, at the electrical stimulation device, at the patient's skin, at portion of cooling mechanism)).

In some embodiments, at least one of the one or more electrodes is designed to enable treatment of nervous structures that are part of the head, face, and neck, wherein a design feature of the at least one electrode is selected from the group consisting of electrode-skin impedance, electrode surface area, electrode size, electrode shape, electrode penetration depth through the outer layers of the skin, electrode material, electrode coating, electrode positioning, and electrode fastening mechanism.

In some embodiments, the targeted nervous structure(s) comprises one or more of the right greater occipital nerve, the left greater occipital nerve, the right lesser occipital nerve, the left lesser occipital nerve, the right least occipital nerve (i.e. 3rd occipital nerve), or the left least occipital nerve (i.e. 3rd occipital nerve), wherein the electrode is sized and configured to be positioned adjacent an outer surface of the patient's skin adjacent the targeted nervous structure(s) (e.g., having a size-, shape-, and contact-surface configuration suitable to deliver the electrical stimulation to the nervous system structure and adjacent non-neural tissue).

In some embodiments, at least one of the one or more the electrode(s) includes a conductive pathway element (e.g., a conductive gel or cream that is applied to the head and provides a conductive path between the electrode and the scalp, use of comb-like extensions from the electrode which can contact the scalp through the hair, conductive adhesive) that facilitates transmission of the electrical stimulation from the electrode towards the targeted nervous structure(s).

In some embodiments, the focused area of the electrical signal is about 0.5 mm to about 10 mm in diameter and is projected from the electrode to a location proximate a target nervous structure when the stimulation device is located adjacent an outer surface of the patient's neck or head.

In some embodiments, the stimulation device is a handheld device configured to contact an outer surface of the patient's neck or head.

In some embodiments, the stimulation device is a wearable device configured to contact an outer surface of the patient's neck or head.

In some embodiments, the stimulation device includes a body portion sized and configured to be placed adjacent to the patient's head (e.g., along the forehead, base of the skull, along the neck), where the electrode is provided on a contact surface of the body portion.

In some embodiments, the electrode has a shape (e.g., elongated rectangular shape, elongated triangular shape, a ball-tipped, or half-ball, or flat circular shape) corresponding to a size and shape of the occipital nerve such that the energy provided at the electrode can modulate an area comprising at least a portion of the occipital nerves (e.g., comprising at least a portion of all of the occipital nerves) simultaneously and the electrode can provide a uniform pressure on an outer surface of the patient's skin proximate the occipital nerve (e.g. a uniform pressure provided by the electrode applied via a transcutaneous approach on the back of the patient's head).

In some embodiments, the stimulation device has a concave curved outer surface.

In some embodiments, the outer surface has a shape corresponding to the occipital bone at the base of the patient's skull.

In some embodiments, the stimulation device is at least 17 cm wide such that the electrode is sized and configured to deliver the electrical stimulation to each of the patient's lesser occipital nerves.

In some embodiments, the stimulation device is a least 11 cm wide such that the electrode is sized and configured to deliver the electrical signal to each of the patient's greater occipital nerves.

In some embodiments, the stimulation device is a least 5 cm long such that the electrode is sized and configured to deliver the electrical signal to each of the patient's lesser and greater occipital nerves.

In some embodiments, the system further comprises a temperature sensor (e.g. a thermistor or thermocouple) coupled to the stimulation device (e.g., on a contact surface of the stimulation device) for measuring a temperature of at least one of the contact surface of the stimulation device and the patient's tissue adjacent the contact surface or the electrode, where the temperature sensor is coupled to the controller and providing thermal feedback information regarding a measured temperature (e.g., at treatment site, at the one or more electrodes or a portion thereof, at the electrical stimulation device, at the patient's skin, at portion of cooling mechanism), wherein the controller is adjustable to vary at least one parameter of the electrical stimulation (e.g. by the controller or by the user) in response to the thermal feedback information from the temperature sensor (e.g., to adjust a temperature of the contact surface to maintain the temperature of the patient's tissue (e.g., tissue comprising and surrounding the nervous system structure, skin overlying the nervous system structure) below a destructive tissue temperature and/or maintain the contact surface of the stimulation device below the destructive tissue temperature).

In some embodiments, the electrical stimulation is adjusted by the controller in response to feedback information received from the temperature sensor.

In some embodiments, the electrical stimulation is adjusted by the controller to apply the electrical stimulation while maintaining tissue temperature below 45° C.

In some embodiments, the controller is adjustable to vary at least one parameter of the electrical stimulation in response to the feedback information, the parameters including a waveform shape, a waveform frequency, a waveform amplitude, an electrical field strength generated at the electrode (e.g., as measured at the electrode or at the treatment site), a waveform DC offset, a waveform duty cycle, a tissue temperature, a cooling mechanism parameter (e.g. rate of cooling, flow rate of cooling medium, cooling medium pressure, measured temperature (e.g., at treatment site, at the one or more electrodes or a portion thereof, at the electrical stimulation device, at the patient's skin, at portion of cooling mechanism)), and a treatment duration, a continuous delivery, a pulsed delivery, a pulsed delivery envelope, a pulsed delivery envelope frequency, and a pulsed delivery duration.

In some embodiments, the system further comprises a cooling mechanism to maintain the temperature of the contact surface of the stimulation device below a threshold temperature in response to feedback information received from the thermistor.

In some embodiments, the system further comprises a display coupled to at least one of the controller and the stimulation device, the display providing an indication of the status of the stimulation device.

In some embodiments, the system further comprises a user interface (e.g., comprising a display (e.g., to provide an indication of status of the controller, stimulation device, patient)), wherein the user interface is configured to receive an input from the user (e.g., medical professional, patient) to direct the application of the electrical stimulation to the treatment site (e.g., to inhibit nervous signaling).

In some embodiments, the system further comprises at least one of a second temperature sensor coupled to an outer surface of the patient's skin, a nerve activity sensor (e.g., for measuring nervous signaling in the target nervous structure or an other non-target nervous structure), a muscle activity sensor, a patient feedback interface for receiving input from the patient and/or the user, a skin pH meter, a blood flow meter for coupling to the outer surface of the patient's skin, a skin conductance meter coupled to the outer surface of the patient's skin, a transdermal water loss sensor, a heart rate monitor for measuring the patient's heart rate, and an electrode contact impedance sensor.

In some embodiments, the controller is adjustable to vary at least one parameter of the electrical stimulation (e.g. by the controller or by the user) in response to feedback information received from at least one of the second temperature sensor, the nerve activity sensor, the muscle activity sensor, the patient feedback interface, the skin pH meter, the blood flow meter, the skin conductance meter, the transdermal water loss sensor, the heart rate monitor, and the electrode contact impedance sensor, wherein the at least one adjustable parameter is selected from the group consisting of a waveform shape, a waveform frequency, a waveform amplitude, an electrical field strength generated at the electrode (e.g., as measured at the electrode or at the treatment site), a waveform DC offset, a waveform duty cycle, a tissue temperature, a cooling mechanism parameter (e.g. rate of cooling, flow rate of cooling medium, cooling medium pressure, measured temperature (e.g., at treatment site, at the one or more electrodes or a portion thereof, at the electrical stimulation device, at the patient's skin, at portion of cooling mechanism)), and a treatment duration, a continuous delivery, a pulsed delivery, a pulsed delivery envelope, a pulsed delivery envelope frequency, and a pulsed delivery duration.

In some embodiments, the system further comprises a cooling mechanism configured to provide a cooling effect at the treatment site (e.g., contact surface of the stimulation device), wherein the cooling effect prevents damage (e.g., by pre-cooling and/or maintaining temperature of the treatment area when electrical stimulation is delivered) at the treatment site (e.g., by preserving temperatures of the patient's tissue (e.g., the patient's skin adjacent the contact surface of the stimulation device, the patient's tissue interposed between the contact surface of the stimulation device and the targeted nervous system structure(s), tissue overlying the nervous system structure(s) (e.g., skin, mucosal tissue)) below a threshold destructive tissue temperature).

In some embodiments, the electrical stimulation and the controller are portable.

In some embodiments, the electrical stimulation and the controller are non-portable.

In some embodiments, the application of the electrical stimulation is performed by a health care provider.

In some embodiments, the application of the electrical stimulation is performed by a patient as needed.

In some embodiments, at least one of the electrical stimulation device and the controller electrode is disposable.

In some embodiments, the one or more electrodes are re-usable.

In another aspect, a method is disclosed for non-invasively modulating neural- and non-neural tissue of a targeted nervous structure(s) with electrical stimulation (e.g., a single application of the electrical stimulation) to treat a medical condition of a patient. The method comprises identifying a targeted nervous system structure(s); positioning an electrical stimulation device one or more treatment sites adjacent an outer surface of the patient's skin proximate the neural- and non-neural tissue of the targeted nervous system structure(s), the electrical stimulation device comprising an electrode that provides an electrical stimulation to the treatment site(s) and a controller for directing operation of the electrode(s); and delivering an electrical stimulation transcutaneously to the treatment site via the electrode(s); wherein the application of the electrical stimulation to the treatment site(s) modulates the targeted neural- and non-neural tissue of the targeted nervous system structure(s), inhibiting nervous signaling (e.g., in the targeted nervous structure(s), in a downstream nervous structure), while not damaging tissue interposed between the stimulation device and the targeted nervous system structure(s).

In some embodiments, the inhibition of nervous signaling (e.g., in the targeted nervous structure, in a downstream nervous structure) results in inhibition of perception of pain.

In some embodiments, the inhibition of nervous signaling (e.g., in the targeted nervous structure, in a downstream nervous structure) results from the inhibition of action potential conduction in the targeted nervous structure(s).

In some embodiments, the pain comprises head-and-face pain, wherein the head-and-face pain includes at least one of migraine headaches, occipital neuralgia, tension headaches, cervicogenic headaches, cluster headaches, chronic daily headaches, sinus headaches, post-traumatic headaches, exercise headaches, hemicrania continua, hormone headaches, new daily persistent headaches, chronic daily headache (transformed migraine), postherpetic neuralgia, rebound headaches, medication overuse headaches, ice pick headaches, spinal headaches, thunderclap headaches, low pressure headaches, and high pressure headaches.

In some embodiments, the targeted nervous structure(s) comprises at least one of the nerve trunk, branches, receptors, or nerve fibers (e.g. within the receptive field) of at least one of: a cranial nerve, a peripheral nerve, a ganglia, a plexus, an autonomic nerve, an enteric nerve, a greater occipital nerve, a lesser occipital nerve, a least occipital nerve (i.e. $3^{rd}$ occipital nerve), a trigeminal nerve, a vagus nerve, a facial nerve, a trochlear nerve, an oculomotor nerve, a glossopharyngeal nerve, an accessory nerve, a hypoglossal nerve, a cervical plexus, a supraorbital nerve, an infraorbital nerve, a sphenopalatine ganglion, a trigeminal ganglion, a posterior auricular nerve, a greater auricular nerve, a cervical nerve, a cervical cutaneous nerve, and a supraclavicular nerve.

In some embodiments, the application of the electrical stimulation to the targeted nervous structure(s) reduces an intensity of an episode of head-and-face pain, reduces a duration of an episode of head-and-face pain, reduces a frequency of episodes of head-and-face pain and/or prevents episodes of head-and-face pain, the reduction in intensity, duration, frequency and prevention lasting for a period of 1 day to about 30 days after cessation of the stimulation.

In some embodiments, the application of the electrical stimulation to the targeted nervous structure(s) aborts or reduces an intensity or duration of an episode of head-and-face pain during a period of time in which stimulation is delivered and/or for up to about of about 8 hours to about 24 hours after cessation of the stimulation.

In some embodiments, application of the electrical stimulation to the targeted nervous system structure(s) selectively inhibits nervous signaling through at least one of a select type of neural tissue (e.g. pain-transmitting nerve fibers, non-pain transmitting nerve fibers, sensory fibers, motor fibers, proprioceptive fibers, cell bodies, axons, myelinated nerve fibers, unmyelinated nerve fibers, large-diameter nerve fibers, small-diameter nerve fibers) of a nervous structure(s) (e.g., in the targeted nervous structure, in a downstream nervous structure), wherein function of at least one of a non-selected type of neural tissue (e.g. pain-transmitting nerve fibers, non-pain transmitting nerve fibers, sensory fibers, motor fibers, proprioceptive fibers, cell bodies, axons, myelinated nerve fibers, unmyelinated nerve fibers, large-diameter nerve fibers, small-diameter nerve fibers) of a nervous structure(s) (e.g., in the targeted nervous structure, in a downstream nervous structure) is selectively not inhibited.

In some embodiments, the electrical stimulation modulates the function of the adjacent non-neural tissue of the targeted nervous structure by, for example, reducing blood flow to the pain-stimulating areas, reducing abnormal excitation of the peripheral pain fibers, modulating blood pressure, modulating vasodilation, modulating vasoconstriction, modulating glial cells, and/or modulating immune and inflammatory function.

In some embodiments, the application of the electrical stimulation to the treatment site inhibits nervous signaling in a type of neural tissue (e.g. pain-transmitting nerve fibers, non-pain transmitting nerve fibers, sensory fibers, motor fibers, proprioceptive fibers, cell bodies, axons, myelinated nerve fibers, unmyelinated nerve fibers, large-diameter nerve fibers, small-diameter nerve fibers) of a nervous structure(s) (e.g., in the targeted nervous structure, in a downstream nervous structure), while activating nervous signaling in a different type of neural tissue (e.g. pain-transmitting nerve fibers, non-pain transmitting nerve fibers, sensory fibers, motor fibers, proprioceptive fibers, cell bodies, axons, myelinated nerve fibers, unmyelinated nerve fibers, large-diameter nerve fibers, small-diameter nerve fibers) of a nervous structure(s) (e.g., in the targeted nervous structure, in a downstream nervous structure).

In some embodiments, the method further comprises adjusting the controller to vary at least one parameter of the electrical stimulation to inhibit nervous signaling while avoiding producing damage in the tissue interposed between the electrode and the targeted nervous system structure(s); wherein the at least one parameter is selected from the group consisting of a waveform shape, a waveform frequency, a waveform amplitude, an electrical field strength generated at the electrode (e.g., measured at the electrode or at the treatment site), a waveform DC offset, a waveform duty cycle, a tissue temperature, a cooling mechanism parameter (e.g., rate of cooling, flow rate of cooling medium, cooling medium pressure, measured temperature (e.g., at treatment site, at the one or more electrodes or a portion thereof, at the electrical stimulation device, at the patient's skin, at portion of cooling mechanism)), and a treatment duration.

In some embodiments, the method further comprises adjusting the controller to vary at least one parameter of the electrical stimulation to reduce at least one of an intensity, duration, and frequency of a head-and-face pain episode.

In some embodiments, the method further comprises adjusting the controller to vary at least one parameter of the electrical stimulation to selectively inhibit transmission of nervous signaling in a subset of neural tissue (e.g., pain-transmitting nerve fibers, non-pain transmitting nerve fibers, sensory fibers, motor fibers, proprioceptive fibers, cell bodies, axons, myelinated nerve fibers, unmyelinated nerve fibers, large-diameter nerve fibers, small-diameter nerve fibers) of a nervous structure(s) (e.g., in the targeted nervous structure, in a downstream nervous structure).

In some embodiments, the method further comprises adjusting the controller to vary at least one parameter of the electrical stimulation to reduce onset response of a nervous structure(s) (e.g., in the targeted nervous structure, in a downstream nervous structure) or activation of the nervous structure(s) at the onset of nervous signaling inhibition.

In some embodiments, the method further comprises measuring an autonomic response in the patient; and adjusting the controller to vary at least one parameter of the electrical stimulation based on a measured feedback selected from the group consisting of: measured inhibition of nervous signaling, measured temperature (e.g., at the treatment site, at the electrodes or a portion thereof, at the electrical stimulation device, at the patient's skin), input from the patient (e.g., input regarding pain sensation), a feedback corresponding to at least one of the adjustable parameters, a treatment setting associated with a time course of recovery, electrode contact impedance, electric field generated in the tissue, patient physiological response (e.g., skin pH, blood flow, skin conductance, heart rate, muscle activity (e.g., such as electromyography), and transdermal water loss), and a combination thereof.

In some embodiments, the method further comprises measuring, at a temperature sensor, a temperature of at least one of a contact surface of the stimulation device and the patient's skin adjacent the contact surface during delivery of the electrical stimulation, wherein the temperature sensor provides thermal feedback information regarding a measured temperature to the stimulation device; and adjusting the controller to vary at least one parameter of the electrical stimulation in response to the thermal feedback information received from the temperature sensor to create a cooling effect at least one of the contact surface of the stimulation device and the patient's tissue adjacent the contact surface.

In some embodiments, the method further comprises measuring, at a temperature sensor, a temperature of at least one of a contact surface of the stimulation device and the patient's skin adjacent the contact surface during delivery of the electrical stimulation, wherein the temperature sensor provides thermal feedback information regarding the measured temperature to the stimulation device; activating a cooling mechanism to cool the contact surface of the stimulation device in response to the thermal feedback information received from the temperature sensor, where cooling the contact surface prevents damage to the patient's skin/tissue when the electrical stimulation is delivered by preserving temperatures of the patient's tissue (e.g., the patient's skin adjacent the contact surface of the stimulation device, the patient's tissue interposed between the contact surface of the stimulation device and the targeted nervous system structure, mucosal tissue overlaying the targeted nervous system structure) below a destructive tissue temperature; and activating the cooling mechanism to maintain the temperature of the contact surface of the stimulation device below the destructive tissue temperature in response to thermal feedback information regarding the measured temperature received from the temperature sensor.

In some embodiments, the method further comprises identifying a second targeted nervous system structure; positioning a second electrical stimulation device at a second treatment site adjacent an outer surface of the patient's skin proximate neural- and non-neural tissue of the second targeted nervous system structure, the second electrical stimulation device comprising a second electrode that provides electrical stimulation to the second treatment site and a second controller for directing operation of the second electrode; and delivering a second electrical stimulation transcutaneously to the second treatment site via the second electrode; wherein the application of the electrical stimulation to the second treatment site modulates the function of at least one of the neural- and non-neural tissue of the second targeted nervous system structure, inhibiting nervous signaling (e.g., through the targeted neural- and non-neural tissue), while not damaging tissue interposed between the second stimulation device and the second targeted nervous system structure.

In some embodiments, the second electrical stimulation device activates nervous signaling at the second targeted nervous structure.

In some embodiments, the first and second electrical stimulation devices operate independently, wherein at least a portion of the application of the electrical stimulation at the treatment site and at least a portion of the application of electrical stimulation at the second treatment site both occur simultaneously.

In some embodiments, the step of positioning the electrical stimulation device proximate the treatment site comprises: delivering an initial stimulation to the treatment site via the electrode; measuring at least one of a voltage and a current at the electrode; and adjusting a position of the electrode at the treatment site until the measured voltage and current correspond to a threshold voltage and a threshold current, respectively.

In some embodiments, in the step of positioning the electrical stimulation device proximate the treatment site comprises: applying a conductive pathway element (e.g., a conductive gel or cream that is applied to the head and provides a conductive path between the electrode and the scalp, use of comb-like extensions from the electrode which can contact the scalp through the hair) that facilitates transmission of the electrical stimulation from the electrode towards the targeted nervous structure(s) adjacent the outer surface of the patient's skin proximate the neural- and non-neural tissue of the targeted nervous system structure(s), wherein the conductive pathway element is located at least partially between the outer surface of the patient's skin and the electrode.

In some embodiments, the step of positioning the electrical stimulation device proximate the treatment site comprises: coupling (e.g., by an adhesive, by a hair clip, by a strap that extends from the stimulation device and around at least portion of one of the patient's head and/or ears) the electrical stimulation device to the outer surface of the patient's skin.

In some embodiments, the method further comprises confirming the alignment of the electrode with the targeted nervous structure.

In some embodiments, the alignment of the electrode with the targeted nervous structure is confirmed by stimulating a physiological response in the patient (e.g., activation of nervous tissue, skin temperature, skin blood flow, skin conductance, heart rate, and muscle activity).

In some embodiments, the method further comprises measuring at least one of a nervous tissue signal, a cutaneous temperature change, a cutaneous blood flow change, a skin conductance change, and a heart rate change, and a change (e.g., an increase) in muscle activity, wherein a change (e.g., an increase) in nervous tissue signaling is indicative of placement of the stimulation device in alignment with the targeted nervous structure, wherein a change in cutaneous temperature is indicative of placement of the stimulation device in alignment with the targeted nervous structure, wherein a change (e.g., an increase or a decrease, generally dependent on the target nerve) in cutaneous blood flow is indicative of placement of the stimulation device in alignment with the targeted nervous structure, wherein change (e.g., increase or a decrease, generally dependent on the target nerve) in skin conductance is indicative of placement of placement of the stimulation device in alignment with the targeted nervous structure, and wherein a change (e.g., an increase) in muscle activity (e.g., proximate the targeted nervous structure) is indicative of placement of the stimulation device in alignment with the targeted nervous structure.

In some embodiments, the controller provides feedback information to the user via a user interface.

In some embodiments, the user modifies at least one parameter of the electrical stimulation (e.g., by providing an input at a user interface) to direct application of the electrical stimulation to the treatment site (e.g., to inhibit nervous signaling).

In another aspect, a non-transitory computer readable medium is disclosed. The computer readable medium having instructions stored thereon, wherein execution of the instructions by a processor causes the processor to perform any of the above-recited methods.

The details of one or more embodiments of the invention are set forth in the accompanying drawings and description below. Other features, objects, and advantages of the invention will be apparent from the description and drawings, and from the claims

BRIEF DESCRIPTION OF THE DRAWINGS

FIG. 4 is a schematic representation of patient anatomy;

FIG. 5 is a schematic representation of example electrode locations;

FIG. 6 is a schematic representation of example electrode locations;

FIGS. 10B, 10C, 10D, 10E, 10F, 10G, 10H, 10I, 10J, 10K, 10L, 10M, 10N, 10O, and 10P each show a waveform shape for an example electrical stimulation;

FIG. 20A is a graph providing experimental results;

FIG. 20B is a graph providing experimental results; and

FIG. 20C is a graph providing experimental results.

Like reference symbols in the various drawings indicate like elements.

Definitions

Figure 1:
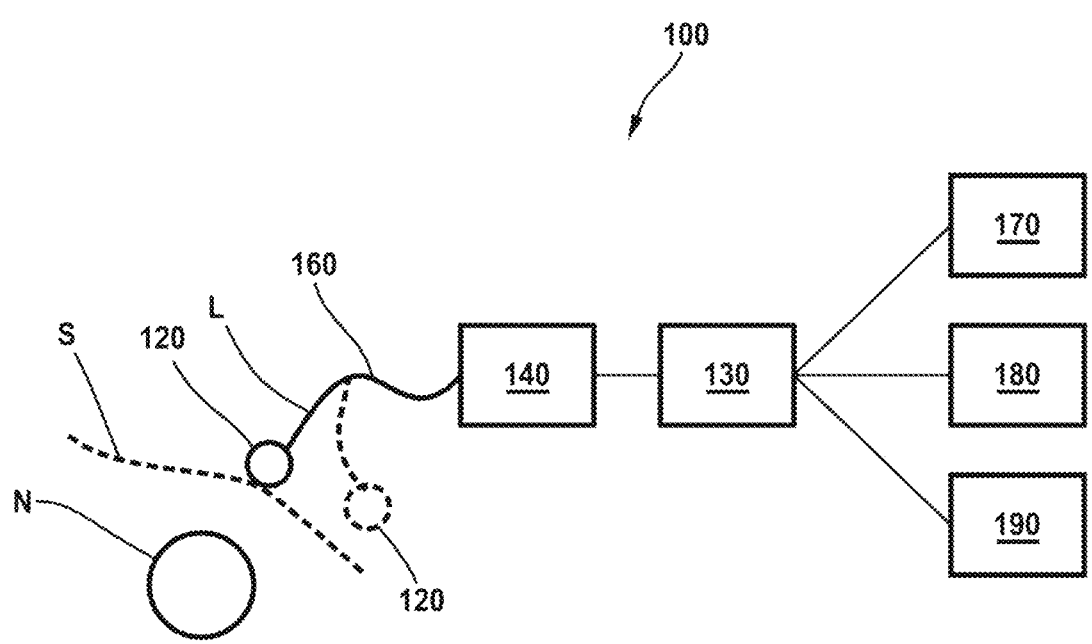
FIG. 1 is a schematic representation of an example electrical stimulation device.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

The terms "proximal" and "distal" are used herein as relative terms that refer to regions of a nerve, positions of nerves, or regions of a stimulation device. "Proximal" means a position closer to the spinal cord, brain, or central nervous system, whereas "distal" indicates a position farther from the spinal cord, brain, or central nervous system. When referring to the position on a neural structure in the peripheral nervous system or along an appendage, proximal and distal refer to positions either closer to the central nervous system or further from the central nervous system along the pathway followed by that neural structure or appendage. When referring to the position on a neural structure in the spinal cord, proximal and distal refer to positions either closer to the brain or further from the brain along the pathway followed by the neural structure.

Throughout the description and claims of this specification, the word "comprise" and variations of the word, such as "comprising" and "comprises," means "including but not limited to," and is not intended to exclude, for example, other additives, components, integers or steps. "Exemplary" and "e.g." means "an example of" and is not intended to convey an indication of a preferred or ideal aspect. "Such as" is not used in a restrictive sense, but for explanatory purposes.

As used herein, the term "nervous structure" or "neural structure" refers to a structure including neural and non-neural tissue. In addition to neural tissue (such as neurons and components of neurons including axons, cell bodies, dendrites and synapses of neurons), nervous structures may also include non-neural tissue such as glial cells, Schwann cells, myelin, immune cells, connective tissue, epithelial cells, neuroglial cells, astrocytes, microglial cells, ependymal cells, oligodendrocytes, satellite cells, cardiovascular cells, blood cells, etc.

As used herein, the term "stimulating electrode," also referred to in the case of monopolar stimulation as "the cathode," refers to an electrode responsible for delivering the therapeutic energy to the nerve. In the case of bipolar or multipolar stimulation, all of the electrical contacts are considered to be stimulating electrodes.

As used herein, "return electrode," also referred to in the case of monopolar stimulation as "the anode," refers to an electrode responsible for providing a return path for current that flows through the body. For example, the return electrode provides a return path for the current which is delivered to the target neural structure via the stimulating electrode.

As used herein, "electrical signal," "electric signal," "electrical stimulation," "stimulation electric signal," "stimulation electrical signal" and "stimulation waveform" refer to the electrical signal delivered by the controller to the tissue by means of the stimulating electrodes or, in the case of monopolar stimulation by means of the stimulating electrode and the return electrode. For example, the electrical signal may be described as a temporally-varying voltage, current, power, or other electrical measure. The delivery of the electrical signal to the target tissue is referred to as an electrical treatment, an electrical therapy, or simply a treatment or a therapy. The electrical signal creates an electrical field in the tissue such that control of the electrical signal strongly influences control of the electrical field in the tissue.

As used herein, "treatment site" refers to the site on the neural and non-neural structure to which the electrical signal is delivered by means of the electrode(s).

As used herein, "modulate" refers to modifying or changing the transmission of information. For example, this includes both excitation, pacing, and inhibition/interruption of the passage of impulses along a neuron's axon within a nerve (i.e., nerve signal transmission, nervous signaling). Modulating nerve fiber activity includes inhibiting nerve signal transmission to the point of creating a blocking effect, including a partial and a complete blocking effect. Modulating nerve activity also includes modifying the trafficking of molecules such as macromolecules along the nerve fiber. Modulating nerve activity also includes changing downstream function of the neuron (for example at cell bodies and synapses), modifying signaling in a way that changes signaling in other neurons (for example neurons in the central nervous system such as the spinal cord or the brain), modifying the function of non-neural tissue in the neural structure, or otherwise modifying the processes, function, or activity in the target neural or non-neural tissue.

As used herein, the terms "inhibit" and "attenuate" refer to any level of reduction, including partial reduction or complete reduction of nerve signal activity through a nervous structure, e.g., the reduction of the passage of impulses along a neuron's axion within a nerve. In comparative cases, partial inhibition of nerve signal activity can include inhibition of a subset of a specific groups of targeted nerve fibers, e.g., inhibition of some portion less than all of the pain transmitting nerve fibers of a targeted nervous structure. Whereas a complete or total inhibition of nerve signal activity comprises a complete inhibition of all nervous signaling in a specific group of targeted nerve fibers, e.g., a complete "block" or inhibition of all of the pain transmitting fibers of a targeted nervous structure.

As used herein, "transcutaneous" refers to electrical stimulation applied utilizing one more electrodes that do not penetrate through the surface of the skin. The electrode/stimulation device may be placed adjacent an outer surface of the patient's skin. It is contemplated that the transcutaneously placed electrode/stimulation device may penetrate the stratum corneum layer of the skin, but does not penetrate the epidermis or dermis layers. For transcutaneous electrical stimulation, it is contemplated that return electrodes or anodes may also be located on the outer surface of the patient's skin. The term "transcutaneous electrode" refers to electrode assemblies placed adjacent the patient's skin and directed into the vicinity of the nerve (mm to cm distance) in a noninvasive fashion to electrically affect the physiology of the neural structure.

As used herein, "percutaneous" refers to electrical stimulation applied utilizing one or more electrodes penetrating through the surface of the skin so an electrode delivering electrical stimulation to a target nerve beneath the skin is also located beneath the skin. For percutaneous electrical stimulation, it is contemplated that return electrodes or anodes may be located beneath the skin or on the surface of the skin. The term "percutaneous electrode" refers to electrode assemblies inserted through the skin and directed into the vicinity of the nerve (mm to cm distance) in a minimally invasive fashion to electrically affect the physiology of the neural structure.

As used herein, the terms "pain sensation" or "painful sensation" refer to a disagreeable sensation generated, for example, by the activation of sensory nociceptors. Nociception describes the perception of acute pain and is generally caused by activation of sensory nociceptors or by disruption of nociceptor pathways (e.g. severed neurons or disrupted nociceptors). Chronic pain sensation can also be generated by activation of nerve fibers which result in a disagreeable perception similar in nature to that generated by activation of nociceptors (for example, neuropathic pain). In some cases, such as following a surgery intended to treat chronic pain, both acute pain sensation and chronic pain sensation may contribute in a mixed manner to the overall pain sensation.

As used herein, the term "target nerve" is synonymous with "neural structure" or "nervous structure", and refers, for example, to mixed nerves containing motor nerve fibers and sensory nerve fibers. It may additionally refer to sensory nerves containing only sensory nerve fibers and/or to motor nerves containing only motor nerve fibers.

As used herein, the terms "transmucosal" refers to electrical stimulation applied to the mucosal tissue overlaying a targeted nervous structure using one or more electrodes. The electrical stimulation passes through the mucosal tissue to the targeted nervous structure.

As used herein, the terms "preserve" or "preserving" refer to cases where nerve function/nerve signal transmission is partially but not completely maintained, as well as cases where a function is completely maintained. In comparative cases, one function may be inhibited while another function is preserved, suggesting that, in a comparative sense, the inhibited function has experienced a magnitude of reduction greater than the magnitude of reduction experienced by the preserved function. Specifically, in comparative cases, inhibition of one function and preservation of another function does not require complete preservation or complete inhibition of either function or both functions.

DETAILED DESCRIPTION

Anatomy and Physiology

As provided above and as will be explained in more detail below, the present invention is directed to a device and method to non-invasively modulate targeted neural- and non-neural tissue of a nervous structure by the application of an electrical signal to inhibit nervous signaling. The device and method can be used, for example, to treat head-and-face pain via the application of an electrical signal to a targeted neural- and non-neural tissue of a nervous structure to modulate or inhibit nerve signaling. Example head-and-face pain can include migraine headache, cluster headache, an occipital neuralgia, tension headache, sinus headache, cervicogenic headache, postherpetic neuralgia, post-traumatic headache, chronic daily headache (transformed migraine), new daily persistent headaches, exercise headaches, hemicrania continua, hormone headache, rebound headaches, medication overuse headaches, ice pick headaches, spinal headaches, thunderclap headaches, low pressure headaches, and high pressure headaches. While primarily used to treat head-and-face pain, the device and method can also be used to treat acute pain (such as surgical pain, post-surgical pain, trauma pain), neuropathic pain, and chronic pain.

Pain is a noxious perception generated in the conscious mind. In healthy humans, perception of pain is generated by activation of sensory nociceptors and subsequent transmission of nociceptive signaling to the brain along one or more neural pathways. Pain can be created by activation of a neural pathway, at any point along that neural pathway, that results in perception of pain. In healthy humans, pain-generating neural pathways are generally activated via sensory nociceptors, which are sensory nerve endings tuned to detect and signal noxious events (e.g. noxious mechanical or thermal damage to tissue). This type of pain generally represents a genuine noxious condition, and this type of pain subsides when the noxious condition is resolved. In cases where the noxious event is not a chronic tissue dysfunction, this type of pain is referred to as acute pain. In contrast, chronic pain represents conditions where pain-generating neural pathways are persistently modulated due to chronic tissue dysfunction or neural dysfunction. This may be due to genuine activation of sensory nociceptors at a site of chronically dysfunctional tissue or due to dysfunction of the neural tissue or tissue supporting the neural tissue that results in modulation at any point along pain-generating neural pathways.

Devices to treat pain can be designed to either directly or indirectly modulate nerve signal transmission via pain-generating neural pathways at any level along these pathways. For example, direct blocking of axonal conduction in nerve fibers attached to sensory nociceptors can block perception of pain. As an additional example, indirect modulation of synaptic transmission in the spinal cord or nerve ganglia can be achieved by activating or blocking other inputs to the spinal cord or ganglia and may result in modulation along a pain-generating neural pathway. As another example, inhibition of parasympathetic outflow in the sphenopalatine ganglion can indirectly influence head and face pain, such as migraine, by modulating sensory input to the brain (for example via the superior salivatory nucleus). Thus, it is desired to target a variety of nervous structures when modulating and treating acute and chronic pain head-and-face pain.

Targeted nervous structures include nerve trunk, branches, receptors, or nerve fibers (e.g. within the receptive field) of peripheral nerves (small diameter and large diameter), cranial nerves, ganglia, autonomic nerves, and plexuses. Ganglia comprise at least one of dorsal root ganglia, a sympathetic ganglia, a parasympathetic ganglia, a sphenopalatine ganglion, a gasserian ganglion, and autonomic ganglia in general. Generally, large peripheral nerves are those peripheral nerves having a diameter greater than about 2.5 mm. Example large peripheral nerves include, for example, the femoral nerve, sciatic nerve, vagus nerve, tibial nerve, peroneal nerve, median nerve, radial nerve, and ulnar nerve. Example small peripheral nerves include, for example, the saphenous nerve, sural nerve, genicular nerves, cranial nerves, obturator nerve, and distal portions of larger nerves (such as distal portions of the vagus, tibial, peroneal, median, radial, and ulnar nerves). Example nerves located in the head and face include, for example, the greater occipital nerve, the lesser occipital nerve, the least occipital nerve (i.e., $3^{rd}$ occipital nerve), the trigeminal nerve, the vagus nerve, the facial nerve, the trochlear nerve, the oculomotor nerve, the glossopharyngeal nerve, the accessory nerve, the hypoglossal nerve, the cervical plexus, the supraorbital nerve, the infraorbital nerve, the sphenopalatine ganglion, the trigeminal ganglion, the posterior auricular nerve, the greater auricular nerve, the cervical nerve, the cervical cutaneous nerve, the supraclavicular nerve, the supratrochlear nerve, and the zygomaticotemporal nerve.

Targeted ganglia can include dorsal root ganglia, sympathetic ganglia, parasympathetic ganglia, a sphenopalatine ganglion (SPG), a gasserian ganglion, plexuses, and the spinal cord. Each of these nervous structures includes neural tissue as well as non-neural tissue which supports the neural tissue and can influence transmission of information along pain-generating neural pathways. Example non-neural tissue can include, for example, glial cells, Schwann cells, myelin, immune cells, connective tissue, epithelial cells, neuroglial cells, astrocytes, microglial cells, ependymal cells, oligodendrocytes, satellite cells, cardiovascular cells, blood cells, etc. Neural tissue generally refers to neurons which include components such as axons, cell bodies, dendrites, receptor endings, receptors, and synapses.

Importantly, in the context of the present invention, modulation of neural tissue (neurons including components such as axons, cell bodies, dendrites, receptor endings, receptors, and synapses) and/or non-neural tissue (such as glial cells, Schwann cells, myelin, immune cells, connective tissue, neuroglial cells, astrocytes, microglial cells, ependymal cells, oligodendrocytes, satellite cells, cardiovascular cells, and blood cells, etc.) may be responsible in part or in whole for the therapeutic inhibition of perception of pain.

Peripheral nerves are primarily composed of axons, while other neural structures, such as ganglia and the spinal cord, include many components including axons, cell bodies, dendrites, and synapses. Within a nervous structure there is variability in the nature of these components, including, for example, variability in the size, shape, and interface with supporting non-neural tissue. For example, peripheral nerves often contain both large-diameter and small-diameter axons. Schwann cells are non-neural supporting cells which surround some axons and comprise an insulating cover rich in layers of lipid bilayers referred to as the myelin sheath. Some axons are surrounded by a myelin sheath, and some axons are not surrounded by a myelin sheath. Generally, the structure of different neural components is related to their function. For example, large-diameter axons typically transmit neural signals more-quickly than small-diameter axons due to the relatively large increase in axial conductance relative to a modest increase in membrane conductance as a function of diameter. Similarly, the presence of a myelin sheath on large-diameter axons further increases the speed of conduction velocity of the action potential by increasing the resistance to trans-membrane current flow between unmyelinated areas of the axon, referred to as nodes of Ranvier. Nodes of Ranvier are brief un-myelinated portions of the fibers; action potentials are relayed along the axon by a burst of trans-membrane current flow at each subsequent node of Ranvier. Peripheral nerve axons which generally transmit information from the periphery toward the central nervous system (e.g. sensory information including pain) are often referred to as afferent fibers, while axons which generally transmit information from the central nervous system toward the periphery (e.g. motor information) are often referred to as efferent fibers.

As used herein, the term "A fiber" refers to myelinated afferent or efferent peripheral axons of the somatic nervous system. Generally speaking, A fibers are associated with proprioception, somatic motor function, sensations of touch and pressure and also sensations of pain and temperature. A fibers generally have a diameter of about 1 to 22 micrometers ($\mu$m) and conduction velocities between about 2 meter per second (m/s) to more than 100 m/s. Each A fiber has dedicated Schwann cells forming the myelin sheath around the fiber. As described above, the myelin sheath has a high content of lipids, increasing the electrical resistance to trans-membrane current flow and contributes to the high conduction velocity of action potentials along the nerve fiber. A fibers include the alpha, beta, delta, and gamma fibers. The alpha, beta, and gamma A fibers have diameters ranging from 5 micrometers to 20 micrometers ($\mu$m) and are associated with motor function, low-threshold sensory function, and proprioception, but not pain. Delta A fibers are associated with pain, and have smaller diameters ranging from 1 micrometer to 5 micrometers ($\mu$m).

As used herein, the term "C-fiber" refers to non-myelinated peripheral axons of the somatic nervous system with conduction velocities of less than about 2 m/s. C fibers have a diameter of about 0.2 to 1.5 micrometers ($\mu$m) and include the dorsal root and sympathetic fibers and are primarily associated with sensations like pain and temperature, some limited mechanoreception, reflex responses, autonomic effector activity, and visceral function.

In a peripheral nerve, pain sensation that is perceived as dull and persistent is often referred to as "slow pain" and is transmitted in peripheral nerves by C fibers which conduct neural signals relatively slowly. Pain sensation that is perceived as sharp and rapid is often referred to as 'fast pain' and is transmitted in peripheral nerves by A$\delta$ fibers which have a higher conduction velocity than C fibers. A$\delta$ fibers generally comprise small diameter sensory axons that are lightly myelinated, compared to the non-myelinated C fibers. Acute and chronic pain can involve both A$\delta$ and C fibers.

In addition to the examples given for peripheral nerve axons, above, similar principles of structure and function for components of neural structures, such as axons, cell bodies, dendrites, receptor endings, receptors, and synapses apply for different neural structures including peripheral nerve, a cranial nerve, a ganglion, and an autonomic nerve, a plexus, and a spinal cord. The sub-cellular structures within components of non-neural and neural tissue, such as cell membranes, lipid bilayers, ion channels, mitochondria, microtubules, nucleus, vacuoles, and other components of the cytoplasm are also related to the function of such components of neural structures.

As another example, the sphenopalatine ganglion consists of parasympathetic neurons, sympathetic neurons, and sensory neurons. Within the sympathetic ganglion, cell bodies and synapses are present for the parasympathetic neurons, but not for the sympathetic or sensory neurons. Rather, only axons of the sympathetic and sensory neurons pass through the sphenopalatine ganglion. The present device and method can be used to selectively and/or reversibly modulate nerve signal transmission in one of the neural structure types (e.g. cell bodies, synapses, axons) while not modulating the other neural structures present in the ganglion. For example, modulation or inhibition of transmission via the parasympathetic neuron pathway, for example by inhibiting transmission of signals via the cell bodies or synapses in the sphenopalatine ganglion, can be achieved while preserving signaling via the sympathetic pathways and at least some of the sensory pathways. As an additional example, modulation or inhibition of transmission via the small-diameter sensory neurons can be achieved while preserving signaling via the sympathetic, parasympathetic, and other sensory fiber pathways. As another example, modulation of the parasympathetic pathway and the small-diameter sensory pathway can be achieved while preserving signaling via all other pathways in the ganglion. Notably, each type of neural component within a neural structure can have its own unique supporting non-neural tissue which contributes to the ability to selectively target modulation via specific pathways As will be described in more detail below, the present device and method can be used to selectively modulate nerve signal transmission, for example by inhibiting (partially or completely) nerve signal transmission, to inhibit the perception of head-and-face pain. This inhibition of pain does not present risk of neural toxicity, vascular toxicity or injectable-chemical allergy. The present device is non-destructive of the target nervous structure and is suitable to treat chronic pain indications without the risks of atrophy, neuropathy and pain.

Example Device

FIG. 1 provides a schematic representation of an example electrical stimulation device 100. The electrical stimulation device 100 can be used to modulate a targeted neural- and non-neural tissue of a nervous structure with the transcutaneous application of an electrical signal to treat a medical condition of a patient. The stimulation device 100 comprises an electrode 120 that delivers electrical stimulation to the treatment site, e.g., delivers the electrical stimulation to the targeted neural and non-neural tissue of the nervous structure. The electrical stimulation can be delivered by a lead (L) and electrode 120 positioned adjacent an outer surface of the patient's skin near or overlying the targeted nervous structure (e.g., a cranial nerve).

The electrode 120 generates an electric field at the treatment site that results in selective and reversible modulation of the nerve fiber activity to inhibit the perception of pain. As provided above, the "modulation" of nerve fiber activity includes both the excitation and inhibition/interruption the passage of impulses along a neuron's axon within a nerve and can include inhibiting nerve signal transmission to the point of creating a blocking effect.

Figure 2:
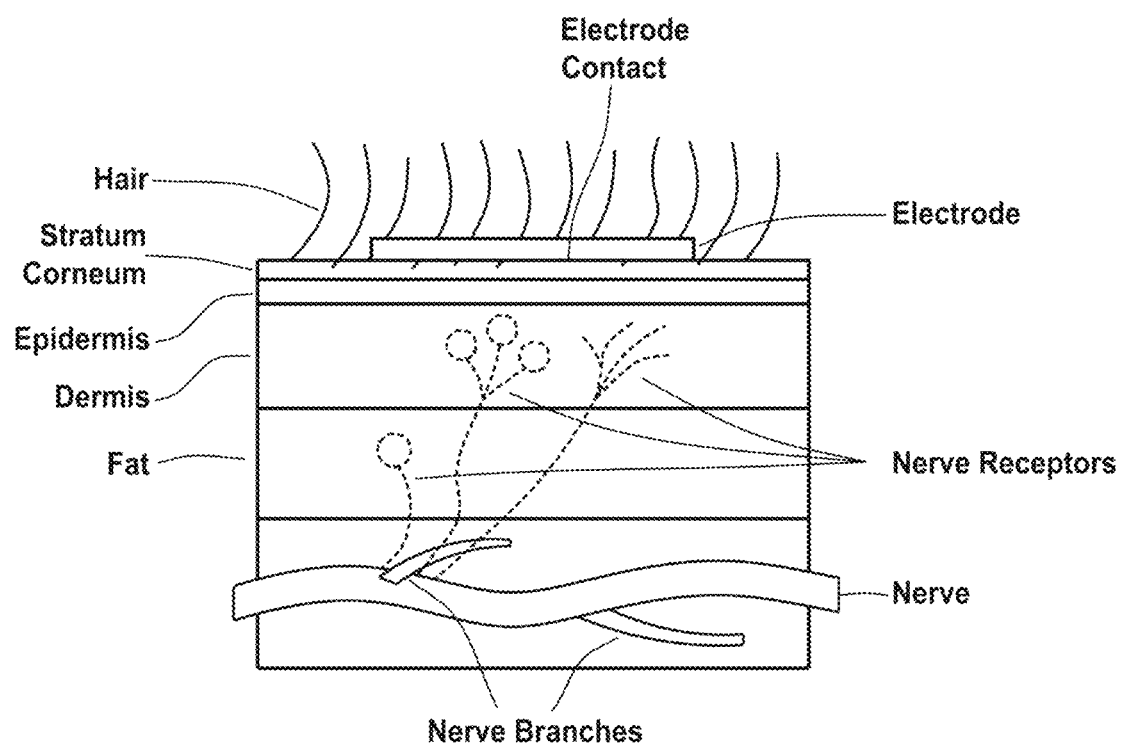
FIG. 2 is a schematic representation of patient anatomy and an example electrode for transcutaneously delivering electrical stimulation to a target nervous structure(s)
Figure 3:
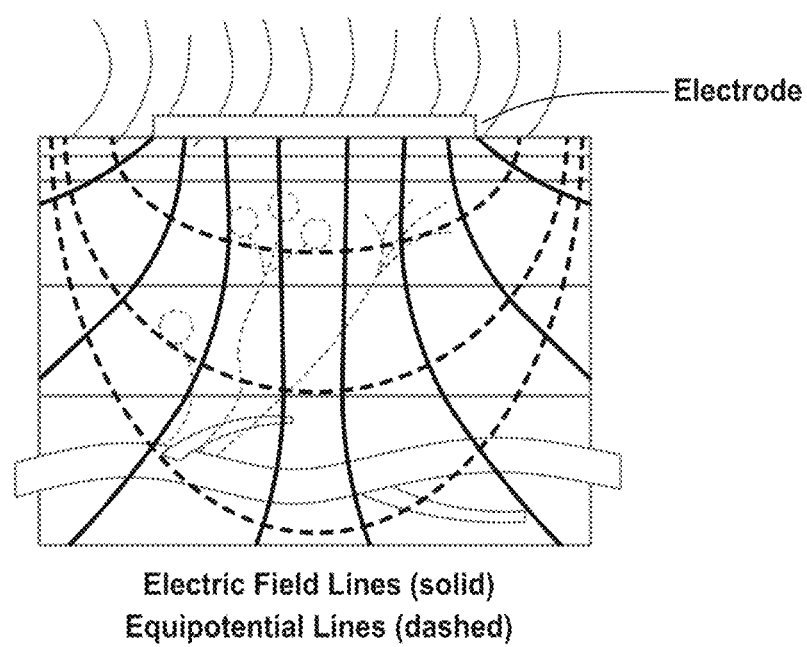
FIG. 3 is a schematic representation of patient anatomy and example electrical stimulation of FIG. 2.

The delivery of the electrical signal stimulation includes interactions with other nearby tissues. For example, in the case of transcutaneous application as illustrated in FIG. 2, the electrical signal stimulation is delivered via an electrode 120 positioned adjacent an outer surface of the patient's skin. The electrical stimulation must penetrate the skin and other tissues between the targeted nervous structure and the electrode 120 contact surface. In order to provide the electrical stimulation to the targeted nervous structure, the electrical stimulation must pass through the layers of the patient's skin and other tissues (e.g., underlying fat, as well as any intervening bone and muscle). In this example, the electrical stimulation influences not only the target neural structure, but also surrounding tissue such as connective tissue, supporting tissues of the nervous structure, fat, bone, muscle, and cardiovascular tissues and cells such as those present in and around blood vessels. In the case of a transcutaneous application, the electrical signal stimulation is delivered via the electrode 120 which is placed adjacent (e.g., near or in contact with) an outer surface of the patient's skin at a position overlying the targeted nervous structure. As illustrated in FIG. 3, the electrical stimulation generates an electric field in the tissues beneath and surrounding the electrode 120, including those tissues interposed between the electrode 120 and the target nervous structure, as well as other surrounding tissues (including skin, fat, muscle, bone, cartilage, connective tissue, supporting tissues of the nervous structure, cardiovascular tissues and cells such as those present in and around blood vessels, as well as other tissues present in the epidermis, dermis, as well as nerve receptors, hair follicles, sweat glands, sebaceous glands, apocrine glands, and lymphatic vessels). While application of the electrical stimulation to treatment site will modulate (e.g., selectively and/or reversibly, the targeted neural- and non-neural tissue of the nervous system structure to inhibit the perception of pain, the electrical stimulation and stimulation device 100 are designed such that no damage is caused to the nervous system structure and/or the surrounding tissue (e.g., the tissue interposed between the stimulation device/electrode 120 and the targeted nervous structure)). The electric field is titrated such that it produces the desired therapeutic effect in the desired target neural and non-neural tissues, without producing damage to the interposed tissues. Notably, the frequency of the electrical stimulation waveform influences the depth of penetration of the electrical stimulation waveform due to the lower impedance to current flow of the skin at higher frequencies. Thus, the inclusion of higher frequency components in the electrical stimulation waveform enables deeper penetration and deeper influence of the electrical stimulation waveform.

As schematically illustrated in FIG. 1, the stimulation device 100 and electrode 120/leads L may be either reusable or disposable. Desirably, the nervous structure can be modulated via a reusable lead L and electrode 120, and driven by a reusable external stimulator/signal generator 140 (e.g., an external function or waveform generator) and controller 130. The stimulator/signal generator 140 is coupled to both the electrode 120 and an interface of the controller 130, where operation of the stimulator/signal generator 140 is directed by the controller 130 to provide the electrical stimulation to the electrode 120. It is contemplated that the stimulation device 100, in its entirety, can be sized and configured for positioning adjacent an outer surface of the patient's skin (S) at a location adjacent the targeted nervous structure (N). The power source 180, providing electrical energy to the controller 130/signal generator 140 is likewise positioned external to the patient. It is also contemplated that stimulation device 100, including the leads/electrode 120, signal generator 140, and controller 130 can be embodied in a portable handheld or body-mounted device that can be easily manipulated to deliver the therapy by a patient or physician. It is further contemplated that the stimulation device 100, including signal generator 140, controller 130, leads (L), and electrode 120, may be embodied in a larger, non-handheld device designed to remain on a stationary surface or on a cart that can be moved between rooms at a medical clinic, where only the electrode 120/leads (L) are advanced into position adjacent the patient's skin (S). Accordingly, it is contemplated that the stimulation device 100 can be performed by a patient (e.g., at home) and as needed.

As described above, the stimulation device 100 can be used to treat head-and-face pain. As such, the targeted nervous structure would include nerves located on the head and neck. In one example, the targeted nervous structure can include cranial nerves such as the occipital nerves. FIG. 4 a schematic representation of the greater occipital nerve, lesser occipital nerve, and least occipital nerve (i.e. $3^{rd}$ occipital nerve) provided on a posterior view of the patient's head. Based on patient anatomy, the electrode 120 can be designed to ensure a sufficient electrical field is generated at the target occipital nerves to inhibit nervous signaling. FIG. 5 identifies example electrode locations A and B such that electrode A targets the greater, lesser, and least occipital nerves on both sides of the heath, while electrode B serves as a return path. FIG. 6 identifies example electrode sites C-H targeting each of the greater, lesser, and least occipital nerves on each side of the head. It should be appreciated that any of the electrodes A-H shown in these example figures could be used to deliver the electrical stimulation in a monopolar, bipolar, or multipolar fashion. It is contemplated that the focused area of the electrical stimulation is about 0.5 mm to about 10 mm in diameter and is projected from the electrode 120 to a location proximate the target nervous structure when the stimulation device 100 is located adjacent an outer surface of the patient's head or neck. The area of the electrical stimulation may be focused by providing a low-impedance pathway for the electricity to flow through the patient's skin adjacent the electrode. This can be accomplished, for example, by removing the top layer of dead skin cells (the stratum corneum) from the skin beneath the electrode and/or penetrating the outer layer of dead skin cells using, for example, small needles. The area of the electrical stimulation can also be focused by use of a waveform that penetrates more-easily through the skin. In a general sense, higher frequency waveforms travel through the skin more easily than lower frequency waveforms. Higher frequency waveform components penetrate deeper through the skin. In an example system, instead of a 10 kHz sine wave, the electrical stimulation is a 10 kHz sine wave with a 50-500 kHz waveform super-imposed on top. In another example, the electrical stimulation is delivered in bursts of a 50-500 kHz waveform such that the bursts occur at around 10 kHz.

Figure 7:
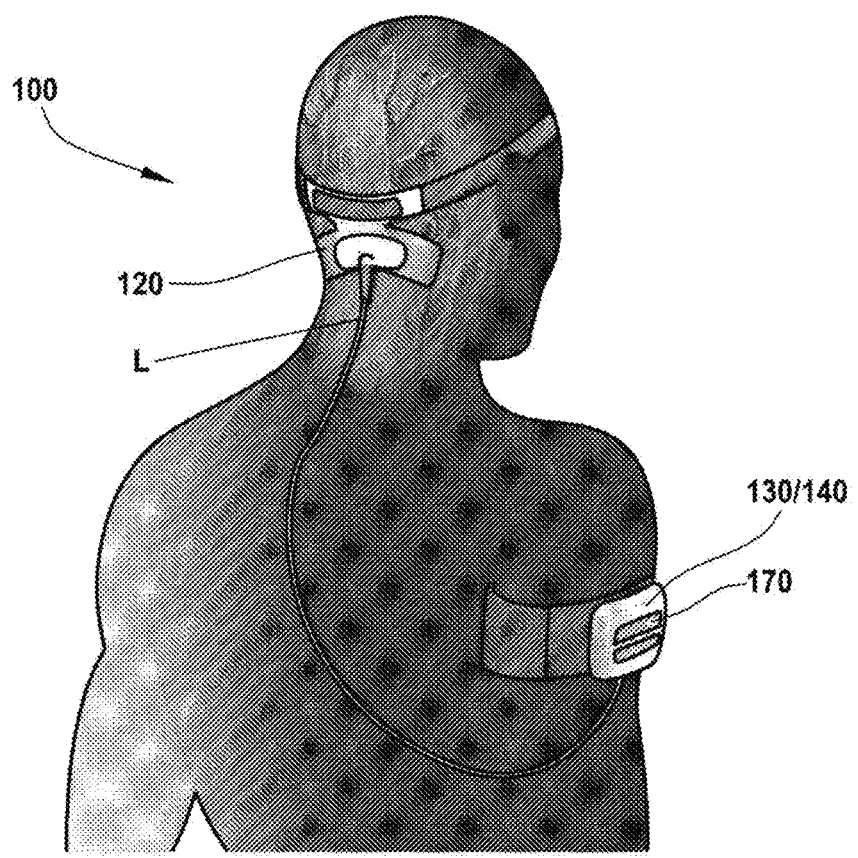
FIG. 7 is an example stimulation device positioned on the back of the patient's head.

FIG. 7 illustrates an example stimulation device 100 positioned on the back of the patient's head for targeting at least one of the greater occipital nerve, lesser occipital nerve, and least occipital nerve (i.e. 3rd occipital nerve). Though illustrated as a single stimulation device, it is contemplated that multiple stimulations devices 100 (e.g., multiple electrodes 120 driving by the same or different controllers 130) can be positioned at various positions on the patient's head, neck and shoulders. The electrode 120 can be provided in a housing having a contact surface that is positioned adjacent an outer surface of the patient's skin near the target nervous structure. The electrode 120 is located within the housing such that the electrical stimulation is projected toward the contact surface of the housing. In some examples, the electrode 120 is provided on the contact surface of the housing. The electrode 120 and/or housing is sized and configured for placement adjacent an outer surface of the patient's skin. For example, the contact surface of the electrode 120 and/or housing can include a curved surface to facilitate placement adjacent the patient's forehead, the base of the skull, along the patient's neck, or at any other portion of the patient's head, neck or shoulders. For example, the contact surface of the electrode 120 and/or housing can define a concave curved surface corresponding to the outer curvature of the patient's head and neck. It is contemplated that the electrode 120 and/or housing can be composed of a flexible material to allow the contact surface of the electrode 120/housing to conform to the shape of the patient's head/neck.

As provided in FIG. 7, the electrode 120 is positioned on the lower portion of the patient's skull proximate the greater, lesser and least occipital nerves. In this example, the contact surface of the electrode 120 and/or housing defines a shape and/or curvature corresponding to the shape of the occipital bone at the base of the patient's skull. The contact surface of the electrode 120 and/or housing can be designed to accommodate variances in patient anatomy with respect to patient anatomy (e.g., age, size) and the shape of the body near the targeted nervous structure. That is, the size and shape of the electrode 120 and/or housing can be varied depending on the age and/or size of the patient as well as the targeted nervous structure. For example, with respect use on an average-sized adult receiving treatment targeting the lesser occipital nerves, the electrode 120 and/or housing can have a width of at least about 17 cm such that the electrode 120 is wide enough to deliver electrical stimulation to the each of the patient's lesser occipital nerves. With respect use on an average-sized adult receiving treatment targeting the greater occipital nerves, the electrode 120 and/or housing can have a width of at least about 11 cm such that the electrode 120 is wide enough to deliver electrical stimulation to the each of the patient's greater occipital nerves. With respect use on a child or small adult receiving treatment targeting the lesser occipital nerves, the electrode 120 and/or housing can have a width of at least about 5 cm such that the electrode 120 is wide enough to deliver electrical stimulation to the each of the patient's lesser occipital nerves.

The electrode 120 housing and/or stimulation device 100 can be coupled to the patient such that the electrical stimulation can be administered without requiring the patient to hold or otherwise physically maintain the position of the electrode 120 (or stimulation device 100) during treatment. FIG. 7 illustrates the electrode 120 housing coupled to the patient using a strap that extends around the patient's head and forehead. It is also contemplated that the electrode 120 housing can be coupled to the patient using a strap, arms or cap that extend around other portions of the patient's head, neck and/or shoulders, using stems that hook around the patient's ears, using clip or comb-like structure that couples to the patient's hair, or any other mechanical or adhesive attachment means for removably coupling the electrode 120/stimulation device 100 to the patient's body.

The controller 130 can be provided in a housing that is shown coupled to the patient's arm via a strap or band. While illustrated in separate housings/components, it is contemplated that all of the components of the stimulation device 100 can be contained within the electrode 120 housing. For example, the electrode 120, controller 130 and signal generator 140 can be provided within the same housing and that is removably coupled to the patient during treatment (e.g., by a strap extending around the patient's head). The power source 180 and user interface 170 can also be included in the same housing and/or wired or wirelessly coupled to the controller 130.

Example Electrical Stimulation

As described above, the electrode 120 provides an electrical signal to the treatment site for selectively modulating the neural- and non-neural tissue, inhibiting nervous signaling. For example, the electrical stimulation signal disrupts the perception of pain by modulating both neural and non-neural tissue. For example, the electrical stimulation signal provided by the stimulation device 100 can modulate nerve signal transmissions through nerve fibers responsible for the transmission of pain while preserving nerve signal transmission through nerve fibers responsible for other sensory and motor function, and proprioception. The electrical stimulation can also be used to modulate the non-neural tissue adjacent the targeted nervous structure. The non-neural tissue can be modulated, for example, by reducing the blood flow to the pain-stimulating areas, reducing abnormal excitation of the peripheral pain fibers, modulating blood pressure, modulating vasodilation, modulating vasoconstriction, modulating glial cells, and/or modulating immune and inflammatory function.

As outlined below, various parameters of the electrical stimulation can be adjusted to modulate function of the nervous structure. For example, various parameters of the electrical stimulation can be adjusted to selectively inhibit transmission of nervous signaling in a select type of neural tissue of the target nervous structure and/or a downstream nervous structure, e.g., selective inhibition of nervous signaling in pain-transmitting nerve fibers, non-pain transmitting nerve fibers, sensory fibers, motor fibers, proprioceptive fibers, cell bodies, axons, myelinated nerve fibers, unmyelinated nerve fibers, large-diameter nerve fibers, and/or small-diameter nerve fibers. Adjustable parameters of the electrical stimulation include, for example, a stimulation-pulsed waveform shape (also referred to herein simply as "waveform shape"), a stimulation-pulsed frequency (also referred to herein simply as "frequency"), a stimulation-pulsed amplitude (also referred to herein simply as "amplitude"), an electrical field strength generated at the electrode 120 (e.g., measured at the electrode or at the treatment site), a stimulation-pulsed waveform DC offset, a waveform duty cycle (e.g., a continuous delivery, and/or intermittent delivery through the electrode), a tissue temperature (e.g., temperature of the a patient's skin adjacent the electrode contact surface), measured temperature (e.g., at the electrode 120 or a portion thereof, at the contact surface of the stimulation device, or a portion of cooling mechanism), a cooling mechanism parameter (e.g., a rate of cooling, flow rate of cooling medium, cooling medium pressure), and a treatment duration. It is contemplated that some parameters may be adjusted individually to produce a desired effect, while others are adjusted in combination with some interdependence on each parameters adjustment in an effect to produce the desired effect.

As described in more detail below, various parameters and/or combinations of parameters of the electrical signal are adjusted to selectively modulate nerve signal transmission through a select type of nerve fiber and/or through a select region of the nervous structure, to vary the duration of the inhibition of pain, the magnitude of the inhibition of pain, and/or delay the onset of pain inhibition. These parameters are adjustable and controllable by means of the controller 130, the patient or physician via the user interface 170, and/or a cooling mechanism that may be incorporated into the stimulation device 100.

In an example system, one or more parameters of the stimulation waveform can be adjusted to tune the duration of the inhibition pain. The stimulation device 100 can inhibit perception of head-and-face pain, for example by inhibiting or blocking pain for a period of about 1 day to about 30 days after the cessation of the stimulation. In another example, the pain perception is inhibited for a period of about 5 days to about 30 days after the cessation of the stimulation. The inhibition of nerve signal transmission can reduce an intensity of an episode of head-and-face pain, reduce a duration of an episode of head-and-face pain, reduce a frequency of episodes of head-and-face pain and/or prevent episodes of head-and-face pain. It is contemplated that the reduction in intensity, duration, frequency and/or prevention of head-and-face pain episodes can last for the duration of the delivery of the electrical stimulation, for the duration of the inhibition of nervous signaling, and/or for a prolonged duration after the cessation of such (e.g., 1 to 30 days, 1 to 5 days, up to about 8 hours to up to about 24 hours). Accordingly, one or more parameters of the stimulation waveform can be adjusted to reduce the intensity, duration and/or frequency of head-and-face pain episode. Similarly, one or more parameters of the stimulation waveform can be adjusted to tune the expected duration of pain inhibition and to ensure that pain inhibition does not last for longer than is desired. In one example, the duty cycle, pulse amplitude, and treatment duration can be adjusted to produce a desired duration and/or magnitude of the pain inhibition. In another example, controlling the temperature at the treatment site can be used to produce a desired selectivity of the modulation of nerve signal transmission.

While the duration of the pain inhibition can last for periods of days to weeks, it is also contemplated that the parameters of the stimulation waveform can be adjusted such that the patient can experience a decreased delay until onset of pain inhibition. That is, one or more parameters of the electrical stimulation can be adjusted to change the delay until onset of pain. For example, the onset of the inhibition of pain can be decreased from days down to minutes following the cessation of the electrical stimulation by adjustment of one or more parameters of the electrical stimulation.

The stimulation device 100 can selectively modulate the neural- and non-neural tissue inhibiting the perception of pain and preserving other sensory and motor function, and proprioception. This produces a scenario in which the electrical neuromodulation treatment is selective to a subset of functions of a nervous structure while preserving other functions of the nervous structure, e.g., pain perception is inhibited, while other sensory and motor function, and proprioception is preserved. For example, the electrical signal disrupts the transmission of pain signals that originate in the periphery from reaching the brain by inhibiting nerve signal transmission through nerve fibers that are responsible for the transmission of pain. This includes direct inhibition of transmission of pain signals in the neurons of the target neural structure, or can be achieved by indirect inhibition of other downstream neurons responsible for transmitting pain signals to the brain, such as neurons of the central nervous system (e.g. spinal cord and the brain).

Preserved sensory function includes, for example, non-painful touch sensation (low-threshold sensory function), vision, audition, gustation, olfaction, and balance. It is also contemplated that the disclosed electrical signal can modulate nerve signal transmission through nerve fibers responsible for the transmission of thermoreception, autonomic effector activity and visceral function.

Selective modulation of perception of pain is particularly useful in cases where the modulation is desired to be applied to mixed nervous structures, such as peripheral nerves containing motor and sensory axons. For example, in many interventions, it is desirable to modulate pain transmitted via mixed nerves to treat pain, while preserving motor and sensory and proprioceptive function of the nerve. Preservation of motor and sensory and proprioceptive function while treating pain is particularly important in cases where physical therapy or other movement of an appendage needs to be performed. For example, many care programs include steps to help patients avoid muscle atrophy or other stagnation of function. Preservation of motor control and sensory and proprioceptive function while treating pain can enable and enhance such programs.

It is contemplated that the electrical stimulation can selectively inhibit nervous signaling through at least one of a select type of neural tissue while selectively not inhibiting nervous signaling through an other select type neural tissue. Nervous signaling through the other not inhibited neural tissue can be preserved (e.g., no change) or increased. For example, the neural tissue selected for inhibition can comprise pain-transmitting nerve fibers such that that nervous signaling through pain-transmitting nerve fibers is inhibited, and the neural tissue selected for preservation comprises non-painful sensory nerve fibers, motor fibers, and/or proprioceptive fibers, such that that nervous signaling through non-painful sensory nerve fibers, motor fibers, and proprioceptive fibers is not inhibited. It is contemplated that the electrical stimulation can preferentially inhibit nervous signaling through the selected type of neural tissue such that the select type of neural tissue has a larger percentage inhibition of function than the non-selected type of neural tissue. It is further contemplated that the electrical stimulation can selectively inhibit nervous signaling through a select type of neural tissue while selectively activating nervous signaling through an other select type of neural tissue.

In another example, the neural tissue selected for inhibition comprises one of a cell body of a nervous structure (e.g., of the targeted nervous structure and/or of a downstream nervous structure) and axons of the nervous structure, such that nervous signaling through the cell body and/or the axons is inhibited. In this example, when nervous signaling through the cell body is inhibited, nervous signaling through the axons is no inhibited. Similarly, when the when nervous signaling through the axons is inhibited, nervous signally through the cell body is not inhibited.

In a further example, the neural tissue selected for inhibition comprises one of myelinated fibers of a nervous structure(s) (e.g., of the targeted nervous structure(s), of a downstream nervous structure) and unmyelinated fibers of the nervous structure, such that nervous signaling through one of the myelinated fibers and the unmyelinated fibers is inhibited. In this example, when the nervous signaling through the myelinated fibers is inhibited, nervous signaling through the unmyelinated fibers is not inhibited. Similarly, when the nervous signaling through the unmyelinated fibers is inhibited, nervous signaling through the myelinated fibers is not inhibited.

In another example, the neural tissue selected for inhibition comprises at least one of large-diameter nerve fibers of a nervous structure (e.g., the targeted nervous structure, a downstream nervous structure) and small-diameter nerve fibers of the nervous structure, such that nervous signaling through one of the large-diameter nerve fiber and the small-diameter nerve fiber is inhibited. In this example, when the nervous signaling through the large-diameter nerve fiber is inhibited, nervous signaling through the small-diameter nerve fiber is not inhibited. Similarly, when the nervous signaling through the small-diameter nerve fiber is inhibited, nervous signaling through the large-diameter nerve fiber is not inhibited.

In another example, the electrical stimulation can inhibit nerve signal transmission through the myelinated $A\delta$ fibers and/or the unmyelinated C fibers in the targeted peripheral nerve (or in a downstream nervous structure), where the electrical stimulation preserves nerve signal transmission through at least one of the $A\beta$ and $A\alpha$ fibers, and/or motor fibers. It is contemplated that at least one parameter of the electrical stimulation can be adjusted to selectively inhibit the myelinated $A\delta$ fibers and/or the unmyelinated C fibers, while preserving nerve signal transmission through at least one of the $A\beta$ and $A\alpha$ fibers, and/or motor fibers.

In another example, the targeted nervous structure covered by a layer of tissue, e.g., the gasserian ganglion, sphenopalatine ganglion (SPG), or other intervening tissue, e.g., skin, fat, muscle. The electrical stimulation can be delivered through the skin and/or intervening tissue to modulate nerve single transmission through a particular type of nerve fibers of the underlying nervous structure and adjacent non-neural tissue without causing damage to the skin/intervening tissue. Types of nerve fibers including, for example, parasympathetic nerve fibers, sympathetic nerve fibers, the sensory nerve fibers). For example, where the targeted nervous structure includes the sphenopalatine ganglion (SPG), the electrical stimulation selectively inhibits nerve signal transmission through the parasympathetic nerve fibers comprising the SPG, the sympathetic nerve fibers comprising the SPG, and/or the sensory nerve fibers comprising the SPG. It is contemplated that this nerve signal transmission can be inhibited while also selectively preserving function of at least one of the non-selected type of nerve fiber (e.g., parasympathetic, sympathetic, and sensory nerve fibers comprising the SPG).

It is further contemplated that at least one parameter of the electrical stimulation can be adjusted to differentially inhibit function of a select type of nerve fiber. For example, at least one parameter of the electrical stimulation can be adjusted to differentially inhibit nervous signaling in the myelinated $A\delta$ fibers of the target nervous structure such that the myelinated $A\delta$ fibers have a larger percentage of fibers inhibited than the unmyelinated C fibers. Nerve signal transmission through myelinated $A\delta$ is typically associated with the sensation of fast, sharp/stabbing pain, while nerve signal transmission through unmyelinated C fibers is typically associated with the sensation of dull/aching pain. Accordingly, the electrical stimulation can be adjusted to differentially inhibit the function of nerve fibers responsible for the sensation of sharp pain, such that those fibers have a larger percentage of fibers inhibited than nerve fibers responsible for the sensation of dull/aching pain Similarly, it is further contemplated that at least one parameter of the electrical stimulation can be adjusted to differentially inhibit function of the unmyelinated C fibers, such that the unmyelinated C fibers have a larger percentage of fibers inhibited than the myelinated $A\delta$ fibers. That is, the electrical stimulation can be adjusted to differentially inhibit the function of nerve fibers responsible for a sensation of dull/aching pain, such that those fibers have a larger percentage of fibers inhibited than nerve fibers responsible fora sensation of fast, sharp/stabbing pain.

In another example, where the targeted nervous structure covered by a layer of skin tissue, such as the gasserian ganglion or sphenopalatine ganglion (SPG), the electrical stimulation can be adjusted to differentially inhibit function of the parasympathetic, sympathetic, and/or sensory nerve fibers of the ganglion. For example, the electrical stimulation delivered to the target site can differentially inhibit the function of the parasympathetic nerve fibers of the SPG, where the parasympathetic nerve fibers have a larger percentage of fibers inhibited than non-parasympathetic nerve fibers and the non-neural tissue. Likewise, the electrical stimulation delivered to the target site can differentially inhibit the function of the sympathetic nerve fibers of the SPG, where the sympathetic nerve fibers have a larger percentage of fibers inhibited than non-sympathetic fibers and the non-neural tissue. Similarly, the electrical stimulation delivered to the treatment site can differentially inhibit function of the sensory nerve fibers of the SPG, where the sensory nerve fibers have a larger percentage of fibers inhibited that the parasympathetic, sympathetic and the non-neural tissue.

Figure 9:
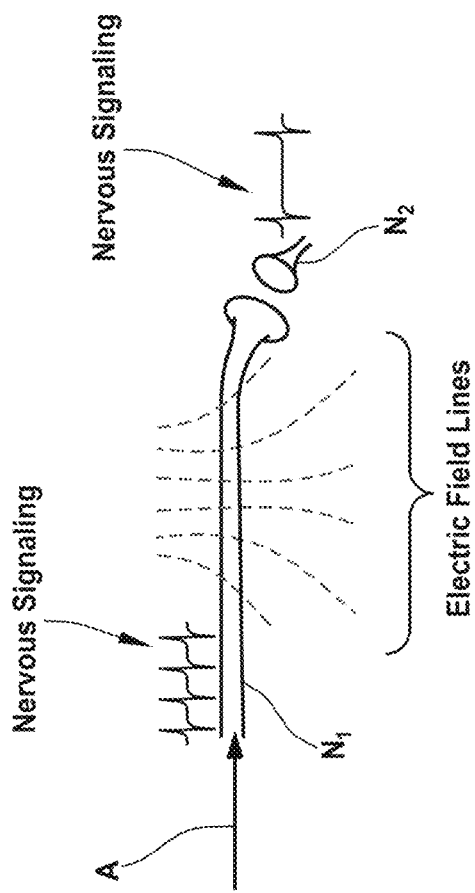
FIG. 9 is a schematic representation of inhibition of nervous signaling in a downstream nervous structure.
Figure 8:
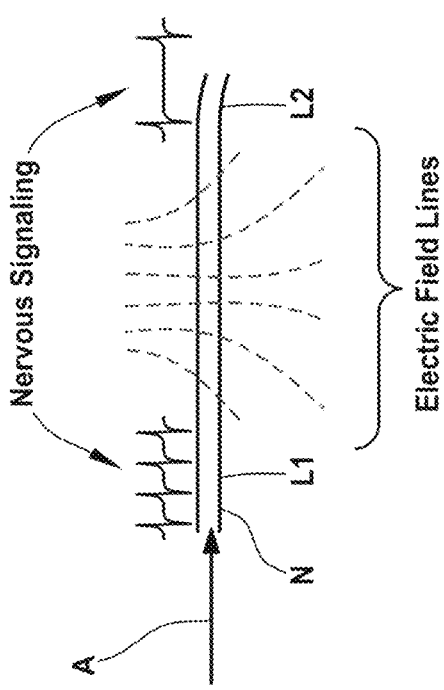
FIG. 8 is a schematic representation of direct inhibition of nervous signaling.

An additional mechanism of inhibition of perception of pain is when the inhibitory effect is downstream or secondary to the treatment site. That is, the application of the electrical stimulation can result in the inhibition of nervous signaling in the targeted nervous structure and/or a downstream nervous structure. FIGS. 8 and 9 schematically illustrate examples of inhibition of nervous signaling. FIG. 8 provides an example in which direct inhibition of nervous signaling is produced in a target nervous structure (N) by application of the stimulation waveform. In this example, the target nervous structure (N) is shown as an axon. The electric field lines illustrate the electric field generated in the tissue by the electrical stimulation signal. Application of the electrical stimulation to the nervous structure (N) results in the inhibition of the nervous signaling traveling in the direction of arrow A. For example, application of electrical stimulation can show a decrease in the frequency of the nervous signally between location L1 and L2 along a length of the axon, where the electrical stimulation is applied a location between L1 and L2. FIG. 9 provides an example in which inhibition of nervous signaling is produced in a nervous structure that is not the target nervous structure (e.g. a downstream nervous structure). In this example, the electrical stimulation is provided to the nervous structure ($N_1$) and the resulting inhibition of nervous signaling occurs in a downstream nervous structure ($N_2$).

In an example where the targeted nervous structure is a peripheral nerve, the electrical stimulation can modulate activity or function of neural or non-neural tissues which results in activation of a bio-chemical signaling cascade which causes a decrease in activation of spinal or cortical neurons representing pain (for example, via modulation of synaptic signaling). In an example system, the frequency and/or amplitude of the electrical stimulation produce an inhibition of the action potential conduction in the nerve fibers of the targeted nervous structure/downstream nervous structure.

In the case of a large peripheral nerve, it is contemplated that at least one parameter of the electrical stimulation can be adjusted to selectively inhibit downstream or secondary effects of pain originating from Aδ fibers and/or originating from the unmyelinated C fibers, while the function of central nervous system and peripheral nervous system neurons involved in detection, transmission, processing, and generation of non-painful touch, motor control, and proprioception are preserved. It is further contemplated in this case that at least one parameter of the electrical stimulation can be adjusted to differentially inhibit downstream or secondary effects of pain originating from myelinated Aδ fibers such that the downstream or secondary effects from myelinated Aδ fibers are inhibited to a greater extent than the downstream or secondary effects from unmyelinated C fibers. Similarly, it is further contemplated in this case that at least one parameter of the electrical stimulation can be adjusted to differentially inhibit downstream or secondary effects of pain originating from unmyelinated C fibers, such that the downstream or secondary effects from unmyelinated C fibers are inhibited to a greater extent than the downstream or secondary effects from myelinated Aδ fibers.

To facilitate the selective and/or reversible inhibition of nervous system activities, the stimulation device and system is configured, in some embodiments, to apply a high frequency stimulation to the nerve and/or to nearby tissue to invoke sufficient pain inhibition response by the nervous system. The high-frequency stimulation may be applied in pulses over the course of a single treatment/application and in a manner so as to avoid damaging nearby tissue and nerve tissue. For example, it has been observed that a high-frequency stimulation applied at 5-20 kHz at up to 60 mA for a few minutes can be applied to invoke an inhibition of nervous signaling. It has also been observed that the same high-frequency stimulation can be applied to invoke a reversible inhibition response in that signaling is blocked for a duration longer than the duration of the electrical stimulation. See, e.g., FIGS. 20A-20C.

Figure 10A:
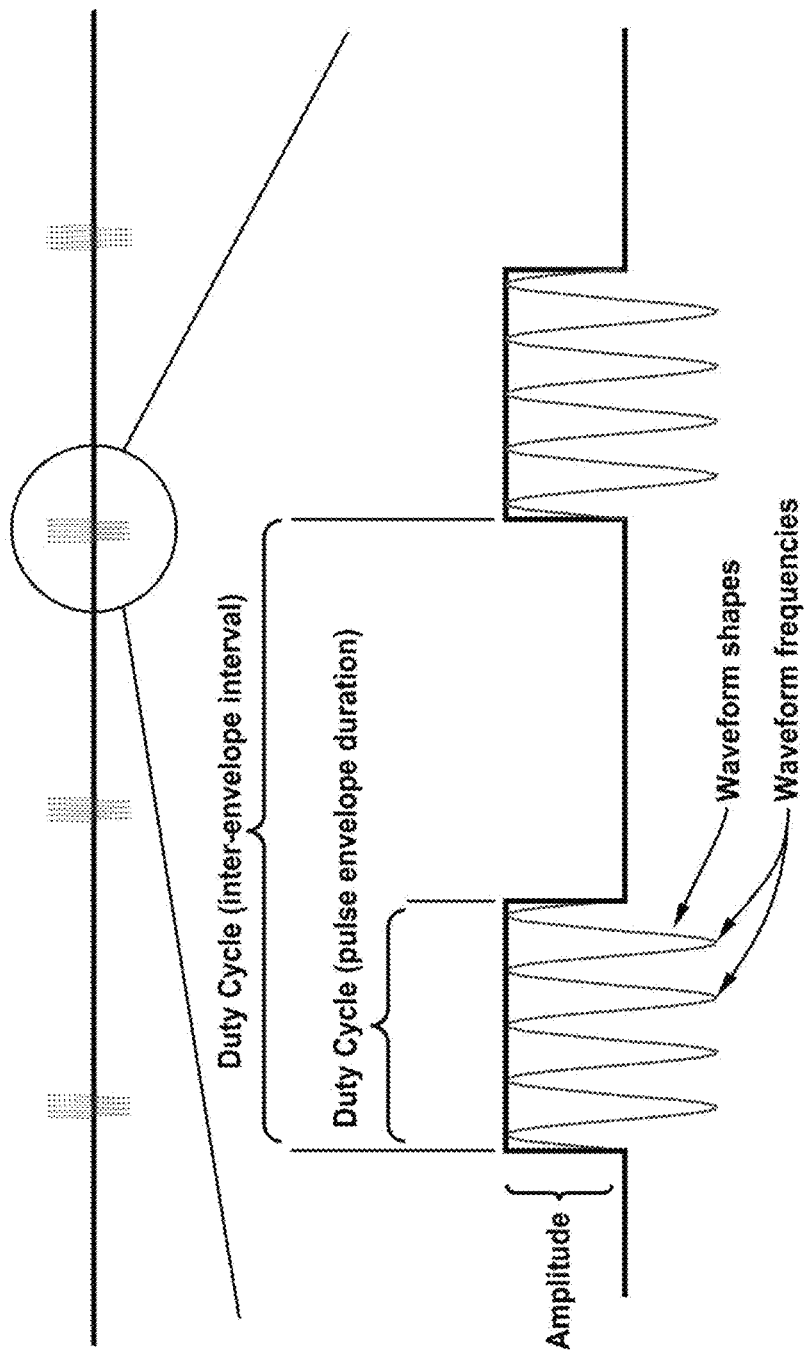
FIG. 10A is an example electrical stimulation, and corresponding control parameters, that can be applied to the nerve and/or nearby tissue to selectively inhibit nervous system function.
Figure 10N:
Figure 10O:
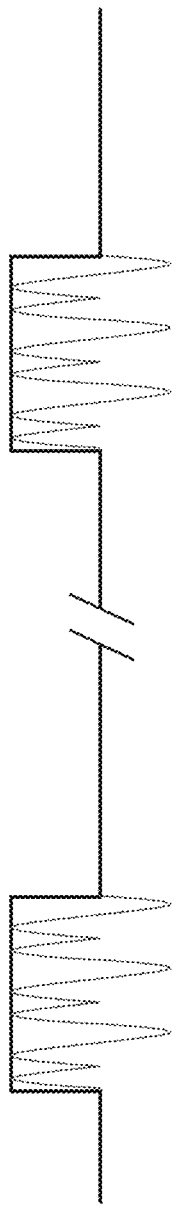
Figure 10P:
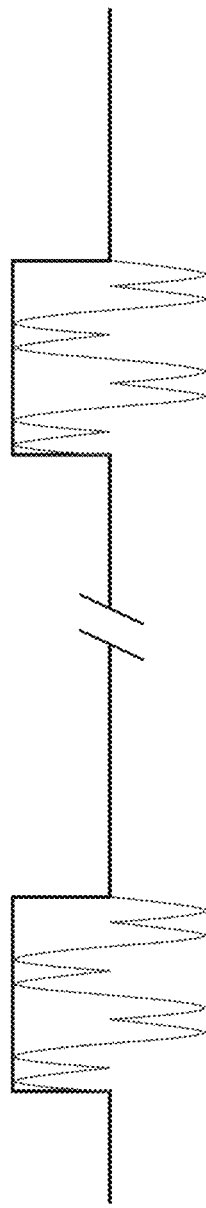

FIG. 10A shows an example electrical stimulation, and corresponding control parameters, that can be applied to the nerve and/or nearby tissue to inhibit nervous system activities, in accordance with an illustrative embodiment. As shown in FIG. 10A, the electrical stimulation can be defined via control parameters such as amplitude, pulse duty cycle (e.g., comprising a pulse envelope duration and an inter-envelope interval), stimulation waveform shape, and waveform frequency. In addition to a stimulation frequency of about 2 kHz to about 500 kHz, other stimulation frequency ranges can be applied. In some embodiments, the stimulation device 100 is configured to apply an electrical stimulation having a stimulation frequency selected from the group consisting of about 2 kHz, 25 kHz, 50 kHz, 75 kHz, about 100 kHz, about 150 kHz, about 200 kHz, about 250 kHz, about 300 kHz, about 350 kHz, about 400 kHz, about 450 kHz, and about 500 kHz. The frequency of the stimulation is an important factor that assists in inhibition of nervous signaling. For example, higher frequency components (e.g. >2 kHz) enable blocking of nervous signaling. Additionally, the impedance of the skin to flow of electrical current is lower for higher frequency signals, producing a desire to include higher-frequency components in the stimulation waveform to facilitate delivery through the skin.

Application of an electrical stimulation having a pulse duty cycle can allow for a higher voltage or current amplitude to be outputted and/or higher frequency (to allow for higher voltage field to be generated at the treatment site) while not causing thermal damage at the tissue. Application of an electrical stimulation having a non-sinusoidal waveform can be used to adjust the energy density that is applied in a given electrical stimulation and/or also allowing for higher electrical field to be applied.

FIGS. 10B, 10C, 10D, 10E, 10F, 10G, 10H, 10I, 10J, 10K, 10L, 10M, 10N, 10O, and 10P each shows a waveform shape for an electrical stimulation, in accordance with an illustrative embodiment. As shown in FIGS. 10B-10F, in some embodiments, the stimulation waveform is a sinusoidal waveform (FIGS. 10B, 10G), a triangular waveform (FIG. 10C), a square or rectangular waveform (FIG. 10D), a triangular saw-tooth waveform (FIG. 10E), or a complex waveform (FIG. 10F).

In some embodiments, the frequency of a given pulse is varied (e.g., as a chirp, as shown in FIGS. 10K, 10L, and 10M). In some embodiments, the amplitude envelope of the electrical stimulation is varied for a given pulse (FIGS. 10K and 10L).

In some embodiments, the electrical stimulation is a voltage-controlled output. In some embodiments, the electrical stimulation is a current controlled output. In some embodiments, the electrical stimulation is a power-controlled output.

In some embodiments, the stimulation waveform shape comprises a continuous charge-balanced shape (see, e.g., FIGS. 10B-10F, 10K, 10L, 10M, 10N, and 10P), or an additive combination of sinusoids (e.g., as a sine function (see FIGS. 10N, 10O, and 10P)).

The illustrated waveforms are merely illustrative. It is contemplated that other type of waveforms shapes can be generated such as impulses or other shapes. In some embodiments, the stimulation waveform comprises a single pulse having a duration of 1 µs to 10 µs.

Other parameters of the electrical stimulation can be controlled (e.g., by and/or in response to feedback mechanisms) such as electric field strength at the electrode, DC offset, tissue temperature, cooling mechanism parameter, and treatment duration. In some embodiments, the stimulation device and/or system is configured to control the electrical stimulation based on an observed or measured temporal and/or spatial derivatives of voltage, current, power, and temperature (e.g., the rate-of-change of temperature over time). In some embodiments, two or more of current-controlled stimulation, voltage-controlled stimulation, power-controlled stimulation, and temperature-controlled stimulation can be executed in combination to deliver to the targeted neural- and non-neural tissue of the nervous structure. The parameters of amplitude, waveform shape, frequency, DC offset, duty cycle and duration can be tuned for such current-controlled stimulation, voltage-controlled stimulation, power-controlled stimulation, and/or temperature-controlled stimulation, or a combination thereof.

Indeed, the stimulation parameters can be optimized to selectively inhibit perception of pain while preserving nerve activity responsible for motor activity, low-threshold sensory function, and proprioception. For example, the stimulation parameters can be optimized to attenuate or abolish activity in myelinated Aδ and unmyelinated C fibers while preserving (e.g., without attenuating) nerve activity in the nerve fibers responsible for motor activity, low-threshold sensory function, or proprioception.

In addition to selectively treating different fiber types, at least one parameter of the of the electrical stimulation/stimulation waveform and induced electrical field can be adjusted to preferentially or optimally modulate nerve signal transmission within a desired region of a nervous structure, where the desired region of the nervous structure is a portion of the nervous structure less than its complete cross-section (e.g., adjusting parameters of the electrical stimulation to affect specific regions of a nerve vs. affecting the complete nerve cross-section). The stimulation waveform can also include parameter changes which influence and reduce onset response (in the target nervous structure or a downstream nervous structure) without producing activation of other nervous activity including nociceptive activity, motor activity, sensory activity, autonomic activity, or enteric activity (e.g., a pulsing sensation at the nervous structure, motor response in a muscle adjacent the target nerve such as muscle spasm or twitching) and activation of nerve tissue at the onset of stimulation at either the beginning of the continuous waveform or at the onset of each burst of stimulation during intermittent stimulation. In an example system, to reduce undesired activation of excitable tissues at the onset of stimulation or at the onset of a burst of stimulation the amplitude of the stimulation waveform is increased from initial amplitude level to a final amplitude level over the duration of about 1 sec to about 5 mins at the onset of stimulation or at the onset of a burst of stimulation.

The parameters of the stimulation waveform may also be tuned to control the duration and time-course of pain inhibition that will be achieved after the treatment and to ensure that adequate pain inhibition is achieved with a treatment.

The parameters of the stimulation waveform may be adjusted to enable treatment of larger nerves (for example, with a diameter greater than about 2.5 mm) and larger nervous structures or nervous structures with different shapes, sizes, and neural and non-neural tissue composition, for example by increasing the amplitude or adjusting other parameters of the stimulation waveform which result in an increase in the spatial size and shape electric field. Some nervous structures, such as some ganglia or plexuses, are large by nature and treatment of these large structures is enabled by adjustment of the waveform parameters.

The parameters of the stimulation waveform may also be adjusted to enable non-damaging treatment and inhibition of pain. Hardware and software may also be included to control the amount of DC current delivered concurrently with the waveform. The controller 130 may include, for example, a current controller or a voltage controller for adjusting the amount of DC current or voltage delivered concurrently with the electrical signal.

As mentioned above, the device and method of the present invention, including the parameters of the waveform and adjustment thereof, can inhibit pain (such as migraines or other head-and-face pain) for a period of days-to-weeks post-infection/procedure. However, it is also to be understood that the device and method of the present invention, including the parameters of the waveform and adjustment thereof, can also be used to provide therapeutic treatment for other chronic pain conditions as well as for acute pain. The therapeutic treatment for chronic pain may include ongoing preventative delivery of signals, or abortive, on-demand delivery when episodes of chronic pain are experienced.

Compared to other methods of modulating activity of a nervous structure using an electrical signal, the system and method of the present disclosure is able to provide non-invasive inhibition of nervous signaling. Other treatment modalities require either activation of nerves or delivery by a healthcare professional. For example, percutaneously applied pulsed radiofrequency, frequently used to treat pain in small nerves, utilizes intermittent pulses of a 45 V radiofrequency signal to stimulate the target nerve. Pulsing is used in this case to avoid temperatures at the treatment site that would damage or destroy the nerve tissue. However, pulsed radiofrequency must be delivered in close proximity to the nerve in order to produce a therapeutic effect, and thus has not been successfully enabled for non-invasive, transcutaneous delivery. In contrast, the stimulation parameters of the present disclosure allow for the application of a high voltage, high frequency waveform that does not have the temperature limitations associated with a pulsed RF signal and as a result can safely be applied transcutaneously without risk of damaging tissue interposed between the electrode and the target nervous structure. Adjustment of the parameters of the stimulation waveform enables control of the application of the electric signal to ensure that adequate pain inhibition is achieved while avoiding tissue damage.

For example, a system can be configured to deliver the electrical signal (also referred to herein as "electrical stimulation") to the treatment site with a frequency range between of about 1 kHz to about 500 kHz, between about 2 kHz to about 400 kHz, between about 3 kHz to about 300 kHz, between about 4 kHz to about 350 kHz, or between about 5 kHz to about 200 kHz. In an example system, the electrical stimulation is not more than 500 kHz. In an example system, the electrical stimulation delivered to the treatment site is at least 5 kHz. The electrical signal delivered to the treatment site has an amplitude range between about 1 mA (peak-to-center, corresponding to 2 mA peak-to-peak) and about 200 mA (peak-to-center, corresponding to 400 mA peak-to-peak). In an example system, the electrical signal has an amplitude ranging between about 1 mA and 50 mA, between about 50 mA and 100 mA, between about 100 mA and 150 mA, or between about 150 mA and 200 mA. The electrical signal delivered to the treatment site has an amplitude between about 1 V (peak-to-center, corresponding to 2 V peak-to-peak) and about 2000 V (peak-to-center, corresponding to 4000 V peak-to-peak). In an example system, the electrical signal has a peak-to-peak amplitude ranging between about 1V and about 50 V, about 50 V and about 100 V, about 100 V and about 200 V, about 200 V and about 300 V, about 300 V and about 400 V, or about 400 V and about 500 V. In an example system, the electrical stimulation delivered to the treatment site has a peak-to-peak power ranging between about 20 W and about 800 W.

The electrical signal delivered to the treatment site has a waveform shape component such as a continuously outputted waveform or an intermittently outputted waveform at a duty cycle (e.g., pulsed for a predefined duration). The waveform shape component can include a sinusoidal shaped waveform, a square shaped waveform, a triangular shaped waveform, a shape-modulated waveform, a stochastic noise waveform, a frequency-modulated waveform, an impulse waveform (e.g., an amplitude-modulated waveform that provides a continuous delivery of electrical stimulation at the treatment site, or an impulse-shaped waveform), and/or additive combinations thereof. An example of a frequency-modulated waveform is a chirp. An example of an amplitude-modulated waveform is a wavelet. In another example system, the electrical signal delivered to the treatment site has an arbitrary waveform. In another example system the electrical signal can have a combination of the waveforms mentioned previously. Repeated delivery of the waveform is implied in which a waveform shape is delivered in repeated fashion at a specified repetition frequency. The waveform of the electrical signal can be delivered continuously or intermittently. Continuous delivery implies that the waveform is delivered at a specified waveform frequency continuously, without breaks. Intermittent delivery implies that the waveform is delivered at a specified waveform frequency during envelopes of time that are separated by breaks during which no stimulation is delivered. For continuous delivery, the duty cycle is 100% (for example, via chirp function). For intermittent delivery, the duty cycle ranges from about 0.1% to about 99%. The term duty cycle refers to a period that the pulse is on having multiple oscillations with a predefined frequency. For intermittent delivery, the electrical signal has an inter-envelope width of about 0.01 ms to about 60 s, where the inter-envelope width is defined as the duration of time between then end of an envelope and the start of the next envelope. In one example, the electrical signal has a 0.01 ms pulse width delivered at 50 kHz. In another example of intermittent delivery, the electrical signal comprises bursts of waveform shapes having a duration of about 0.01 ms to about 1000 ms, a burst frequency from about 0.01 Hz to about 50 Hz, or an inter-burst width of about 0.01 ms to about 60 s.

During an example treatment, the electrical signal is delivered for a treatment duration of up to 8 hours, preferably 30 minutes. In an example system, the electrical signal is delivered for treatment duration of 1 minute, 1 minute to 5 minutes, 5 minutes to 10 minutes, 10 minutes to 15 minutes, 15 minutes to 20 minutes, 20 minutes to 25 minutes, or 25 minutes to 30 minutes.

As described below, the controller 130 is adjustable to apply the electrical stimulation while maintaining the tissue temperature between about 5° C. and about 45° C. That is, the electrical signal can have a tissue temperature that has an amplitude between about 5° C. and about 45° C.

The electrical signal delivered to the treatment site may be current controlled, voltage controlled, power controlled and/or temperature controlled. The electrical signal comprises a continuous charge-balanced waveform, a biphasic waveform or impulse, or additive combination thereof. Alternatively, the electrical signal comprises a not charged-balanced waveform or impulse, or additive combination thereof.

The strength of the electrical field generated at the target site is greater than 10 kV/m. The electrical stimulation delivered to the treatment site generates or induces an electrical field strength at the target site and/or the one or more electrodes between about 20 kV/m and about 2,000 kV/m. The electrical field generated at the target site ranges between 20 kV/m to 2,000 kV/m at its temporal peak, 25 kV/m to 500 kV/m, or 50 kV/m to 400 kV/m. In a transcutaneous application, the electrical stimulation generates or induces an electrical field strength at the target site and/or the electrode preferably between about 20 V/m and about 1,000,000 V/m. The strength of the electrical field varies as a function of distance from the electrode, shape of the electrode, and other factors such as the conductivity of the different tissues near the electrode. Tuning of waveform parameters of the stimulation waveform enables control of the spatiotemporal electrical field within the tissue and at the interface of the electrode with the tissue. Tuning of the waveform parameters of the stimulation waveform also enables control of the spatiotemporal thermal field within the tissue and at the interface of the electrode with the tissue. The spatiotemporal variations and levels of the electrical field and the thermal field are important factors in producing the desired selective, reversible inhibition of pain in the target neural structures. Additionally, a cooling mechanism, as will be discussed in detail below, implemented in concert with the waveform and other aspects of the stimulation such as the electrode, enables control and reduction of the spatiotemporal thermal field independent or semi-independent from the electrical field. Separation of these two important variables ultimately enables delivery of a selective, reversible, and tunable treatment that is nondamaging to the neural tissue and adjacent non-neural tissue.

Example Cooling Mechanism

It is also contemplated that the stimulation device 100 can include a cooling mechanism to prevent damage to the patient's tissue during delivery of the electrical stimulation. The cooling mechanism can be integral with the electrode 120 and/or a separate component from the electrode 120 that is coupled to the electrode or positioned at the treatment site separate from the electrode 120. The cooling mechanism can be controlled by the controller 130 or include a separate controller for directing its operation. The cooling mechanism is used to provide a cooling effect at the treatment site (e.g., at the contact surface of the stimulation device 100 and/or contact surface of the electrode 120 and/or within the tissue near the treatment site). The cooling effect preserves the temperature of the patient's tissue (e.g., the patient's skin adjacent the contact surface of the stimulation device, the patient's tissue interposed between the contact surface of the stimulation deice device and the targeted nervous system structure, tissue overlying the nervous system structure (e.g., skin, mucosal tissue)) below a threshold destructive tissue temperature.

It is appreciated by those skilled in the art that delivery of electrical stimulation waveforms to tissue can result in heating of the tissue adjacent the delivery electrode 120 and/or contact surface of the electrode housing. When heating of the tissue is excessive, thermal damage to the tissue can be created. One objective of the present invention is to produce selective and reversible inhibition of nervous signaling while and not damaging the tissue interposed between the electrode 120 and/or contact surface of the electrode housing and the target nervous structure. Thermal lesions of tissue have been deliberately used to ablate or inhibit transmission of nerve action potentials, however, these approaches have not been used transcutaneously. Additionally, cooling of tissue has been used with thermal ablations, for example with cooled radiofrequency ablations, to enable an increase in power dissipation in the tissue, allowing for an increase in the power of an RF waveform and creation of a larger thermal lesion. However, these cooled RF approaches aim to raise the tissue temperature to at least 60-90° C. for several seconds to minutes in order to create a thermal lesion in the tissue. In contrast, the present disclosure contemplates use of a cooling mechanism that will preserve tissue interposed between the electrode 120 and the nervous structure below thermal damage levels while enabling delivery of an electrical signal that can result in inhibition of nervous signaling.

The cooling mechanism creates a cooling effect that prevents damage to the patient's tissue when the electrical stimulation is delivered by preserving temperatures of the patient's tissue below a destructive tissue temperature, e.g., below temperatures likely to cause thermal damage to the tissue (for example avoiding temperatures that rise above 45° C. for a period of multiple seconds). The cooling mechanism preserves temperature of the treatment site by pre-cooling the treatment site and/or maintaining the temperature of the treatment site within a desired (non-destructive) range during delivery of the electrical stimulation. The cooling mechanism maintains the temperature of the contact surface of the stimulation device 100/electrode housing and/or electrode 120 below a destructive tissue temperature in response to feedback information received from the electrode 120 and/or input from the patient and/or operator. The feedback information includes the measured temperature data received from a temperature sensor 210 (e.g., thermistor, thermocouple) coupled to the stimulation device 100, for example, on a contact surface of the electrode housing/stimulation device. The temperature sensor 210 can measure the temperature of the contact surface of the electrode 120 and/or the temperature of the patient's tissue adjacent the contact surface of the electrode 120/electrode housing. The temperature sensor 210 is electrically coupled to the controller 130 and provides thermal feedback information regarding the measured temperature (e.g., at the treatment site, at the electrode 120 or a portion thereof, at the electrical stimulation device/electrode housing, at the patient's skin, or at some portion of the cooling mechanism). As described below, in response to the temperature feedback information, operation of the cooling mechanism and/or parameters of the electrical stimulation can be adjusted (e.g., by the controller 130 or the user) to control the temperature at the contact surface of the electrode 120, thereby reducing the temperature of the adjacent patient tissue (e.g., tissue comprising and surrounding the target nervous structure) to a temperature below a destructive tissue temperature or maintain the contact surface of the stimulation device/electrode housing and surrounding tissue at a temperature between about 5° C. and about 60° C.

Figures 11A, 11B:
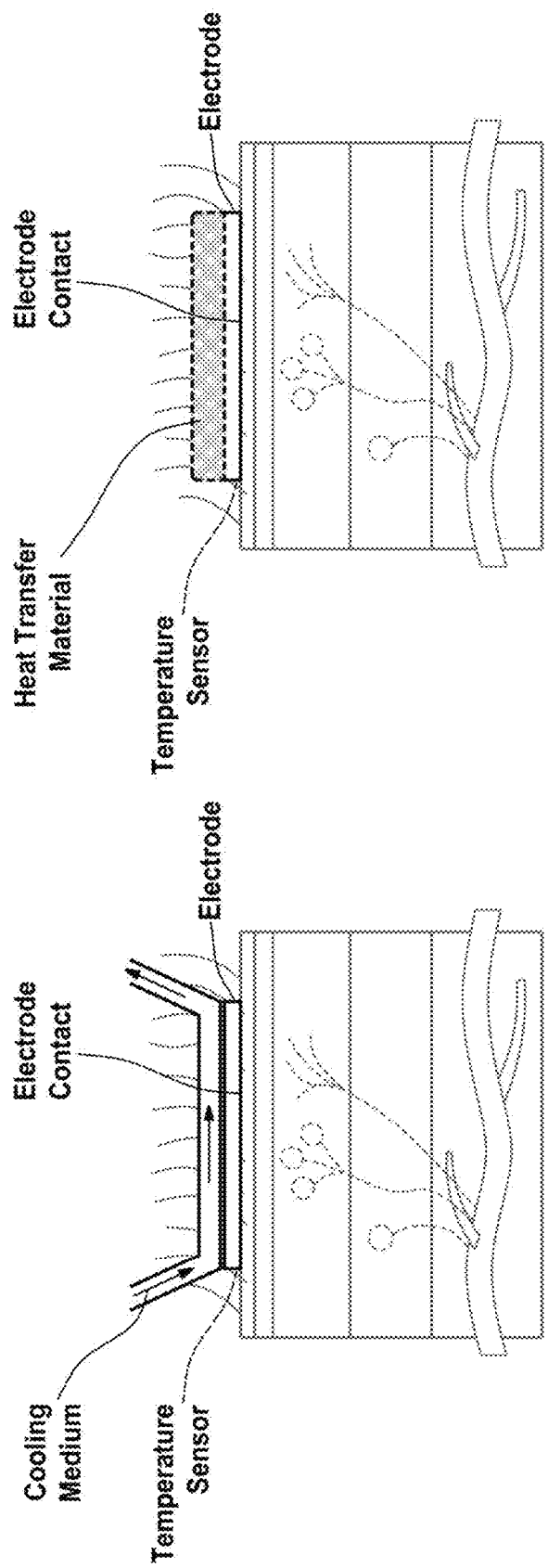
FIGS. 11A and 11B are schematic illustrations of patient anatomy and an example electrode including a cooling mechanism.

In one example, illustrated in FIG. 11A, the cooling mechanism may comprise a pump which circulates a cooling medium such as a gas or pressurized fluid (e.g., carbon dioxide, nitrogen, water, propylene glycol, ethylene glycol, salt water, or mixtures thereof) through the electrode 120 via the conduits 160 provided in the leads (L) (see FIG. 1). As illustrated in FIG. 11A, the cooling medium can be circulated along the outside surface of the electrode 120. The circulated gas/fluid serves to remove heat from the electrode 120, tissue of the treatment site and the neighboring tissues. This gas/fluid may be delivered at room temperature or may be cooled below room temperature by use of an incorporated gas/fluid cooling unit or by use of ice or other cooling mechanisms. The cooling of the gas/fluid may be performed before treatment and during treatment. A thermally insulating coating or sheath may also be incorporated around the leads (L) to prevent heating of the cooling medium by heat transfer to the ambient environment.

In another example, illustrated in FIG. 11B, the cooling mechanism includes a heat transfer material provided in contact with the tissue of the treatment site and/or the electrode 120. The heat transfer material can be disposed on/within the electrode 120/leads (L), on a contact surface of the electrode housing and/or on an introducer. The heat transfer material acts as a heat sink removing heat from the electrode 120, the tissue of the treatment site and the neighboring tissue. The heat transfer material can include a fin-, rib- or pin-shaped contact surface for increasing the surface area of the electrode 120 and expediting heat transfer from the electrode 120 and the environment. The heat transfer material can also include a thermally conductive material (e.g., metal, ceramic material, conductive polymer) and/or one or more Peltier circuits. The thermally conductive material can also include a phase change material that can change phase at a temperature between about 40° C. and 100° C. An example phase change material includes a paraffin wax provided in a pathway that extends from the electrode 120/electrode housing contact surface to the ambient air. Heat exchange between the paraffin wax and the ambient air serves to remove heat from the electrode 120/treatment site and the neighboring tissues. Additional exemplary cooling mechanisms are described in U.S. Application No. 62/403,876, filed Oct. 4, 2016, entitled "Cooled RF Probes," incorporated herein by reference.

In addition to preventing damage to tissue, the cooling mechanism enables selective inhibition of pain. For example, non-selective inhibition of pain, where motor or non-painful sensory or proprioceptive function is also inhibited, can be observed when temperatures are not preserved below a desired threshold (such as above 45° C. for a period of multiple seconds). Preservation of the target tissue below such a thermal threshold temperature by use of a cooling mechanism enables selective inhibition of pain without modulating or inhibiting other functions of the nervous structure. Thus, the temperature of the electrode and the tissue is an important parameter that can be tuned by means of the cooling mechanism to enable selectivity of inhibition of pain.

Use of the cooling mechanism also enables treatment of nervous structures of various shapes, sizes, and compositions. For example, the size of the spatial electric field generated by the electrical waveform in the tissue may need to be increased in order to encompass larger nervous structures such as large peripheral nerves, cranial nerves, ganglia, autonomic nerves, portions of the spinal cord, and plexuses. One method for increasing the size of the spatial electric field is to increase the amplitude of the electrical waveform. Use of the cooling mechanism enables an electrical waveform to be delivered with higher amplitude while maintaining the tissue at thermal levels that avoid thermal damage. For example, when peripheral nerves with a diameter greater than 2.5 mm are treated by the stimulation device 100, use of the cooling mechanism enables the electrical waveform parameters, including the amplitude, to be adjusted to levels high enough to treat the larger nerve target without producing thermal damage to the nervous structure. In another example, the nervous structure, such as ganglia (e.g., gasserian ganglion, sphenopalatine ganglion (SPG)), may be composed of and surrounded by various tissues with different thermal and electrical conductivities. In this case, the cooling mechanism enables delivery of a therapeutic waveform which produces the desired selective and reversible inhibition of pain within a desired region of the nervous structure while preventing thermal damage at sites (including the nervous structure and its surrounding tissue) which are more prone to heating.

Furthermore, use of the cooling mechanism enables tuning of the spatial field of tissue treated by the electrical signal to allow modulation of nerve signal transmission within a desired region of the nervous structure, where the desired region of the nervous structure is a portion of the nervous structure less than its complete cross-section. Cooling may be applied to tissues near the electrode 120 or to tissues neighboring the target treatment site to prevent tissue temperatures from exceeding a desired threshold level. For example, stimulation delivered via an electrode without cooling may produce a thermal field within the tissue which would be thermally damaging at some locations in the tissue. Use and placement of the cooling mechanism at locations which are anticipated to produce thermal damage to tissue enables non-damaging treatment and tuning of the spatial field of tissue treated by the electrical signal. In another example, thermal impulses in the tissue may be produced during short (e.g. less than a second) periods of time. The cooling mechanism enables reduction of these thermal impulses below a threshold level at specific locations in the tissue to enable tuning of the spatial field of tissue treated by the electrical signal. In another example, cooling and electrical waveform parameters may be adjusted concurrently to allow for treatment of a nervous structure (either treatment of a portion of the nervous structure less than its complete cross section or treatment of an entire cross section of the nervous structure) without producing thermal damage.

Example Electrode

Figure 12:
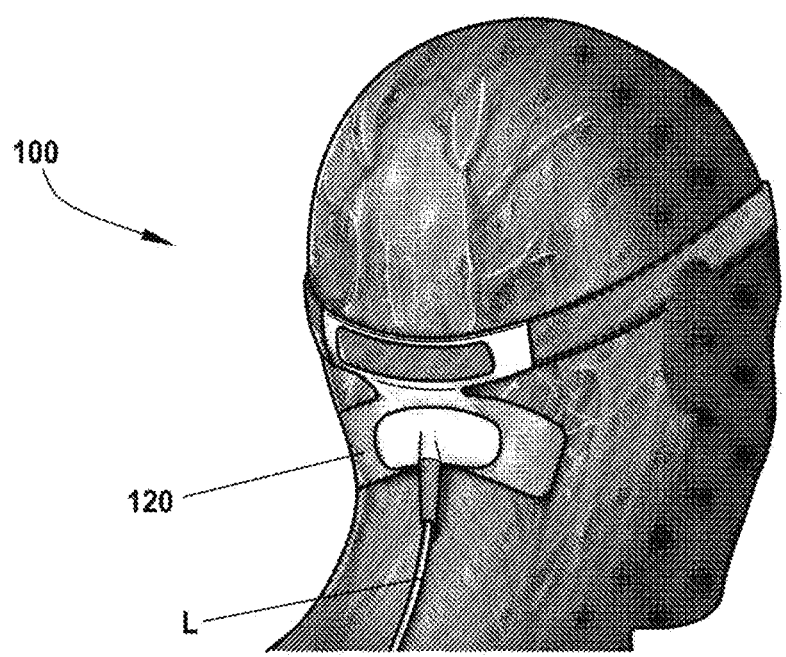
FIG. 12 is the example stimulation device 100 of FIG. 7 positioned on the back of a patient's head for targeting at least one the occipital nerves.

FIG. 12 illustrates the example stimulation device 100 of FIG. 7 positioned on the back of a patient's head for targeting at least one the occipital nerves. The electrode 120 can be provided in an electrode housing having a contact surface that is positioned adjacent an outer surface of the patient's skin over the target nervous structure. The electrode housing can include a single electrode or a plurality of electrodes. The electrode 120/electrode housing can be in the form of a paddle, cuff, cylindrical catheter or needle, wire form, or thin probe.

The electrical stimulation is delivered to the electrode 120 by a lead (L). The lead (L) includes a means for transmitting electrical energy between the electrical stimulation device 100 and the electrode 120, such as via a conductive wire or cable. The lead (L) may be directly attached to the electrode 120 in a permanent fashion or may be attachable and detachable using a conductive connector. In this case, compatible connectors would be present on the electrode 120 and on the lead (L). The lead may be directly attached to the electrical stimulation device 100/signal generator 140 in a permanent fashion or may be attachable and detachable using a conductive connector. In this case, compatible connectors would be present on the electrical stimulation device 100/signal generator 140 and on the lead (L). The lead (L) may also include avenues for transmission of fluid/gas, such as conduits 160 used for transmitting fluid/gas used to cool the electrode 120. Fluid transmission conduits 160 may be connected to the electrode 120 and a cooling device directly or via attachable/detachable connectors. The lead (L) may also be contoured to provide a shape that is optimal for placement of the electrode 120, for example to allow navigation of the electrode 120 into an ideal location on an outer surface of the patient's skin proximate the targeted nervous structure and to navigate around obstacles presenting a partial barrier between the electrode 120 and the target neural structure.

Figure 13:
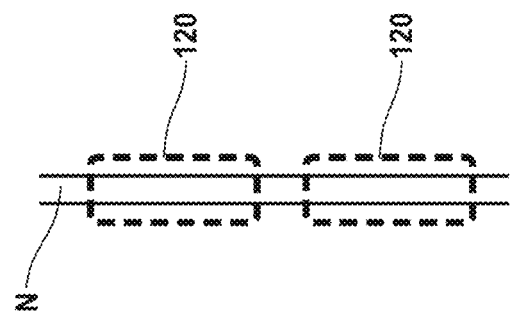
FIG. 13 is a schematic representation of an example bipolar electrode configuration.

The electrode 120 delivers electrical stimulation to the targeted neural and non-neural tissue of the nervous structure. The electrode 120 and/or a plurality of electrodes 120 can be arranged within the electrode housing to operate in a bipolar and/or monopolar fashion. FIG. 13 schematically illustrates a bipolar electrode configuration with respect to the target nervous structure (N). Each electrode 120 used in a bipolar or multi-polar fashion has at least one anode region and at least one cathode region configured to be placed adjacent the contact surface of the electrode housing and/or in contact with an outer surface of the patient's skin adjacent a target nerve. That is, the bipolar and multipolar electrode configurations, as illustrated in FIG. 13, have at least one cathode and one anode in the vicinity of the nerve (N).

Figure 14:
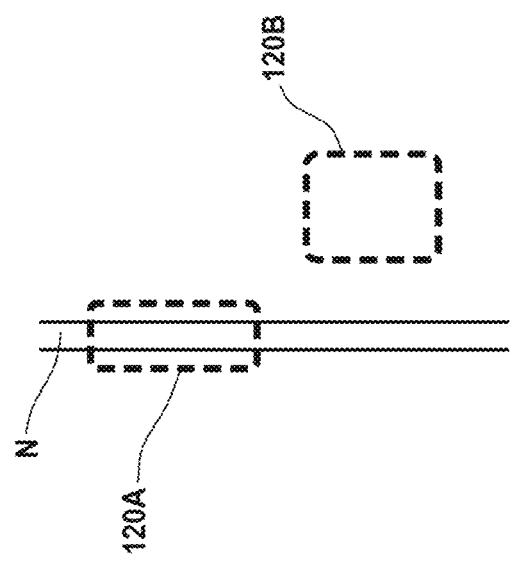
FIG. 14 is a schematic representation of an example monopolar electrode configuration.

FIG. 14 schematically illustrates a monopolar electrode configuration with respect to the target nervous structure (N). The monopolar electrode 120 illustrated in FIG. 14 includes a cathode 120A located nearby a nerve, and a return electrode 120B (e.g., anode) positioned some distance away (e.g., in the form of a patch electrode on the surface of the skin located on a different portion of the patient's head, neck and/or shoulders).

Figure 15:
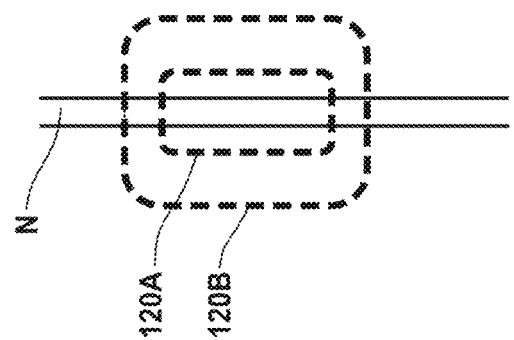
FIG. 15 is a schematic representation of an example concentrically arranged electrode configuration.

FIG. 15 schematically illustrates a concentrically arranged electrode configuration with respect to the target nervous structure (N). The concentric electrode 120 illustrated in FIG. 15 includes a centrally located cathode 120A and a return electrode 120B (e.g., anode) surrounding the cathode 120A, where both the cathode 120A and return electrode 120B are located nearby the target nervous structure (N). The electrode 120 can include one or more contacts 150 (see FIGS. 2, 11, 16-18) for delivering the electrical stimulation to the treatment area/target nervous structure. A contact 150 is defined as a portion of the electrode 120 which is intended to form the interface between the electrode 120 and the tissue at which the electric stimulation is delivered to the tissue (such as to generate an electric field in the tissue). The electrode 120 and/or contact 150 are provided within the electrode housing adjacent the patient contact surface. The electrode 120 and contact 150 configuration can be designed to maximize and direct the electric field and flow of current into the target nervous structure, and deliver a therapeutic dose of the electrical stimulation to nerves of various sizes and shapes and compositions, and without unwanted stimulation of nearby tissue, while ensuring reliable placement of the electrode 120 relative to the neural structure for optimum therapeutic effect.

Several design factors of the electrode 120 are specific to contouring the electrical field and thermal fields surrounding and penetrating the nerve, to enable selective and reversible inhibition of nervous signaling in the target nervous structure while avoiding damage to the nervous structure and adjacent non-neural tissue (e.g., tissue interposed between the electrode 120 and the targeted nervous structure). Relevant design factors of the electrode 120 that can be adjusted to prevent thermal damage include, for example, contact 150 number; electrode 120 and/or contact 150 size, geometry/shape, surface area, orientation, material, and/or coating; use of an electrolytic medium; electrical stimulation delivery fashion (e.g., monopolar, bipolar, multipolar); return path; controlling the amount of electrode-skin impedance; electrode 120 and/or contact 150 penetration depth through an outer layer of the skin; electrode fastening mechanism; and a cooling mechanism/parameter (e.g., rate of cooling of the electrode 120, flow rate of cooling medium, cooling medium pressure, measured temperature (e.g., at the treatment site, at the electrode or a portion thereof, at the stimulation device 100, at the patient's skin, at a portion of the cooling mechanism). These factors influence the thermal field produced by the electrical waveform, including the occurrence of thermal damage at some locations in the tissue relative to the electrodes. Adjustment and tuning of these factors enables the electric field and thermal field to be steered through the appropriate neural structure or portion neural structure to produce selective and reversible inhibition of pain while avoiding thermal damage to the nervous structure and/or adjacent neural and non-neural tissue. Additionally, adjustment and tuning of these factors enables the electric field and thermal field to be steered through the appropriate neural structure or portion of the neural structure to allow the therapeutic treatment to be effectively delivered in a single application and to adjust the time-course of reversibility of the treatment effects. Tuning and adjusting these factors also allows for shaping of the electric and thermal fields to treat the entire cross section of large nervous structures such as large peripheral nerves (>2.5 mm diameter), cranial nerves, ganglia, autonomic nerves, plexuses, and the spinal cord, as well as to treat portions of both large and small neural structures.

For example, the size, geometry/shape, inter-electrode spacing and orientation of the electrode 120 and/or contact 150 are specific to contouring the electrical field and thermal fields surrounding and penetrating the nerve, to enable selective and reversible inhibition of the nervous signaling in the target nervous structure. As described above, the electrode 120 can be provided in an electrode housing having a contact surface such that the electrode 120 is positioned adjacent an outer surface of the patient's skin over the target nervous structure. The electrode 120, contact 150, and/or electrode housing can include a curved surface and/or can be composed of a flexible material such that the electrode 120, contact 150 and/or electrode housing conform to an outer surface of the patient's body and provide uniform contact and pressure to the patient's skin. Accordingly, the electrode 120, contact 150 and/or electrode housing can define a size, shape and/or curvature corresponding to the size and shape of the target nervous structure and/or the shape of the outer surface of the patient's anatomy. For example, the electrode 120, contact 150 and/or electrode housing can have an elongated shape having a curvature corresponding to the curvature of the course of the target nervous structure. The electrode 120 and/or contact 150 can be arranged within the electrode housing to be positioned adjacent the patient's skin such that the electrode 120 and/or contact 150 is located generally parallel to the long axis of the targeted nervous structure. In an example system 100, the electrode 120 and/or contact 150 have a length sufficient to span multiple nodes of Ranvier, the unmyelinated portions of the target nervous structure. That is, the electric field produced at/beneath the skin at the target nervous structure is sufficient to inhibit a length of the nerve that is greater than the distance between at least two nodes of Ranvier, e.g., a length of the nervous structure greater than about 3-5 mm. In an example system, the electrode 120/electrode contact length must be at least 10 mm long and can be up to 5 cm long. This length ensures that multiple nodes of Ranvier and conductive channels of the target nervous structure are modulated by the electrical stimulation and generated electric field to inhibit nervous signaling, even in large nerves where the nerve fibers serpentine throughout the nerve fascicles, and fascicles throughout the nerve. Accordingly, the size, shape, curvature and/or orientation of the electrode 120 and/or contact 150 ensures that the electrical stimulation provides an electrical field of sufficient magnitude and spatial extent (e.g., maximize and direct the electrical field) along the nerve to inhibit signaling in the targeted a nervous structure (e.g., in the targeted nervous structure and/or in a downstream nervous structure).

In another example, the size and shape of electrical contacts 150 or the number of electrical contacts 150 can be adjusted to optimize surface area contact with the patient's skin to maximize and direct the electrical field created by the electrical stimulation. In an example system 100, the electrical contact 150 and/or electrode 120 can have a contact surface area ranging from about 1 mm$^2$ to about 20,000 mm$^2$, from about 100 mm$^2$ to about 10,000 mm$^2$, and from about 200 mm$^2$ to about 5,000 mm$^2$, to accommodate the sizes of electric and thermal fields that are needed to deliver therapeutic treatment to portions of small and large nervous structures as well as to the entire cross section of small and large nervous structures. Preferably, when treating large nerves, the electrode contact 150 and/or electrode 120 has a surface area ranging from about 1,000 mm$^2$ to about 10,000 mm$^2$. In one example, the width of the contact surface of the electrode 120 and/or contact 150 is at least about 17 cm. Such an electrode 120 can be used to deliver electrical stimulation to the each of a patient's lesser occipital nerves. In another example, the width of the contact surface of the electrode 120 and/or contact 150 is at least 11 cm. Such an electrode 120 can be used to deliver electrical situation to each of a patient's greater occipital nerves. In a further example, the width of the contact surface of the electrode 120 and/or contact 150 is at least about 5 cm. Such an electrode 120 can be used to deliver electrical stimulation to each of the lesser occipital nerves of a small adult patient or child patient.

The surface area of the electrode 120 can be optimized so as to provide sufficient interaction of the electric field with the target nervous structure(s) while limiting shunting currents in the tissue. Electrical contacts 150 which are too large may include portions of the contact 150 surface which do not contact the patient's skin adjacent the neural structure and, as a result, serves as a shunting pathway through which current may flow. Shunting currents are currents which are transmitted through the tissue but not through the target neural or non-neural tissue. Shunting currents result in higher power requirements for the electrical stimulation device and can cause un-needed heating of the tissue. However, maximizing the surface area of the electrode may be desirable to minimize damage to the tissue, for example, by maintaining the delivered power density below a possible damage threshold of 0.25 W/cm$^2$. One example of an optimized electrode shape that maximizes surface area while minimizing shunting is a long, narrow electrode which follows the course of the nerve. Furthermore, this long, narrow design maximizes the effect of the electrical waveform on the nerve by increasing the length of nerve treated by the waveform (e.g. the number of nodes of Ranvier).

Figure 16:
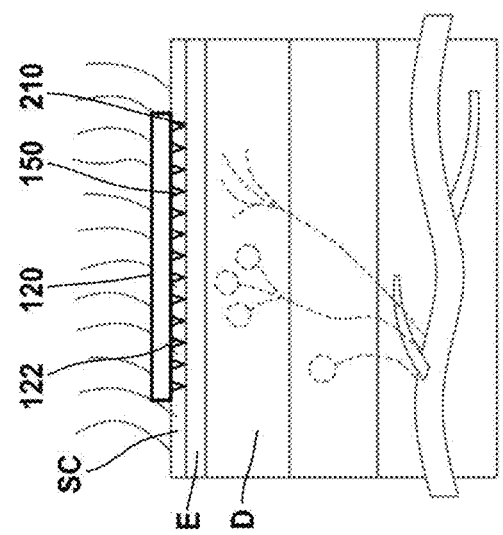
FIG. 16 is a schematic representation of patient anatomy and electrode.

Similarly, the surface area of the electrode 120/contact 150 must be sufficiently high to deliver the electrical stimulation without causing damage to the patient's skin caused by high power densities. To reduce power density, it is desirable to increase the surface area of the electrode 120/contact and/or to reduce the voltage and/or current required to achieve therapeutic levels of electrical stimulation. The electrode 120 and/or contacts 150 can include a conductive pathway element 122 that increases surface area and facilitates a conductive pathway between the electrode 120 and the targeted nervous structure. For example, the electrode 120/contact 150 can include a conductive pathway element 122 located adjacent the electrode 120 and/or the contact 150 that facilitates transmission of the electrical stimulation from the electrode 120 towards the targeted nervous structure (N), effectively reducing the power required to be delivered to achieve therapeutic-level dosing of the electrical stimulation waveform. FIG. 16 provides a schematic representation of patient anatomy and an example electrode 120 including a conductive pathway element 122 that penetrates at least a portion of the outer surface (e.g., stratum corneum (SC)) of the patient's skin. The conductive pathway element 122 can include, for example, an array of micro-needles that extend from the electrode 120 and/or contact 150 and pierce the stratum corneum (SC) up to or through the epidermis (E) or dermis (D) of the skin. The electrical stimulation passes or is conducted through or across the micro-needles and the patient's skin, bypassing the patient's hair. Adjusting the frequency content or shape of the electrical stimulation waveform also helps to change the power required to achieve therapeutic levels of stimulation, and can thus influence power density.

Figure 17:
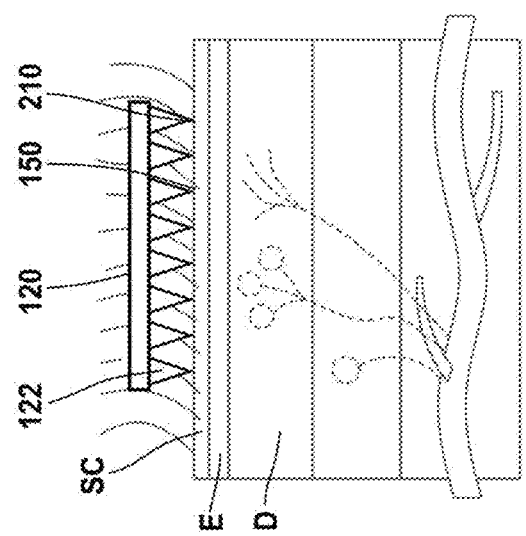
FIG. 17 is a schematic representation of patient anatomy and electrode.

FIG. 17 provides a schematic representation of patient anatomy and another example electrode 120 including a comb-like conductive pathway element 122. The comb-like conductive pathway element 122 extends from the electrode 120 and/or contact 150, passes through the patient's hair and is pressed into the patient's skin. The comb-like conductive pathway element 122 may pierce the stratum corneum (SC), but does pass through to the dermis (D). The electrical stimulation passes or is conducted through or across the comb-like structure and the patient's skin. Such a comb-like element can also help to bypass hair, for example when targeting the occipital nerves.

Figure 18:
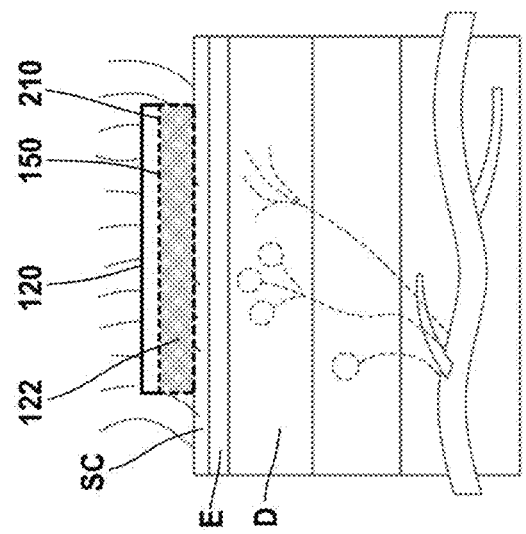
FIG. 18 is a schematic representation of patient anatomy and electrode.

FIG. 18 provides a schematic representation of patient anatomy and another example electrode including an electrolytic medium (e.g., a conductive gel, a conductive cream, a conductive adhesive, a saline soaked sponge) type of conductive pathway element 122. This electrolytic medium-like conductive pathway element 122 is coupled between the electrode 120 and/or contact 150 and an outer surface of the patient's skin. The electrical stimulation passes or is conducted through the electrolytic medium and the patient's skin. The use of a conductive pathway element 122, such as those described with respect to FIGS. 16-18, provides an electrode 120 and contact 150 with low impedance and ensures good electrode-tissue contact during delivery of the electrical stimulation. An electrolytic medium can also assist in bypassing hair to enable contact with the skin.

In another example, the material of the electrode 120 and/or contact 150 can be selected to maximize and direct the electrical field created by the electrical stimulation towards the target nervous structure, while limiting electrode 120/contact 150 degradation. For example, the electrode 120 and/or contact 150 can be constructed from or coated with platinum which is highly conductive and stable during delivery of the electrical stimulation. Other materials and material coatings are also envisioned to improve the stability of the interface during stimulation.

In another example, the electrode 120 can include at least two contacts 150 that operate dependently in a multipolar fashion to allow for current-steering and/or current-focusing of the resultant electric field. In another example, the electrode 120 includes at least two contacts 150 (e.g., two contacts 150 on the same electrode 120 or multiple electrodes 120 with their corresponding contacts 150) that operate independently. In this manner, the electrical stimulation delivered by each of the electrodes 120 can be interleaved such that the total electrical stimulation delivered to the neural structure is delivered in less (half) the time. Specifically, each of the separate electrodes 120 can deliver an intermittent electrical stimulation signal, where the electrical stimulation of the first electrode is interleaved with the electrical stimulation of the second electrode, e.g., an "on cycle" of the first electrical stimulation delivery occurs during an "off cycle" of the second electrical stimulation and an "on cycle" of the second electrical stimulation delivery occurs during an "off cycle" of the first electrical stimulation.

In another example, the electrode 120 can include multiple electrode contacts 150 that can be selected for steering of the electric and thermal fields by selecting one or more electrode contacts 150 to be used as the anode and one or more other electrode contacts to be used as the cathode. The selection of different electrode contact combinations enables adjustment of the shape and size of the electric field and thermal field. For example, a brief test pulse of electrical stimulation may be delivered via a subset of contacts to determine proximity and coverage of the nerve, and more contacts may be added until sufficient contact with the nerve is verified (for example by monitoring motor output of the leg via movement or electromyography).

Example Signal Generator

The electrical stimulation device 100 can include a signal generator 140 coupled to the electrode 120 and the controller 130. The signal generator 140 produces the stimulation waveform, including the parameters of the stimulation waveform discussed above. The signal generator 140 includes the necessary software and hardware components to produce the specified stimulation waveform(s) and to allow for modulation of the stimulation waveforms by means of the controller 130. The signal generator 140 also includes the ability to deliver stimulation to the nervous structure via the electrode(s) 120 while electrically isolating the electrode 120 and patient from grounded circuitry and other ground connections, such that the patient is not grounded when the electrode(s) 120 are coupled to the patient's body. This is accomplished, for example, via inductors or via optical isolators. Additionally, the signal generator 140 can include capacitors, inductors, resistors, and other passive circuit components near the output to the electrode 120 which ensure charge balance, reduce DC offset, or otherwise provided the desired regulation of the waveform parameters discussed earlier. Furthermore, feedback monitoring circuitry can be incorporated to collect information regarding the waveform delivered (such as the current, voltage, power) and the temperature (for example as monitored via a temperature monitoring mechanism (e.g., temperature sensor 210) at the electrode 120 or otherwise in the tissue). Parameters of the cooling mechanism such as temperature of the fluid/gas cooling medium, flow rate and pressure of the fluid/gas, the heat transfer rate from the electrode 120 and/or surrounding tissue, etc. may also be gathered.

Example Controller and Power Supply

As described generally above, the controller 130 directs operation of the stimulation device 100/signal generator 140 to provide the electrical stimulation to the target neural structure by means of the electrode 120. The controller 130/signal generator 140 are electrically coupled to a power source 180 that supplies the electrical energy to the stimulation device 100/electrode 120. The power source 180 can include an isolated power supply, such that all the instruments in the system can be powered by an isolated power supply 180 to protect them from ground faults and power spikes carried by the electrical main. The power source 180 can also include one or more batteries, used either for primary or backup power, which would allow the device to be operated without attachment to the electrical main at a facility.

Specifically, the controller 130 directs operation of the signal generator 140 to deliver an electrical stimulation signal to the target nervous structure. The controller 130 may have onboard memory to facilitate high speed data capture, output control, and processing, as well as, independent waveform sample rates and on-line analysis. These components of the controller enable collection of the feedback data needed to understand the waveform delivered via the electrode as well as the parameters of the cooling mechanism and the thermal and electrical state of the tissue. This feedback enables tuning of such treatment parameters in order to provide selective and reversible inhibition of pain.

As illustrated schematically in FIG. 1, the stimulation device can include one or more electrodes 120 connected by to an electrical lead (L) to the controller 130 via the signal generator 140. The controller 130 can include control logic and software designed to deliver the desired electrical stimulation to a patient. The controller 130 can also process analog and digital data, and record waveform data and digital information from the patient monitor system 190 and can generate waveform outputs, analog outputs, and digital outputs simultaneously for real-time control of the electrical stimulation (either real-time automated control, or manual user control). For example, the controller 130 can adjust the electrical stimulation in response to feedback information received from temperature sensors coupled to the electrode 120 and/or the stimulation device 100. For example, the stimulation device 100/electrode 120 can include a temperature sensor for measuring the temperature at the contact surface of the stimulation device and/or the electrode contacts, and the patient's tissue adjacent the contact surface of the electrode 120. The temperature sensors are coupled to the controller 130 and provide feedback information regarding a measured temperature at the contact surface of the stimulation device 100 and/or the contact surface of the electrode 120 and/or at other locations in the tissue. The controller 130 or the user can then adjust a parameter of the electrical stimulation in response to the feedback information, the parameters including, for example, waveform shape, waveform frequency, waveform amplitude, electric field strength at the electrode (e.g., as measured at the electrode or at the treatment site), waveform DC offset, waveform duty cycle, tissue temperature, cooling mechanism parameter (e.g. rate of cooling, flow rate of cooling medium, cooling medium pressure, measured temperature (e.g., at treatment site, at the one or more electrodes or a portion thereof, at the electrical stimulation device, at the patient's skin, at portion of cooling mechanism), and treatment duration (e.g., a continuous delivery for a period of time, a pulsed delivery, a pulsed delivery envelope, a pulsed delivery envelope frequency, and a pulsed delivery duration). Additional feedback signals that may be relayed or recorded by the controller or used for feedback control of the electric signal include temperature, contact impedance, the current, voltage, and power of the electric signal, other parameters of the electric signal, information regarding the electric field in the tissue, blood flow, skin conductance, skin pH, transdermal water loss, heart rate, muscle activity (such as electromyography), or other physiological signals. The feedback information can be indicative of how the electrical stimulation is impacting the patient's perceived pain inhibition as well as potential or actual skin damage caused by the electrical stimulation. For example, feedback information regarding skin temperature, skin pH, blood flow, skin conductance, transdermal water loss and electrode impedance is useful for identifying actual or potential damage to the patient's skin. Feedback information regarding nerve activity, muscle activity, patient feedback, skin temperature, blood flow, skin conductance and heart rate is useful for identifying nerve activation (e.g., activation nerve fibers such as pain fibers, sensory fibers, or motor fibers).

Figure 19:
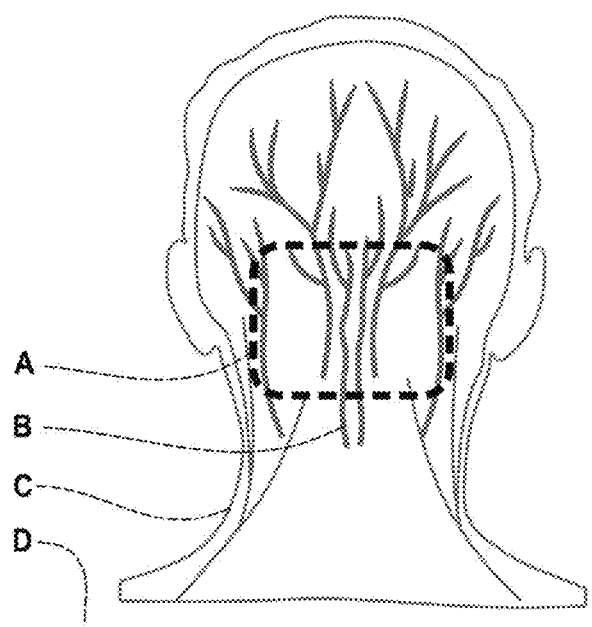
FIG. 19 is a schematic representation of example feedback signals.

FIG. 19 provides a schematic representation of example feedback signals/sensors. Element A identifies, for example, feedback signals received from the electrode 120. Element B identifies, for example, feedback signals received from a nerve activity sensor for measuring nervous signaling at the target nervous structure. Element C identifies, for example, feedback signals received from a muscle activity sensor. Element D identifies, for example, feedback signals received from a patient interface for receiving input from the user, a skin pH meter, a blood flow meter for coupling to the outer surface of the patient's skin, a skin conductance meter coupled to the outer surface of the patient's skin, a transdermal water loss sensor, a heart rate monitor for measuring the patient's heart rate, and/or an electrode contact impedance sensor.

Feedback control of the electrical stimulation is desirable to avoid producing damage in tissue, to tune the modulation of the electrical stimulation within the target neural structure, and to tune the modulation of the electrical stimulation to target both small and large nervous structures and a diversity of nervous structures such as peripheral nerves, a cranial nerves, ganglia, autonomic nerves, plexuses, and the spinal cord. Feedback control of the electrical stimulation is also desirable to enable tuning of the time course of reversibility of the inhibition of perception of pain, to tune the selectivity of the inhibition of perception of pain, and to ensure that adequate inhibition of pain is achieved, for example, with a single treatment.

Whether adjusting the electrical stimulation to selectively modulate nerve signal transmission through a select type of nerve fiber and/or through a select region of the nervous structure, the control and/or operation of the controller 130 can be adjusted varying a parameter of the electrical stimulation based on a measured feedback of the inhibition of nerve signal transmission (e.g., confirmation of no or limited nerve signal transmission from/through the target nerve), and/or a measured feedback of the temperature at the treatment site, and/or feedback from the patient regarding pain perception. The controller 130 and the user interface are also used to adjust the parameters of the stimulation waveform and properties of the electrode configurations and the cooling mechanism in response to feedback. Alternatively, a user can manually adjust parameters of the stimulation waveform and properties of the electrode configurations and the cooling mechanism in response to feedback provided via the user interface 170.

Example User Interface

The stimulation device 100 may further include a user interface 170 for receiving input from and providing input to the user (e.g., patient or medical professional). The user may provide input directing operation of the stimulation device 100 including modifications to the electrical signal. The user interface 170 can further include a display providing information to the user regarding the stimulation device 100. For example, the display can provide information regarding a status of the stimulation device 100, e.g., on/off, signal delivery mode, parameter date regarding the electrical signal, etc. The user interface 170 may be integral to the stimulation device 100. It is also contemplated that the user interface 170 may be incorporated into a remote device that is electrically (wire or wireless) coupled to the stimulation device. For example, the user interface 170 may be provided on an external tablet computer or phone. The user interface 170 may be used to allow the user to actively control parameters of the electrical stimulation (e.g., in real time) in response to feedback information from the controller 130.

The system can also include a patient monitoring system 190. The patient monitoring system 190 may be used in conjunction with the stimulation device and the user interface 170. The patient monitoring system 190 acquires, amplifies and filters physiological signals, and outputs them to the controller 130 and/or the user interface 170 for feedback. The monitoring system can include a temperature sensor coupled to an outer surface of the patient's skin for measuring changes in the patient's surface body temperature, a nerve activity sensor coupled to the patient's skin for measuring nervous signaling in the target nervous structure or another (non-target) nervous structure, a blood flow meter coupled to the patient's skin or inserted through the patient's skin, a skin conductance meter coupled to the patient's skin, a skin pH meter coupled to the patient's skin, a transdermal water loss sensor coupled to the patient's skin, a heart-rate monitor to collect electrocardiogram signals corresponding to the patient's heart rate, a muscle activity monitor to collect electromyography signals, and an electrode contact impedance sensor. A heart-rate monitor may include separate electrocardiogram (ECG) electrodes coupled with an alternating current (AC) amplifier. A muscle activity monitor may include separate EMG electrodes coupled with an AC amplifier. Other types of transducers may also be used. As described, all physiological signals obtained with the patient monitoring system are passed through a signal amplifier/conditioner. The parameters of the electrical stimulation can be adjusted in response to the feedback information received at the patient monitoring system 190 by either the controller 130 or user. For example, at least one parameter of the electrical signal can be adjusted by the controller 130 in response to feedback information received from the temperature sensor, an impedance meter, the blood flow meter, the skin conductance meter, the skin pH meter, the transdermal water loss sensor, the heart rate monitor, and the muscle activity monitor. Information regarding the stimulation waveform and parameters as well as the electrical the thermal properties of the tissue, the electrode, and the cooling mechanism can also be provided via the user interface 170 and used to adjust at least one parameter of the electrical stimulation or the cooling mechanism or the electrode configuration. The adjusted parameter of the electrical signal can include, for example, a waveform shape, a waveform frequency range, a waveform amplitude range, an electrical field strength at the electrode, a waveform DC offset, a waveform duty cycle (e.g., continuous delivery, intermittent delivery), a tissue temperature, a cooling mechanism parameter, and a treatment duration. Additionally, the electrode configuration (e.g. bipolar, multipolar, monopolar, interleaved, etc.) can also be adjusted in response to feedback information.

Example Computing System

While the methods and systems have been described in connection with preferred embodiments and specific examples, it is not intended that the scope be limited to the particular embodiments set forth, as the embodiments herein are intended in all respects to be illustrative rather than restrictive.

As used herein, "computing device" may include a plurality of computers. The computers may include one or more hardware components such as, for example, a processor, a random access memory (RAM) module, a read-only memory (ROM) module, a storage, a database, one or more input/output (I/O) devices, and an interface. Alternatively, and/or additionally, controller may include one or more software components such as, for example, a computer-readable medium including computer executable instructions for performing a method associated with the exemplary embodiments. It is contemplated that one or more of the hardware components listed above may be implemented using software. For example, storage may include a software partition associated with one or more other hardware components. It is understood that the components listed above are exemplary only and not intended to be limiting.

Processor may include one or more processors, each configured to execute instructions and process data to perform one or more functions associated with a computer for indexing images. Processor may be communicatively coupled to RAM, ROM, storage, database, I/O devices, and interface. Processor may be configured to execute sequences of computer program instructions to perform various processes. The computer program instructions may be loaded into RAM for execution by processor. As used herein, processor refers to a physical hardware device that executes encoded instructions for performing functions on inputs and creating outputs.

A processor can be microcontrollers, microprocessors, or logic circuits such as ASICs (Application Specific Integrated Circuit), CPLDs (Complex Programmable Logic Device), FPGA (Field Programmable Gate Array), or other programmable logic integrated circuits. In some embodiments, a processor is configured to execute instruction stored in a memory of the device.

RAM and ROM may each include one or more devices for storing information associated with operation of processor. For example, ROM may include a memory device configured to access and store information associated with controller, including information for identifying, initializing, and monitoring the operation of one or more components and subsystems. RAM may include a memory device for storing data associated with one or more operations of processor. For example, ROM may load instructions into RAM for execution by processor.

Storage may include any type of mass storage device configured to store information that processor may need to perform processes consistent with the disclosed embodiments. For example, storage may include one or more magnetic and/or optical disk devices, such as hard drives, CD-ROMs, DVD-ROMs, or any other type of mass media device.

Database may include one or more software and/or hardware components that cooperate to store, organize, sort, filter, and/or arrange data used by controller and/or processor 122. For example, database may store hardware and/or software configuration data associated with input-output hardware devices and controllers, as described herein. It is contemplated that database may store additional and/or different information than that listed above.

I/O devices may include one or more components configured to communicate information with a user associated with controller. For example, I/O devices may include a console with an integrated keyboard and mouse to allow a user to maintain a database of images, update associations, and access digital content. I/O devices may also include a display including a graphical user interface (GUI) for outputting information on a monitor. I/O devices may also include peripheral devices such as, for example, a printer for printing information associated with controller, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface may include one or more components configured to transmit and receive data via a communication network, such as the Internet, a local area network, a workstation peer-to-peer network, a direct link network, a wireless network, or any other suitable communication platform. For example, interface may include one or more modulators, demodulators, multiplexers, demultiplexers, network communication devices, wireless devices, antennas, modems, and any other type of device configured to enable data communication via a communication network.

Example Method

The present disclosure encompasses a non-invasive method for modulating targeted neural- and non-neural tissue of a nervous structure with a single application of electrical energy to inhibit pain perception by a patient. The method of practicing the present invention begins with positioning the patient in a comfortable position. A heart rate monitor (ECG), a muscle activity monitor (EMG), or any other monitor may be utilized to measure the patient's response to the electrical stimulation signal. The patient may be monitored for a period of time to determine a baseline status before the application of the electrical stimulation signal.

Next the targeted nervous structure can be identified and located. The electrical signal is delivered transcutaneously and the targeted nervous structure may be located utilizing a stimulation device such as a nerve locator (e.g., Ambu® Ministim® nerve stimulator and locator), utilizing the electrode 120. The nerve can also be located by passing low-levels of stimulation energy signal through the stimulation device. A stimulus-elicited muscle twitch in a distal muscle group with low stimulation amplitudes (single pulse), or an evoked sensation as perceived by the patient will indicate that the stimulation point is close enough for modulating nerve signal transmission.

The electrical stimulation device 100 is then positioned at the treatment site on an outer surface of the patient's skin proximate the targeted neural- and non-neural tissue of the nervous structure. The electrodes 120/leads (L) are attached to an external stimulation device/signal generator 140, or can be fixed to a handheld stimulation device. Initial placement of the electrodes 120 may include navigation of the electrode 120 and/or lead (L) under imaging guidance (such as with ultrasound) to a location proximate the target neural structure. Additional positioning tools may be used, such as physical markings providing on the patient's skin (e.g., a permanent or semi-permanent tattoo), that facilitate placement of the electrode on an outer surface of the patient's skin proximate the target neural structure.

Positioning the electrode 120 near the nervous structure may including delivering an initial electrical stimulation to the treatment site via the electrode 120 and measuring the voltage and/or the current at the electrode 120. Based on the measured voltage and/or current, the position of the electrode 120 at the treatment site (near the target nervous structure) is adjusted and confirmed. Further initial electrical stimulation signals are delivered to the treatment site and the position of the electrode 120 is adjusted, iteratively until the measured voltage and/or current corresponds to a threshold voltage and/or threshold current. The alignment of the electrode 120 with the targeted nervous structure may also include stimulating a physiological response in the patient (e.g., activation of nervous tissue, skin temperature, skin blood flow, skin conductance, heart rate, and muscle activity). As such, the method may further include measuring at least one of a nervous tissue signal, a cutaneous temperature change, a cutaneous blood flow change, a skin conductance change, and a heart rate change, and a change in muscle activity. A change (e.g., an increase) in nervous tissue signaling is indicative of placement of the stimulation device in alignment with the targeted nervous structure. Similarly, a change (e.g., increase or decrease) in cutaneous temperature, a change (e.g., an increase or a decrease, generally dependent on the target nerve) in cutaneous blood flow, a change (e.g., an increase or a decrease, generally dependent on the target nerve) in skin conductance, or a change (e.g., an increase) in muscle activity may also be indicative of placement of the stimulation device in alignment with the targeted nervous structure. For example, when applying electrical stimulation to a largely sympathetic nerve target, an increase in cutaneous blood flow is indicative of correct placement of the stimulation device. In another example, when applying the electrical stimulation to a largely parasympathetic nerve target (e.g., the vangus nerve, some gaglia), a decrease in cutaneous blood flow is indicative of correct placement of the stimulation device.

Positioning the electrode 120 near the nervous structure may also include applying a conductive pathway element 122 to the electrode and/or the patient's skin in order to maximize and direct the electric field, deliver the therapeutic dose of stimulation energy to small and large nerves, and ensure reliable electrode/nerve placement for optimum therapeutic effect. In one example, the conductive pathway element 122 may include an electrode 120 having an array of micro-needles on provided on the contact surface for positioning adjacent the patient's skin such that at least one of the micro-needles pierce the stratum corneum up to or through the epidermis or dermis of the skin adjacent the target nervous structure. In another example, the conductive pathway element 122 may include an electrode 120 having a comb-like structure that passes through the patient's hair and is pressed into the patient's skin such that the comb-like conductive pathway element 122 pierces the stratum corneum, but does pass through to the dermis. In a further example, the method of practicing the present invention may further include the use of an electrolytic coupling medium as the conductive pathway element 122. Example coupling mediums include, for example, an electrically conductive liquid, gel or paste that may be applied to the patient's skin and/or the contact surface of the electrode 120. Alternatively and/or additionally, one or more skin moisturizers, humectants, exfoliators or the like may be applied to the skin for the purpose of enhancing the conductivity of the skin and/or lowering impedance of the skin. Example conductive pastes include Ten20™ conductive paste from Weaver and Company, Aurora, Colorado., and ELEFIX Conductive Paste from Nihon Kohden with offices at Foothill Ranch, California. Examples of conductive gels include Spectra 360 Electrode Gel from Parker Laboratories, Inc., Fairfield, New Jersey, or Electro-Gel from Electro-Cap International, Inc., Eaton, Ohio. An example exfoliator that can be used to prepare skin prior to application of transcutaneous electrodes is Nuprep skin prep gel from Weaver and company, Aurora, Colorado.

Once positioned proximate the target neural structure, the electrode 120 is removably coupled to the patient's head and/or neck. The electrode 120 may be securely coupled to the patient's skin and/or head/neck such that the position of the electrode with respect to the target nervous structure is constant for at least the duration of the treatment. For example, the electrode 120 may be coupled to the patient's head, neck and/or shoulders using an adhesive, a hair clip, and/or a strap extending from the stimulation device 100 and around at least a portion of one of the patient's head and/or ears. The electrode may also be hand-held.

The method may further include positioning one or more return electrodes on the outer surface of the patient's skin. Each anode desirably has a skin contacting surface such that the skin contacting surface of the anode has at least the same (or greater) surface area as the contacting surface of the stimulating electrode. The one or more return electrodes may be positioned on the skin a distance away from one or more stimulating electrodes sufficient to reduce shunting, e.g., on a different portion of the patient's head, neck and/or shoulders.

After electrodes 120 are placed and secured in position, traditional electrical stimulation can be delivered through the electrodes 120 to assure sufficient tissue/nerve proximity, and impedance measurements can be collected and used similarly. The stimulation device can them be programed to optimize electrode contact selection, return electrode selection and stimulation parameters, as discussed above. It is contemplated that selection of optimal stimulation parameters can include delivery of different candidate waveforms with different parameter configurations until a suitable outcome is achieved. It is further contemplated that selection of optimal electrode contact 150 configurations and return electrode configurations can include delivery of electric signals via different configurations of electrode contacts 150 and return electrodes until a suitable outcome is achieved. These optimizations may be performed manually by the user or may be delivered by the controller in closed-loop as part of an algorithmic iterative search or a pre-programmed search.

The electrical stimulation can then be delivered to the treatment site proximate targeted nervous structure via the electrode(s) 120 using one or more of the stimulation parameters discussed above. The controller 130, receiving a supply of electrical energy from a power source 180 can direct operation of the stimulation device 100 to provide an electrical signal sufficient to selectively modulate the targeted neural- and non-neural tissue inhibiting nervous signaling through the target nervous structure (or a downstream nervous structure) and thereby inhibiting nervous signaling, while not damaging the tissue interposed between the stimulation device 100 and the targeted nervous structure. The user may also control the parameters of the electrical signal in real time in response to feedback provided via the controller 130 to the user interface 170.

Where the electrode comprises at least two electrodes that operate independently, it is contemplated that a first electrical stimulation signal may be delivered via the first electrode and a second electrical stimulation signal via the second electrode. The first and second electrical stimulation signals can be intermittently outputted, where the first electrical stimulation is interleaved with respect to the second electrical stimulation. In this configuration, the on cycle of the first electrical stimulation occurs during an off cycle of the second electrical stimulation. Similarly, the on cycle of the second electrical stimulation occurs during an off cycle of the first electrical stimulation.

Similarly, the stimulation device 100 may include a second electrode $120_2$ for proving an electrical stimulation to a second targeted nervous structure. The second targeted nervous structure can be identified and located as described above. Likewise, the second electrode $120_2$ may be positioned at a second treatment site adjacent the second targeted nervous structure and may be coupled to the patient at a different location than the first electrode $120_1$. In this example, a second electrical stimulation is delivered to the second targeted nervous structure by the second electrode $120_2$ such that application of the second electrical stimulation to the second treatment site modulates the function of at least one of the neural- and non-neural tissue of the second targeted nervous system structure, inhibiting nervous signaling (e.g., through the targeted neural- and non-neural tissue) while not damaging tissue interposed between the second electrode $120_2$ and the second targeted nervous system structure. The first and second electrodes $120_1$, $120_2$ can operated independently, wherein at least a portion of the application of the first electrical stimulation at the first treatment site and at least a portion of the application of second electrical stimulation at the second treatment site both occur simultaneously. It is contemplated that the application of the second electrical stimulation can either inhibit nervous signaling or activate nervous signaling in the second target nervous structure.

The perception of pain by the patient is inhibited as the application of the electrical signal to the treatment site selectively modulates the targeted neural- and non-neural tissue inhibiting nerve signal transmission. For example, nerve signal transmission may be inhibited through nerve fibers that are responsible for the transmission of pain. Meanwhile, nerve signal transmission through nerve fibers responsible for other sensory and motor function, and proprioception is preserved. The preserved "other" sensory function includes, for example, touch, vision, audition, gustation, olfaction, and balance. Application of the electrical signal can also inhibit and/or disrupt nerve signal transmission through nerve fibers responsible for transmitting signals related to thermoreception, autonomic effector activity and visceral function.

In its simplest form, the method may rely on a patient's feedback regarding their perception of pain after delivery of nerve blocking electrical stimulation to assess the effectiveness of the temporary and selective nerve signaling inhibition. Patient feedback can be provided by the user at a user interface 170 in communication with the controller 130. Alternatively and/or additionally, the method may rely on feedback collected by a recording electrode, such as an ECG, galvanic skin response, skin conductance meter, skin pH meter, transdermal water loss sensor, blood flow meter, skin or body temperature, and/or electromyogram signals to assess the effectiveness of the nerve signal inhibition, since the stimulation may occur before, during, or immediately after a surgical procedure or at a time when the patient is suffering severe acute head-and-face pain and is unable to provide meaningful feedback.

The target nervous structure can comprise a peripheral nerve (large or small), a cranial nerve, a ganglion, an autonomic nerve, a plexus, and a spinal cord. Target neural structures can include a mixture of motor, sensory and/or autonomic neurons, or may include a single type of neural activity (such as motor only, sensory only, autonomic only). Target ganglia can include a dorsal root ganglia, a sympathetic ganglia, a parasympathetic ganglia, a sphenopalatine ganglion, a gasserian ganglion, a plexus, and/or the spinal cord. In one example, the target nervous structure comprises a cranial nerve and the electrodes deliver an electrical signal to the nerve that selectively inhibits nerve signal activity associated with pain while preventing damage to the tissue interposed between the electrode 120 and the target nervous structure. For example, the electrodes 120 can deliver an electrical signal that selectively inhibits nerve signal activity in smaller diameter nerve fibers associated with sensory (pain) function, with minimal or no change in the functionality of the larger myelinated fibers that are associated with motor function, non-painful sensation, and proprioception. In one example, the inhibition of nervous signaling (e.g., in the targeted nervous structure, in a downstream nervous structure) results from the inhibition of action potential conduction in the targeted nervous structure.

The method is, in one example, directed to inhibition of the perception of head-and-face pain. Accordingly, application of the electrical stimulation to the targeted nervous structure(s) of the head, neck and/or shoulders can reduce an intensity of an episode of head-and-face pain, a duration of an episode of head-and-face pain, a frequency of episodes of head-and-face pain and/or prevent episodes of head-and-face pain from occurring. This reduction in intensity, duration, frequency and prevention can last for a period of 1 day to about 30 days after cessation of the stimulation.

Similarly, application of the electrical stimulation to the targeted nervous structure(s) of the head, neck and/or shoulders can aborts or reduces the intensity or duration of an episode of head-and-face pain during the period of time in which stimulation is delivered (i.e., during the treatment procedure) and/or for up to about of about 8 hours to about 24 hours after cessation of the stimulation.

In one example, the application of the electrical stimulation to the targeted nervous system structures selectively inhibits nervous signaling through at least one of a select type of neural tissue (e.g. pain-transmitting nerve fibers, non-pain transmitting nerve fibers, sensory fibers, motor fibers, proprioceptive fibers, cell bodies, axons, myelinated nerve fibers, unmyelinated nerve fibers, large-diameter nerve fibers, small-diameter nerve fibers) of a nervous structure(s) (e.g., in the targeted nervous structure, in a downstream nervous structure), while the function of at least one of a non-selected type of neural tissue (e.g. pain-transmitting nerve fibers, non-pain transmitting nerve fibers, sensory fibers, motor fibers, proprioceptive fibers, cell bodies, axons, myelinated nerve fibers, unmyelinated nerve fibers, large-diameter nerve fibers, small-diameter nerve fibers) of a nervous structure(s) (e.g., in the targeted nervous structure, in a downstream nervous structure) is selectively not inhibited (e.g., nervous signaling is preserved).

In a further example, the application of the electrical stimulation to the treatment site inhibits nervous signaling in a type of neural tissue (e.g. pain-transmitting nerve fibers, non-pain transmitting nerve fibers, sensory fibers, motor fibers, proprioceptive fibers, cell bodies, axons, myelinated nerve fibers, unmyelinated nerve fibers, large-diameter nerve fibers, small-diameter nerve fibers) of a nervous structure(s) (e.g., in the targeted nervous structure, in a downstream nervous structure), while activating nervous signaling in a different type of neural tissue (e.g. pain-transmitting nerve fibers, non-pain transmitting nerve fibers, sensory fibers, motor fibers, proprioceptive fibers, cell bodies, axons, myelinated nerve fibers, unmyelinated nerve fibers, large-diameter nerve fibers, small-diameter nerve fibers) of a nervous structure(s) (e.g., in the targeted nervous structure, in a downstream nervous structure).

In another example, the electrical stimulation can modulate the function of adjacent non-neural tissue of the targeted nervous structure by, for example, reducing blood flow to the pain-stimulating areas and/or reducing abnormal excitation of the peripheral pain fibers.

The controller 130 can be adjusted to vary at least one parameter of the electrical stimulation to inhibit nervous signaling while avoiding producing damage in the tissue interposed between the electrode 120 and the targeted nervous system structure(s). The adjustable parameters of the electrical stimulation include, for example, a waveform shape, a waveform frequency, a waveform amplitude, an electrical field strength generated at the electrode (e.g., measured at the electrode or at the treatment site), a waveform DC offset, a waveform duty cycle, a tissue temperature, a cooling mechanism parameter (e.g., rate of cooling, flow rate of cooling medium, cooling medium pressure, measured temperature (e.g., at treatment site, at the one or more electrodes or a portion thereof, at the electrical stimulation device, at the patient's skin, at portion of cooling mechanism)), and a treatment duration. In one example, the controller 130 is adjusted to vary at least one parameter of the electrical stimulation to reduce at least one of an intensity, duration, and frequency of a head-and-face pain episode. In another example, the controller 130 is adjusted to vary at least one parameter of the electrical stimulation to selectively inhibit transmission of nervous signaling in a subset of neural tissue (e.g., pain-transmitting nerve fibers, non-pain transmitting nerve fibers, sensory fibers, motor fibers, proprioceptive fibers, cell bodies, axons, myelinated nerve fibers, unmyelinated nerve fibers, large-diameter nerve fibers, small-diameter nerve fibers) of a nervous structure(s) (e.g., in the targeted nervous structure, in a downstream nervous structure). In a further example, the controller 130 is adjusted to vary at least one parameter of the electrical stimulation to reduce onset response of a nervous structure(s) (e.g., in the targeted nervous structure, in a downstream nervous structure) or activation of the nervous structure(s) at the onset of nervous signaling inhibition.

In a further example, the controller 130 is adjusted to vary at least one parameter of the electrical stimulation based on a measured feedback selected from the group consisting of: measured inhibition of nervous signaling, measured temperature (e.g., at the treatment site, at the electrodes or a portion thereof, at the electrical stimulation device, at the patient's skin), input from the patient (e.g., input regarding pain sensation), a feedback corresponding to at least one of the adjustable parameters, a treatment setting associated with a time course of recovery, electrode contact impedance, electric field generated in the tissue, patient physiological response (e.g., skin pH, blood flow, skin conductance, heart rate, muscle activity (e.g., such as electromyography), and transdermal water loss), and a combination thereof.

The method includes the application of the electrical stimulation to the neural- and non-neural tissues of the targeted nervous structure for inhibiting nerve signal transmission through at least one of a myelinated Aδ fiber and/or an unmyelinated C fiber provided in the nerve, wherein the electrical signal preserves nerve signal transmission through at least one of the Aβ and Aα fibers, and/or motor fibers. In a further example, various parameters of the electrical signal can be adjusted to selectively inhibit at least one of the myelinated Aδ fibers or the unmyelinated C fibers, e.g., inhibit nerve signal transmission through the myelinated Aδ fibers while preserving nerve signal transmission through the unmyelinated C fibers, and vise-a-versa. In a further example, various parameters of the electrical signal can be adjusted to differentially inhibit nerve signal transmission/ function of the myelinated Aδ fibers, such that the myelinated Aδ fibers have a larger percentage of fibers inhibited than the unmyelinated C fibers. Likewise, various parameters of the electrical signal can be adjusted to differentially inhibit nerve signal transmission/function of the unmyelinated C fibers, such that the unmyelinated C fibers have a larger percentage of fibers inhibited than the myelinated Aδ fibers.

In another example, the application of the electrical signal to the neural- and non-neural tissues of the targeted nervous structure modulates neural or non-neural tissue function in a way the results in downstream or secondary effects that result in the inhibition of pain, while preserving motor, non-painful sensory, and proprioceptive activity. For example, various parameter of the electrical signal can be adjusted to selectively modulate function which results in reduction of pain that originated from activity in myelinated Aδ fibers and/or unmyelinated C fibers, while preserving motor, non-painful sensory, and proprioceptive function, such as that transmitted by Aβ and Aα fibers, and/or motor fibers. In a further example, various parameters of the electrical signal can be adjusted to selectively modulate function which results in reduction of pain that originated from activity in myelinated Aδ fibers or the unmyelinated C fibers, e.g., inhibit pain that originated from activity in myelinated Aδ fibers while preserving pain that originated from activity in unmyelinated C fibers, and vise-a-versa. In a further example, various parameters of the electrical signal can be adjusted to differentially modulate function which results in reduction of pain that originated from activity in myelinated Aδ fibers, such that the pain originating from activity in myelinated Aδ fibers has a larger inhibition than the pain originating from activity in unmyelinated C fibers. Likewise, various parameters of the electrical signal can be adjusted to differentially modulate function which results in reduction of pain that originated from activity in unmyelinated C fibers, such that the pain originating from activity in unmyelinated C fibers has a larger inhibition than the pain originating from activity in myelinated Aδ fibers.

In another example, certain parameters of the electrical signal can be adjusted to preferentially modulate nerve signal transmission/function within a desired region of the nervous structure. Generally, the desired region is that portion of the nervous structure including the sensory components responsible for transmitting a sense of pain.

The disclosed method encompasses inhibiting the perception of pain associated with acute pain (such as acute treatment of migraines or other head-and-face pain, post-surgical pain, and trauma pain), neuropathic pain, chronic pain, and head-and-face pain. Where the pain is acute pain, the method for selectively modulating targeted neural- and non-neural tissue to inhibit the perception of pain may include applying the electrical signal immediately before a surgical procedure. The electrical signal can also be applied intraoperatively and/or immediately following a surgical procedure to inhibit the perception of pain associated with the surgical procedure and recovery. The electrical signal can also be applied at the onset of a pain episode, such as a migraine headache, to abort the acute pain episode. Where the pain is neuropathic pain or chronic pain, the method for modulating the neural- and non-neural tissue of the target nervous structure may include the user (such as a physician or a patient) applying the electrical signal as part of a pre-determined schedule for preventative care, and/or as needed by the patient to provide an on-demand bolus of therapeutic treatment/pain relief.

The method for selectively modulating targeted neural- and non-neural tissue to inhibit nerve signal transmission and a corresponding inhibition of nervous signaling may further include measuring, at a temperature sensor 210, the temperature the contact surface of the stimulation device 100 (e.g., electrode 120 contact surface) and/or the temperature of the patient's tissue (e.g., the patient's skin adjacent the contact surface of the stimulation device, the patient's tissue interposed between the contact surface of the stimulation device and the targeted nervous system structure, mucosal tissue overlaying the targeted nervous system structure) during delivery of the electrical signal. The temperature sensor 210 provides thermal feedback information regarding the measured temperature to the stimulation device (e.g., controller 130). If the thermal feedback information indicates that the temperature of the contact surface of the stimulation device 100 is above a threshold device temperature and/or if the temperature of the patient's tissue is above a threshold tissue temperature (e.g., the destructive tissue temperature), the stimulation device 100, controller 130, and/or the user can adjust the operation of the stimulation device 100 and the parameters of the electrical signal and/or a cooling mechanism to produce a cooling effect and reduce the temperature at the contact surface and patient's tissue adjacent the contact surface/electrode 120. Reducing the temperature of the contact surface and/or the patient's tissue prevents damage to the patient's tissue. In some examples, the system may include a cooling mechanism coupled to and/or integrated into the stimulation device 100 and/or electrode 120. If the thermal feedback information indicates that the temperature of the contact surface of the stimulation device 100/electrode 120 is above a threshold device temperature and/or if the temperature of the patient's tissue is above a threshold tissue temperature, the stimulation device 100, controller 130, and/or the user, may activate and control operation of the cooling mechanism to cool the contact surface of the stimulation device 100/electrode 120. The resulting cooling effect at the contact surface prevents damage to the patient's tissue when the electrical signal is delivered by preserving temperatures of the patient's tissue below a threshold tissue temperature. Likewise, the stimulation device 100/controller 130 and/or the user, may activate and control operation of the cooling mechanism to maintain the temperature of the contact surface of the stimulation device 100/electrode 120 below a threshold temperature in response to feedback information regarding the measured temperature received from the temperature sensor 210.

After the electrical signal has been delivered, and nervous signaling has been inhibited while not damaging the tissue interposed between the electrode 120 and/or contact surface of the electrode housing and the target nervous structure, the electrode(s) 120 can be removed.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Example 1

In this example, able-bodied subjects were recruited and consented for the study using IRB-approved consent forms. Subject donned scrubs and were seated in a comfortable chair. The right leg was rested on an elevated foot rest and the right leg was instrumented with muscle recording electrodes and nerve stimulation electrodes. Skin temperature was monitored via a thermocouple. Local skin perfusion (e.g. blood flow) was monitored via a skin laser skin perfusion meter. Skin pH was monitored via a glass pH probe. Nerve stimulating and electromyography (EMG) recording electrodes were placed on the right leg to enable assessment of nerve and muscle function and delivery of the electrical stimulation to inhibit nervous signaling.

Assessment of nerve function: At the beginning of the session, the subject was instrumented with surface EMG recording electrodes over the abductor hallucis, flexor digiti minimi brevis, abductor digiti minimi, and gastrocnemius muscles. Electrical stimulation (≤1 ms in duration) was delivered to the tibial nerve at the popliteal fossa, behind the knee, using adhesive surface electrodes, to produce evoked activation of each of these muscles, visible via the EMG recordings. The purpose of this stimulation was to activate the tibial nerve and subsequently the instrumented muscles in a predictable fashion for assessment of nerve and muscle function. The activation and saturation thresholds for each of the instrumented EMG channels was characterized using the stimulation at the popliteal fossa.

Delivery of stimulation waveform: A custom electrode was placed on the skin over the tibial nerve at a distal stimulation site, posterior to the medial malleolus on the ankle. The electrode used comprised a platinum ribbon, having a width corresponding generally to the width of the target nervous structure, e.g., approximately 2-3 mm wide, and having a length that enabled interaction with many nodes of Ranvier of the target nervous structure, e.g., approximately 30 mm long. The electrode was oriented on the subject's skin parallel to the course of the nerve. This custom electrode was designed to maximize surface area (length of 30 mm oriented parallel to the nerve) while minimizing shunting (width of 2-3 mm which is only slightly larger than the diameter of the tibial nerve at the ankle). A commercially-available adhesive surface electrode (25×35 mm) was placed several centimeters proximal to the custom electrode to serve as a bipolar return electrode. Stimulation was delivered in single pulses (e.g. 1 ms) at increasing amplitudes and sensory and motor thresholds were characterized. Bursts of an electrical stimulation waveform (for example, in this case a 10 kHz sine wave or a 10 kHz bipolar square wave) were then delivered at increasing amplitudes and increasing durations (e.g. from 1-150 mA, from 1 ms up to ≥20 s duration), and sensory and motor thresholds were characterized for each of the different burst durations.

Assessment of stimulation waveform effect on nerve and muscle function: In several separate trials, five pulses of stimulation were delivered at the popliteal fossa at a suprathreshold level to characterize nerve and muscle function (e.g. via the amplitude, area, and latency of the evoked EMG signal in each muscle). The electrical stimulation waveform was then delivered continuously to the tibial nerve at the ankle via the custom platinum electrode, with a starting amplitude near sensory threshold (e.g. approximately 20 mA). While the electrical stimulation was being delivered, assessment was again made of nerve and muscle function by means of five additional stimulation pulses at the popliteal fossa (and evoked EMG signals). The electrical stimulation waveform amplitude was then modulated in stages by ramping up to higher amplitudes (e.g. up to 60 mA), with functional assessment via five additional popliteal fossa stimulations at each amplitude stage. After completion of the functional assessment at the maximum amplitude, the electrical stimulation waveform was turned off, and functional assessment was made over the course of several minutes to assess recovery of function (five popliteal fossa stimulations delivered at several successive time-points).

FIG. 20A shows the staged amplitudes delivered during two different trials of the electrical stimulation waveform. In this case, the electrical stimulation waveform was a 10 kHz sine wave delivered continuously. The evoked motor response recorded near the flexor digiti minimi brevis muscle in the foot in response to stimulation of the tibial nerve at the popliteal fossa is shown in FIG. 20B, and includes assessment before each electrical stimulation waveform trial (shown in FIG. 20A), during each amplitude stage of the electrical stimulation waveform trials, and after each electrical stimulation waveform trial. During each application of the electrical stimulation waveform, the motor response evoked by proximal stimulation of the tibial nerve was inhibited, producing up to an 80% reduction in the positive-going amplitude of the evoked electromyography response (stimulation raster and EMG trace shown in FIG. 20B are concurrent with the stimulation amplitudes shown in FIG. 20A). The latency for full return of function after cessation of delivery of the electrical stimulation waveform was roughly 100 seconds. FIG. 20C shows feedback collected from the subject regarding a sensory score during each of the two electrical stimulation waveform trials. This sensory score was collected via a handheld potentiometer interface and enabled assessment of sensations perceived by the subject due to the delivery of the electrical stimulation waveform. A sensory score of 3 was designated a priori as the beginning of pain, while a sensory score ranging between 0-3 was designated as non-painful. With each successive ramp of the sine wave amplitude the sensation intensity on the plantar surface of the foot increased, often followed by a subsequent modest reduction in sensory score during the plateau phase of the amplitude stage. Notably, the sensation portrayed in FIG. 20C was described as 'paresthesia' and 'numbness'. Touch sensation of the foot was also inhibited on the plantar surface of the foot during application of the electrical stimulation waveform; the subject indicated that perception of stroking touch delivered to the plantar surface of the treated foot was substantially attenuated compared the sensation evoked by an identical stroking stimulus delivered to the contralateral foot (data not shown). No sensory deficits persisted after the cessation of the sessions.

These results suggest that the electrical stimulation waveform delivered to the tibial nerve transcutaneously indeed inhibited nervous and/or muscular signaling. This magnitude of inhibition can be tuned by adjusting the amplitude of the stimulation waveform, and full recovery of function appears to be delayed by up to several minutes after cessation of the electrical stimulation waveform.

Throughout this application, various publications may be referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims

What is claimed:

1. A system for non-invasively modulating electrical activity in neural- and non-neural tissue of an occipital nerve through a skin of a patient, the system comprising:
a wearable electrical stimulation device configured to be worn adjacent an outer surface of a neck or head of the patient, the electrical stimulation device comprising a housing coupled to a strap that extends around at least a portion of the patient's head, at least one feedback sensor, and one or more electrodes sized and configured to be placed adjacent the skin of the patient, the one or more electrodes configured to deliver an electrical stimulation transcutaneously to one or more treatment sites proximate the occipital nerve and to modulate a function of the neural tissue of the occipital nerve and/or adjacent non-neural tissue of the occipital nerve, while not damaging tissue interposed between the electrical stimulation device and the occipital nerve, wherein delivery of the electrical stimulation to the one or more treatment sites modulates the neural- and/or non-neural tissue of the occipital nerve, inhibiting nervous signaling and pain perception; and
a controller operatively coupled to the one or more electrodes of the electrical stimulation device and a power source supplying electrical energy to the one or more electrodes, wherein the controller is configured to direct operation of the electrical stimulation device to apply the electrical stimulation to the one or more treatment sites through the one or more electrodes, and wherein the controller is configured to dynamically adjust at least one parameter of the electrical stimulation in response to feedback information obtained via the at least one feedback sensor of the electrical stimulation device.

2. The system of claim 1, wherein the electrical stimulation has one or more of a frequency and amplitude sufficient to produce an inhibition of action potential conduction in the nerve fibers of the occipital nerve that results in inhibiting of pain perception,
wherein inhibiting of nervous signaling results from at least one of inhibition of action potential conduction and inhibition of action potential activation in a nervous structure that is downstream from the occipital nerve.

3. The system of claim 1, further comprising a second electrical stimulation device that delivers an electrical stimulation transcutaneously to one or more second treatment sites proximate a second targeted nervous structure that activates nervous signaling in the second targeted nervous structure,
wherein at least a portion of the application of the electrical stimulation at the treatment site and at least a portion of the application of electrical stimulation at the second treatment site both occur simultaneously.

4. The system of claim 1, wherein the controller is adjustable to control output of the controller to vary at least one parameter of the electrical stimulation to inhibit nervous signaling while avoiding producing damage in the tissue interposed between the one or more electrodes and the occipital nerve,
wherein the at least one parameter is selected from a group consisting of a waveform shape, a waveform frequency, a waveform amplitude, an electrical field strength generated at the electrode, a waveform DC offset, a waveform duty cycle, a tissue temperature, a cooling mechanism parameter, and a treatment duration,
wherein the electrical field strength is measured at at least one of the electrode and the treatment site,
wherein the cooling mechanism parameter includes at least one of a rate of cooling, a flow rate of a cooling medium, a cooling medium pressure, and a measured temperature at at least one of the treatment sites, the one or more electrodes or a portion thereof, the electrical stimulation device, the skin of the patient, and a portion of cooling mechanism.

5. The system of claim 4, wherein the electrical signal frequency is about 5 kHz to about 200 kHz.

6. The system of claim 4, wherein the electrical stimulation has a current amplitude between about 1 mA (peak-to-center, corresponding to 2 mA peak-to-peak) and about 200 mA (peak-to-center, corresponding to 400 mA peak-to-peak), a voltage amplitude between about 1 V (peak-to-center, corresponding to 2 V peak-to-peak) and about 2000 V (peak-to-center, corresponding to 4000 V peak-to-peak), or a power amplitude between about 10 mW (peak-to-center, corresponding to 20 mW peak-to-peak) and about 400 W (peak-to-center, corresponding to 800 W peak-to-peak).

7. The system of claim 4, wherein the electrical stimulation delivered to the one or more treatment sites has a waveform shape component including at least one of a continuously outputted waveform, and an intermittently outputted waveform at a duty cycle, where the waveform shape includes a sinusoidal waveform and at least one of a square waveform, a triangular waveform, a stochastic noise waveform, an impulse waveform, a shape modulated waveform, a frequency modulated wave form, an amplitude modulated waveform that provides a continuous delivery of electrical stimulation at the treatment site and a combination thereof,
wherein each of the waveform shape components can be delivered either a single time at a given duty cycle or in a burst fashion.

8. The system of claim 4, wherein the amplitude of the waveform is increased from an initial amplitude level to a final amplitude level over the duration of about 1 sec to about 5 mins at an onset of stimulation or at an onset of a burst of stimulation to reduce undesired activation of excitable tissues at the onset of stimulation or at the onset of a burst of stimulation.

9. The system of claim 1, wherein, when the stimulation device is located adjacent an outer surface of a neck or head of the patient, the electrical stimulation is delivered to a focused area about 0.5 mm to about 10 mm in diameter at a location proximate the occipital nerve.

10. The system of claim 1, wherein the stimulation device includes a body portion sized and configured to be placed adjacent to a head of the patient at a location corresponding to at least one of along a forehead, base of the skull, and along a neck, such that the electrode is provided on a contact surface of the body portion,
wherein the electrode has a shape corresponding to a size and shape of the occipital nerve such that energy provided at the electrode can modulate an area comprising at least a portion of the occipital nerves simultaneously and the electrode can provide a uniform pressure on an outer surface of the patient's skin proximate the occipital nerve.

11. A method of non-invasively modulating neural- and non-neural tissue of an occipital nerve with electrical stimulation to treat a medical condition of a patient through a skin of the patient, the method comprising:
identifying the occipital nerve;
positioning a wearable electrical stimulation device at one or more treatment sites and configured to be worn adjacent an outer surface of the patient's skin proximate the neural- and non-neural tissue of the occipital nerve, the electrical stimulation device comprising a housing coupled to a strap that extends around at least a portion of the patient's head, at least one feedback sensor, and at least one electrode located within the housing that provides an electrical stimulation to the one or more treatment sites, the electrical stimulation device being operatively coupled to a controller for directing operation of the electrode; and
delivering an electrical stimulation transcutaneously to the one or more treatment sites via the at least one electrode;
wherein the application of the electrical stimulation to the treatment site modulates the neural- and/or non-neural tissue of the occipital nerve, creating a conductive nerve block inhibiting nervous signaling in the occipital nerve and a downstream nervous structure resulting in inhibition of perception of pain, while not damaging tissue interposed between the stimulation device and the occipital nerve, and
wherein the controller is configured to direct operation of the wearable electrical stimulation device to apply the electrical stimulation to the one or more treatment sites through the one or more electrodes, and wherein the controller is configured to dynamically adjust at least one parameter of the electrical stimulation in response to feedback information obtained via the at least one feedback sensor of the wearable electrical stimulation device.

12. The method of claim 11, wherein the inhibiting of nervous signaling in the occipital nerve and in the downstream nervous structure results from inhibition of action potential conduction in the targeted nervous structure,
wherein the perception of pain comprises head and face pain.

13. The method claim 11, wherein application of the electrical stimulation to the occipital nerve selectively inhibits nervous signaling through at least one of a select type of neural tissue of the occipital nerve,
wherein function of at least one of a non-selected type of neural tissue of the occipital nerve is selectively not inhibited,
the types of neural tissue including pain-transmitting nerve fibers, non-pain transmitting nerve fibers, sensory fibers, motor fibers, proprioceptive fibers, cell bodies, axons, myelinated nerve fibers, unmyelinated nerve fibers, large-diameter nerve fibers, and small-diameter nerve fibers.

14. The method of claim 11, wherein the electrical stimulation modulates the function of the adjacent non-neural tissue of the occipital nerve by reducing blood flow to the pain-stimulating areas, reducing abnormal excitation of the peripheral pain fibers, modulating blood pressure, modulating vasodilation, modulating vasoconstriction, modulating glial cells, and/or modulating immune and inflammatory function.

15. The method of claim 11, further comprising:
adjusting the controller to vary at least one parameter of the electrical stimulation to inhibit nervous signaling while avoiding producing damage in the tissue interposed between the electrode and the occipital nerve;
wherein the at least one parameter is selected from the group consisting of a waveform shape, a waveform frequency, a waveform amplitude, an electrical field strength generated at the electrode, a waveform DC offset, a waveform duty cycle, a tissue temperature, a cooling mechanism parameter, and a treatment duration,
wherein the electrical field strength is measured at at least one of the electrode and the treatment site,
wherein the cooling mechanism parameter comprises at least one of a rate of cooling, a flow rate of a cooling medium, a cooling medium pressure, a measured temperature at the treatment site, a measured temperature at the one or more electrodes or a portion thereof, a measured temperature at the electrical stimulation device, a measured temperature at the patient's skin, a measured temperature at a portion of cooling mechanism.

16. The method of claim 15, further comprising:
adjusting the controller to vary at least one parameter of the electrical stimulation to selectively inhibit transmission of nervous signaling in a subset of neural tissue including at least one of pain-transmitting nerve fibers, non-pain transmitting nerve fibers, sensory fibers, motor fibers, proprioceptive fibers, cell bodies, axons, myelinated nerve fibers, unmyelinated nerve fibers, large-diameter nerve fibers, or small-diameter nerve fibers of the nervous structure;
adjusting the controller to vary at least one parameter of the electrical stimulation to reduce onset response of a nervous structure or activation of the nervous structure at an onset of nervous signaling inhibition;
measuring, at a temperature sensor that is operatively coupled to the electrical stimulation device and the controller, the temperature sensor being configured for obtaining measurements, a temperature of at least one of a contact surface of the electrical stimulation device and the patient's skin adjacent the contact surface during delivery of the electrical stimulation, wherein the temperature sensor provides thermal feedback information regarding a measured temperature to the stimulation device; and
adjusting the controller to vary at least one parameter of the electrical stimulation in response to the thermal feedback information received from the temperature sensor to create a cooling effect at at least one of the contact surface of the stimulation device or the patient's tissue adjacent the contact surface.

17. The method of claim 11, further comprising:
identifying a second targeted nervous system structure;
positioning a second electrical stimulation device at a second treatment site adjacent an outer surface of the patient's skin proximate neural- and non-neural tissue of the second targeted nervous system structure, the second electrical stimulation device comprising a second electrode that provides electrical stimulation to the second treatment site and a second controller for directing operation of the second electrode; and
delivering a second electrical stimulation transcutaneously to the second treatment site via the second electrode;
wherein the application of the electrical stimulation to the second treatment site modulates a function of at least one of the neural- and/or non-neural tissue of the second targeted nervous system structure, inhibiting nervous signaling through the targeted neural- and/or non-neural tissue of the second targeted nervous system structure, while not damaging tissue interposed between the second stimulation device and the second targeted nervous system structure.

18. The method of claim 17, wherein the first and second electrical stimulation devices operate independently,
   wherein at least a portion of the application of the electrical stimulation at the treatment site and at least a portion of the application of electrical stimulation at the second treatment site both occur simultaneously.

19. The method of claim 11, wherein the step of positioning the electrical stimulation device proximate the treatment site comprises:
   delivering an initial stimulation to the treatment site via the electrode;
   measuring at least one of a voltage and a current at the electrode; and
   adjusting a position of the electrode at the treatment site until the measured voltage and/or current correspond to a threshold voltage and a threshold current, respectively.

20. The method of claim 11, further comprising:
   confirming an alignment of the electrode with the occipital nerve by stimulating a physiological response in the patient and measuring at least one of a nervous tissue signal, a cutaneous temperature change, a cutaneous blood flow change, a skin conductance change, a heart rate change, or a change in muscle activity,
   wherein an increase in nervous tissue signaling is indicative of placement of the stimulation device in alignment with the occipital nerve,
   wherein a change in cutaneous temperature is indicative of placement of the stimulation device in alignment with the occipital nerve,
   wherein a change in cutaneous blood flow is indicative of placement of the stimulation device in alignment with the occipital nerve,
   wherein a change in skin conductance is indicative of placement of placement of the stimulation device in alignment with the occipital nerve, and
   wherein an increase in muscle activity proximate the targeted nervous structure is indicative of placement of the stimulation device in alignment with the occipital nerve.

* * * * *